United States Patent
Iwamoto et al.

(10) Patent No.: US 9,492,137 B2
(45) Date of Patent: Nov. 15, 2016

(54) PORTABLE RADIOGRAPHIC IMAGING APPARATUS AND SYSTEM

(71) Applicant: FUJIFILM Corporation, Tokyo (JP)

(72) Inventors: Takahiro Iwamoto, Ashigarakami-gun (JP); Keiji Tsubota, Ashigarakami-gun (JP); Naoyuki Nishino, Ashigarakami-gun (JP); Yoshimitsu Kudo, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 227 days.

(21) Appl. No.: 14/472,561

(22) Filed: Aug. 29, 2014

(65) Prior Publication Data
US 2015/0078527 A1 Mar. 19, 2015

(30) Foreign Application Priority Data

Sep. 17, 2013 (JP) .................................. 2013-192468
Feb. 19, 2014 (JP) .................................. 2014-029991

(51) Int. Cl.
*G01D 18/00* (2006.01)
*A61B 6/00* (2006.01)

(52) U.S. Cl.
CPC ............. *A61B 6/563* (2013.01); *A61B 6/4283* (2013.01); *A61B 6/4405* (2013.01); *A61B 6/4233* (2013.01)

(58) Field of Classification Search
CPC .. A61B 6/563; A61B 6/4405; A61B 6/4283; A61B 7/26; A61B 1/385; A61B 6/4233
USPC ................................... 378/91, 193–198, 207
See application file for complete search history.

(56) References Cited

U.S. PATENT DOCUMENTS

2009/0039297 A1* 2/2009 Ohta .................... G03B 42/04
250/582
2013/0195251 A1 8/2013 Saigusa et al.

FOREIGN PATENT DOCUMENTS

| JP | 2005-13310 A | 1/2005 |
| JP | 2005-144038 A | 6/2005 |
| JP | 2011-98025 A | 5/2011 |
| JP | 2013-153790 A | 8/2013 |

OTHER PUBLICATIONS

Japanese Office Action issued Aug. 3, 2016 in JP 2014-029991.

* cited by examiner

*Primary Examiner* — Courtney Thomas
(74) *Attorney, Agent, or Firm* — Birch, Stewart, Kolasch & Birch, LLP

(57) ABSTRACT

A portable X-ray imaging apparatus includes an electronic cassette for imaging of an X-ray image and transmitting the X-ray image wirelessly. An image receiving unit communicates with the electronic cassette and receives the X-ray image wirelessly. A passive monitoring device receives ambient electromagnetic waves to measure communication environment by passive monitoring. An active monitoring device performs data communication between the electronic cassette and the image receiving unit to measure the communication environment by active monitoring. Furthermore, an evaluation device detects a cause of a communication failure by considering a result of the passive monitoring and a result of the active monitoring. The evaluation device detects that the cause of the communication failure is a blocking object blocking radio waves or a relative position between the electronic cassette and the image receiving unit according to the results of the passive and active monitoring.

20 Claims, 37 Drawing Sheets

FIG. 22

STATUS MESSAGE (EXAMPLE PATTERN 1)

No channel is available now.
Waiting time is required for image transmission
due to high traffic load.

Wait for a moment or use wired communication.

STATUS MESSAGE (EXAMPLE PATTERN 2)

A medical instrument receiving influence of
radio waves may be present locally.

Use wired communication instead of radio
communication.

STATUS MESSAGE (EXAMPLE PATTERN 3)

A noise source harmful to radio communication is present locally.
Long waiting time is required for image transmission because errors or delays may occur frequently in radio communication.

Wait for a moment or use wired communication.

STATUS MESSAGE (EXAMPLE PATTERN 4)

The transmission speed is low due to a noise source harmful to radio communication.

Waiting time is required for image transmission. Estimated time: 30 sec.
The time is from the end of the irradiation until display of the image.

STATUS MESSAGE (EXAMPLE PATTERN 5)

Radio communication environment is good.

Estimated time: 5 sec.

The time is from the end of the irradiation until display of the image.

STATUS MESSAGE (EXAMPLE PATTERN 6)

The transmission speed is low due to a communication error with an improper relative position of the console and interface unit to the electronic cassette, or with influence of a blocking object present in the room.

Waiting time is required for image transmission.
Estimated time: 2 min.

Use wired communication.

OK

~106

F I G . 28

| | | | | IEEE802.11a, IEEE802.11g | | | | |
|---|---|---|---|---|---|---|---|---|
| DATA MODULATION | BPSK 1/2 | BPSK 3/4 | QPSK 1/2 | QPSK 3/4 | 16QAM 1/2 | 16QAM 3/4 | 64QAM 2/3 | 64QAM 3/4 |
| TRANSMISSION SPEED | 6Mbps | 9Mbps | 12Mbps | 18Mbps | 24Mbps | 36Mbps | 48Mbps | 54Mbps |

| ELAPSED TIME (sec) | TRANSMISSION SPEED | POSITION INFO |
|---|---|---|
| 0.0 | 8Mbps | X0、Y0 |
| 0.5 | 8Mbps | X1、Y1 |
| 1.0 | 8Mbps | X2、Y2 |
| 1.5 | 10Mbps | X3、Y3 |
| 2.0 | 12Mbps | X4、Y4 |
| 2.5 | 20Mbps | X5、Y5 |
| 3.0 | 22Mbps | X6、Y6 |
| 3.5 | 24Mbps | X7、Y7 |
| 4.0 | 30Mbps | X8、Y8 |

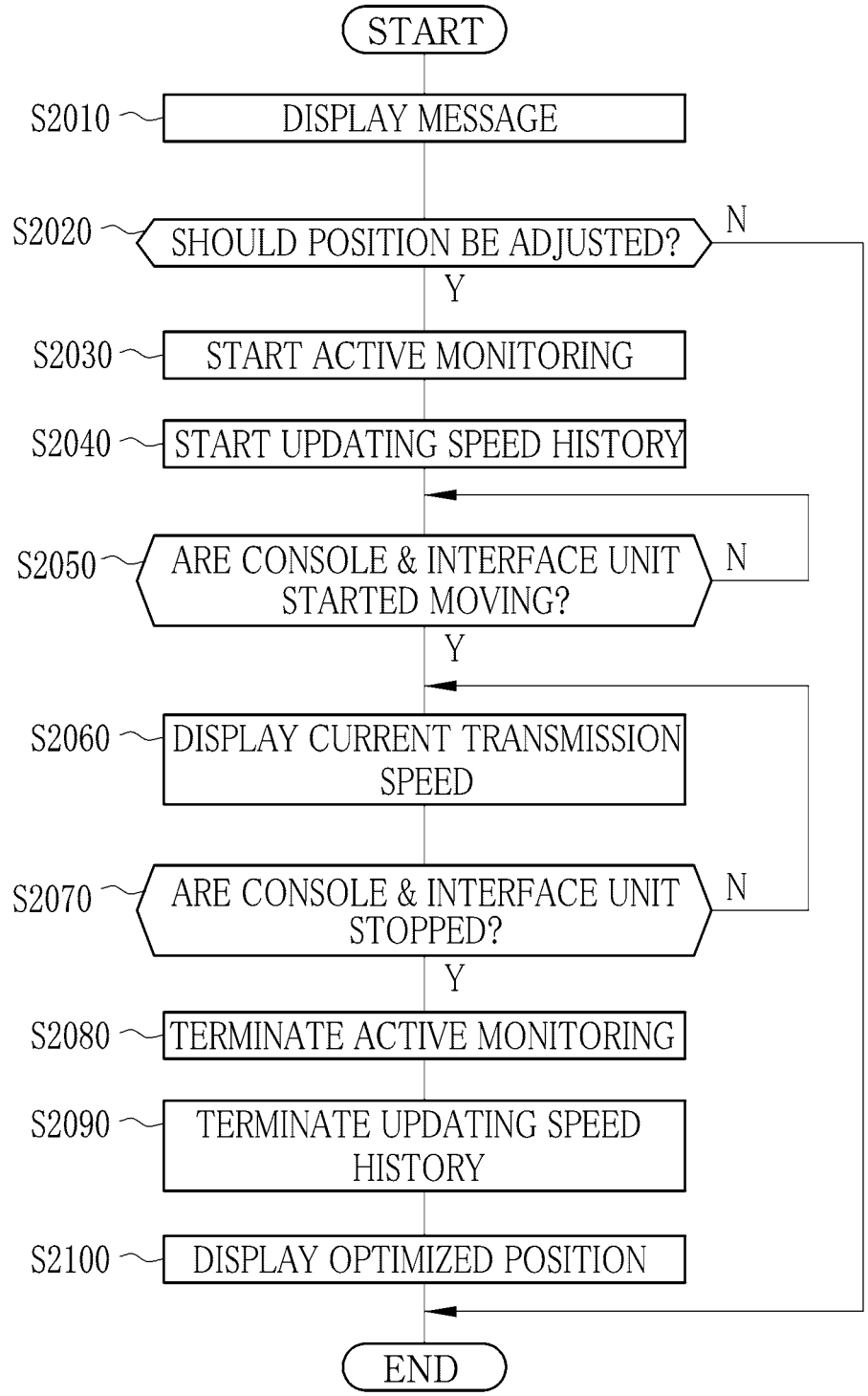

F I G . 37

STATUS MESSAGE (EXAMPLE PATTERN 6)

The transmission speed is low due to a communication error with an improper relative position of the console and interface unit to the electronic cassette, or with influence of a blocking object present in the room. ~113

Waiting time is required for image transmission. Estimated time: 2 min.

You can adjust the position by moving the console and interface unit.

An optimized position will be set for the position adjustment.

Do you adjust the position?

113A~[ YES ]   [ NO ]~113B

FIG. 38

POSITION ADJUSTMENT (ASSIST)

SPEED SCREEN

Optimizing now.

Current transmission speed | Theoretical value

20Mbps | 54Mbps

Do you end the position adjustment?

END ~114A

~114

```
POSITION ADJUSTMENT (ASSIST)

OPTIMIZATION SCREEN
```
~116

The optimized position is defined as a position 3 sec. before the stop of movement.
Return by 50 cm in reverse to a moving direction before the stop.

Transmission speed in the optimized position: 50 Mbps.
Estimated time: 5 sec.

The time is from the end of the irradiation until display of the image.

OK

PP
BP  O

~117

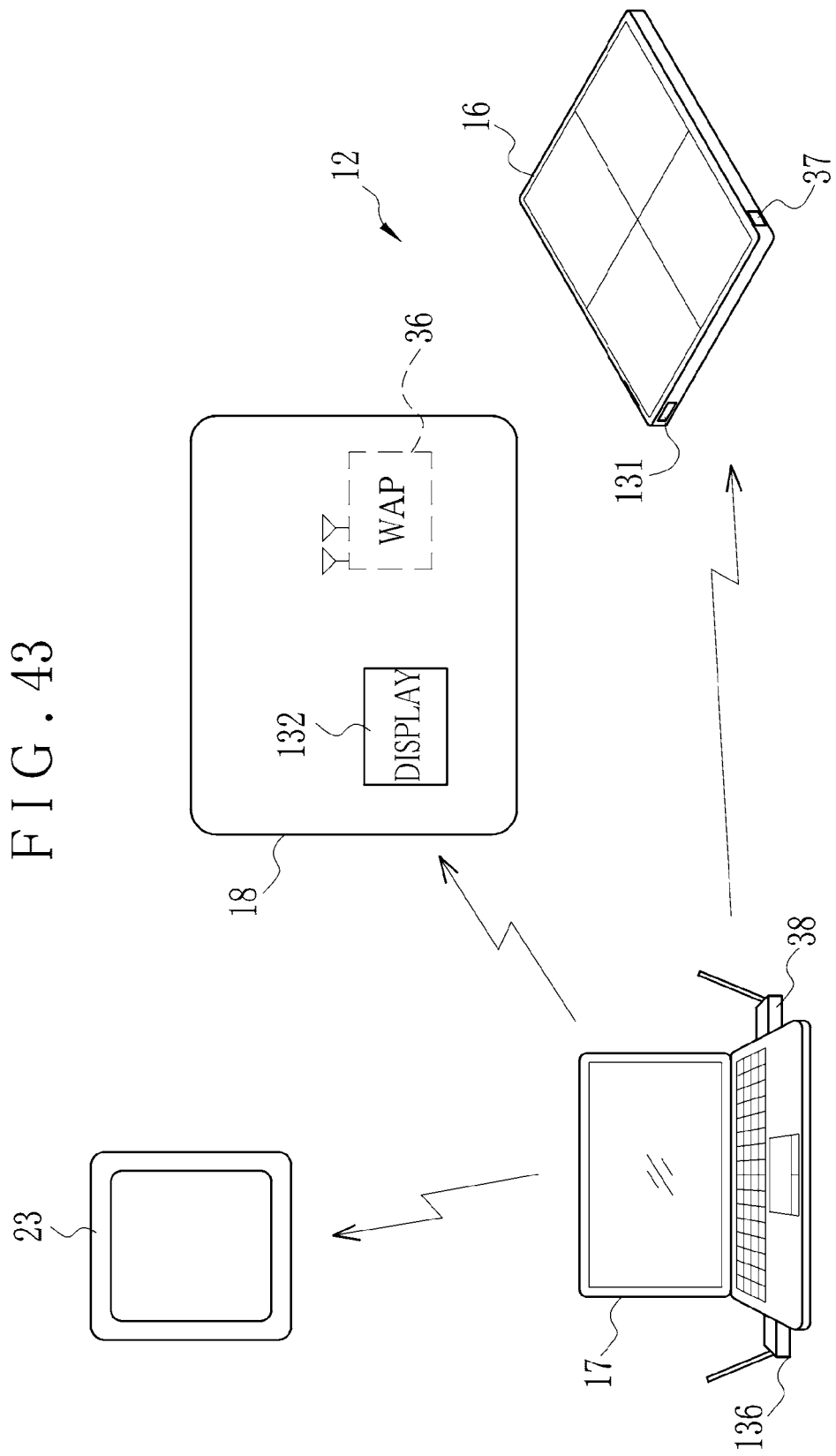

PORTABLE RADIOGRAPHIC IMAGING APPARATUS AND SYSTEM

CROSS-REFERENCE TO RELATED APPLICATION

This application claims priority under 35 USC 19 from Japanese Patent Application No. 2013-192468, filed 17 Sep. 2013, and Japanese Patent Application No. 2014-029991, filed 19 Feb. 2014, the disclosure of which is incorporated by reference herein.

BACKGROUND OF THE INVENTION

1. Field of the Invention

The present invention relates to a portable radiographic imaging apparatus and system. More particularly, the present invention relates to a portable radiographic imaging apparatus and system in which causes of a communication failure can be estimated exactly and rapidly.

2. Description Related to the Prior Art

An X-ray imaging system or radiographic imaging system is widely used in medical service in a hospital. The X-ray imaging system includes an X-ray source apparatus or radiation source apparatus, and an X-ray imaging apparatus or radiographic imaging apparatus. The X-ray source apparatus generates X-rays. The X-ray imaging apparatus forms an X-ray image or radiation image of a body of a patient by receiving X-rays transmitted through the body. The X-ray source apparatus includes an X-ray source, a source driver (controllable) and a start switch. The X-ray source applies X-rays to the body. The source driver drives and controls the X-ray source. The start switch inputs a command signal to the source driver to turn on the X-ray source. The X-ray imaging apparatus includes an X-ray image detector or radiation image detector, and a console unit, which receives a command signal for the X-ray image detector and the X-ray image from the X-ray image detector, and displays the X-ray image.

The X-ray image detector has a sensor panel or a flat panel detector (FPD), and detects the X-ray image by converting X-rays transmitted though a body into an electric signal. The X-ray image detector transmits the X-ray image immediately to the console unit which operates for displaying an image visibly. The use of the X-ray image detector is highly advantageous over radiography with an X-ray film or IP cassette (imaging plate cassette), because the image can be checked shortly after the imaging.

Examples of X-ray image detectors include a stationary type installed in an examination room, and a portable type, which is an electronic cassette having a portable housing and the sensor panel contained in the portable housing. A portable X-ray imaging apparatus can be constituted by a combination of the electronic cassette with the console unit of a small form. The electronic cassette is usable in a state fixedly positioned on a floor stand or the like in the examination room for imaging the body in an erect posture or supine posture. Also, the electronic cassette is useful in X-ray imaging of in-patient care in which an operator goes to a hospital room of a patient of limited mobility, namely in a condition without possibility of moving to the examination room.

Also, there is a portable type of the X-ray source apparatus. A movable medical cart is so constructed to carry the X-ray source apparatus. The medical cart is a tool widely used in a hospital. The portable X-ray imaging apparatus is also placed on the medical cart and moved into the hospital rooms one after another for the in-patient care.

JP-A 2011-098025 discloses the X-ray imaging apparatus of a type of radio communication between the electronic cassette and the console unit for transmitting data including the X-ray image. There are various modes of positioning the electronic cassette according to body parts of interest in the body. The electronic cassette may be disposed between the body and a bed, or may be held by hands of the patient. It is unnecessary to connect a cable to the electronic cassette by use of the radio communication, so that the positioning of the electronic cassette can be freely carried out without consideration of a path of the cable.

However, the radio communication is influenced by radio interference of various forms, for example, with radio waves emitted by a portable terminal device of radio communication manually carried by a nurse, physician and the like, and electromagnetic noise created by an electromagnetic medical instrument, such as a thermal treatment device and an electrocautery device. A communication failure such as a delay may be created by influence of the radio interference in a communication environment where the portable terminal device or the electromagnetic medical instrument is present near to the X-ray imaging apparatus of the radio communication. A problem arises in that a constantly high quality cannot be maintained in the communication.

In the X-ray imaging apparatus of JP-A 2011-098025, a transmission speed is measured in the transmission of the X-ray image from the electronic cassette to the console unit, to measure and check the communication environment of the X-ray imaging apparatus. The transmission speed is determined by a data size of the X-ray image and time of the image transmission. In JP-A 2011-098025, the X-ray imaging apparatus produces data of a communication history by storing the transmission speed and a time point of the transmission in a correlated manner at each one event of imaging. Also, it is suggested additionally to store position information of the electronic cassette to the communication history in association with the transmission speed, such as an ID of the floor stand of the apparatus of the electronic cassette.

The communication history is used by a system administrator who administers a computer system in a hospital facility or a network in the hospital facility, such as local area network (LAN), for the purpose of checking the communication environment in the hospital facility and estimating causes of the communication failure. For example, it is likely according to the communication history that delay occurs in a particular time zone in a day. Then the system administrator designates the time zone with high traffic load in the communication, and recognizes that the delay is caused by the high traffic load. Otherwise, the causes of the communication failure are estimated by checking whether there is influence of the electromagnetic medical instrument as a source of the radio interference according to continuation of the time zone of the delay in the communication. It is possible for the system administrator to remove influence of the radio interference according to the estimated causes, for example, by changing a frequency of a channel of the radio communication.

The data size of the X-ray image is large in general, so that influence of the communication failure to the time of the image transmission is considerable. The use of the technique in JP-A 2011-098025 is typically important for the purpose of coping with the communication failure in the X-ray imaging apparatus.

However, there is a problem in the method in JP-A 2011-098025 in that causes of the communication failure corresponding to the communication environment of a newest state cannot be recognized correctly, as a method of producing the communication history by correlating the transmission speed with a time point and a stationary type of the imaging apparatus after measurement of the transmission speed in each event of the imaging.

Positions and the number of the portable terminal devices of radio communication are changed with time by movement of nurses, physicians and the like in the hospital facility with the hospital room for patients. Also, positions and the number of the electromagnetic medical instruments vary according to places in the hospital facility. Therefore, there occur changes in the communication environment in the hospital facility according to time and places. In relation to the communication history disclosed in JP-A 2011-098025, there occurs a time lag between the production and reading of the communication history, as the newest information of the communication history is different from the communication history in the stored form due to the frequent changes in the communication environment. A problem arises in the failure in proper recognition of causes of the communication failure.

A method of measuring the communication environment in JP-A 2011-098025 is only measurement of the transmission speed by data communication. It is likely that the communication failure cannot be estimated exactly even in consideration of the newest state of the communication environment in the communication history. For example, the communication failure including the delay is caused not only by radio waves and electromagnetic noise but also by a blocking object or impropriety of a relative position. The blocking object may be present in the hospital room and blocks radio waves. The relative position constitutes a distance or direction in relation to the electronic cassette and the console unit on a condition of directivity of radio waves. Even though the drop in the transmission speed can be detected, the method of measuring the transmission speed is insufficient for recognizing causes of the drop in the transmission speed, for example, electromagnetic waves, or a blocking object or relative position.

JP-A 2011-098025 discloses the method in which the communication history of plural events (requests) of imaging is referred to for estimating causes of the communication failure. No usable information of the communication history can be obtained for the estimation before completion of the plural events of the imaging. The communication failure cannot be avoided in the imaging in the course of producing the communication history. There is a problem in low rapidity for coping with the communication failure.

As described above, the portable X-ray imaging apparatus is used for the in-patient care by movement in the hospital facility with unexpected fine changes in the communication failure, unlike the stationary type of the apparatus fixed in the examination room. According to a research of the medical service in hospitals, the number of imaging requests for the in-patient care is 20 per day in one hospital facility, and may be increased by 30 as additional urgent requests due to the progress of numerous patients. Only one technician or operator frequently works for imaging in the in-patient care. Thus, a task of 50 or more imaging requests must be performed only by himself or herself in a day. In general, each one event of imaging of the imaging request takes about 5 minutes. It follows the imaging of the in-patient care is carried out in a severely restricted condition of the operator. However, causes of the communication failure cannot be recognized exactly or quickly in the medical service in the hospital facility, so that no appropriate solution for a problem at each one of the hospital rooms can be made for each event of the radiographic imaging.

SUMMARY OF THE INVENTION

In view of the foregoing problems, an object of the present invention is to provide a portable radiographic imaging apparatus and system in which causes of a communication failure can be estimated exactly and rapidly.

In order to achieve the above and other objects and advantages of this invention, a portable radiographic imaging apparatus includes an electronic cassette for imaging of a radiation image and transmitting the radiation image wirelessly. An image receiving unit communicates with the electronic cassette and receives the radiation image wirelessly. A passive monitoring device receives ambient electromagnetic waves to measure communication environment by passive monitoring. An active monitoring device performs data communication between the electronic cassette and the image receiving unit to measure the communication environment by active monitoring.

Preferably, furthermore, an evaluation device detects a cause of a communication failure by considering a result of the passive monitoring and a result of the active monitoring.

Preferably, the result of the passive monitoring includes at least one of intensity of a particular frequency of the electromagnetic waves, spectral intensity of frequency distribution of the intensity of the electromagnetic waves, and a time profile of changes in the intensity or the spectral intensity with time.

Preferably, the result of the active monitoring includes a transmission speed.

Preferably, furthermore, a controller outputs environment information of the communication environment to a display device, the environment information including at least one of the result of the passive monitoring, the result of the active monitoring, and the detected cause of the communication failure detected by the evaluation device.

Preferably, the result of the passive monitoring includes at least one of channel information of a radio communication channel of radio waves used by a radio communication device being present locally, and noise information of electromagnetic noise created by a device being present locally.

Preferably, the evaluation device further checks enablement of wireless transmission of the radiation image according to at least one of the result of the passive monitoring, the result of the active monitoring and the cause of the communication failure. The controller further outputs information as to the enablement of the wireless transmission of the radiation image to the display device.

Preferably, the passive monitoring is performed before performing the active monitoring.

Preferably, the evaluation device checks whether the active monitoring should be performed according to the result of the passive monitoring.

Preferably, the evaluation device checks whether a medical instrument with possibility of receiving influence of radio waves is present locally according to a waveform of electromagnetic noise, and judges unavailability of the active monitoring assuming that the medical instrument is found to be present.

Preferably, the evaluation device detects that the cause of the communication failure is a blocking object blocking radio waves or a relative position between the electronic cassette and the image receiving unit according to the results of the passive and active monitoring.

Preferably, the evaluation device recognizes that the cause of the communication failure is the blocking object or the relative position according to an estimated transmission speed estimated according to the result of the passive monitoring, a measured transmission speed in the result of the active monitoring, and noise information of electromagnetic noise in the result of the passive monitoring.

Preferably, furthermore, a positioning aid device outputs information for adjusting the relative position.

Preferably, the information is a speed history of detected changes in a transmission speed by causing the active monitoring device to perform the active monitoring repeatedly while the relative position is adjusted.

Preferably, the image receiving unit includes a position sensor, and the positioning aid device produces the speed history by combining the transmission speed and position information from the position sensor.

Preferably, the positioning aid device detects an optimized position where the transmission speed is highest according to the speed history. Furthermore, a controller outputs information of the optimized position to a display device.

Preferably, the image receiving unit has the passive monitoring device, the active monitoring device and the display device.

Preferably, furthermore, a condition setting unit changes a communication setting of radio communication according to at least one of the result of the passive monitoring and the result of the active monitoring.

Preferably, the condition setting unit determines the communication setting for transmitting the radiation image by considering the result of the active monitoring of plural events different in the communication setting.

Preferably, assuming that unavailability of the wireless transmission is judged, then the controller outputs unavailability information of the wireless transmission and countermeasure information to the display device.

Preferably, furthermore, a controller outputs message information to a display device to recommend adjustment of the relative position assuming that it is detected that the cause of the communication failure is the blocking object or the relative position.

Preferably, at least one of a time point and position information of measurement of the transmission speed is combined with the transmission speed to produce the speed history.

Preferably, the image receiving unit includes a console unit for displaying the radiation image.

Preferably, furthermore, there is an interface unit for radio communication between the electronic cassette and the console unit.

Preferably, the controller performs control of transmitting entirety or part of the environment information to a portable terminal device.

Also, a portable radiographic imaging system having a portable radiation source apparatus and a portable radiographic imaging apparatus is provided. The portable radiographic imaging apparatus includes an electronic cassette for imaging of a radiation image and transmitting the radiation image wirelessly. An image receiving unit communicates with the electronic cassette and receives the radiation image wirelessly. A passive monitoring device receives ambient electromagnetic waves to measure communication environment by passive monitoring. An active monitoring device performs data communication between the electronic cassette and the image receiving unit to measure the communication environment by active monitoring.

Consequently, causes of a communication failure can be estimated exactly and rapidly, because the passive monitoring and active monitoring are performed to check the communication environment effectively.

BRIEF DESCRIPTION OF THE DRAWINGS

The above objects and advantages of the present invention will become more apparent from the following detailed description when read in connection with the accompanying drawings, in which:

FIG. 22 is a front elevation illustrating a first message screen;

FIG. 23 is a front elevation illustrating a second message screen;

FIG. 24 is a front elevation illustrating a third message screen;

FIG. 25 is a front elevation illustrating a fourth message screen;

FIG. 26 is a front elevation illustrating a fifth message screen;

FIG. 27 is a front elevation illustrating a sixth message screen;

FIG. 28 is a table illustrating an example of a transmission speed and data modulation system in the wireless LAN;

FIG. 35 is a table illustrating a speed history;

FIG. 36 is a flow chart illustrating steps of position adjustment;

FIG. 37 is a front elevation illustrating a seventh message screen;

FIG. 38 is a front elevation illustrating a speed screen;

FIG. 43 is an explanatory view illustrating various examples of display devices for a message screen.

DETAILED DESCRIPTION OF THE PREFERRED EMBODIMENT(S) OF THE PRESENT INVENTION

First Preferred Embodiment

Figure 1:
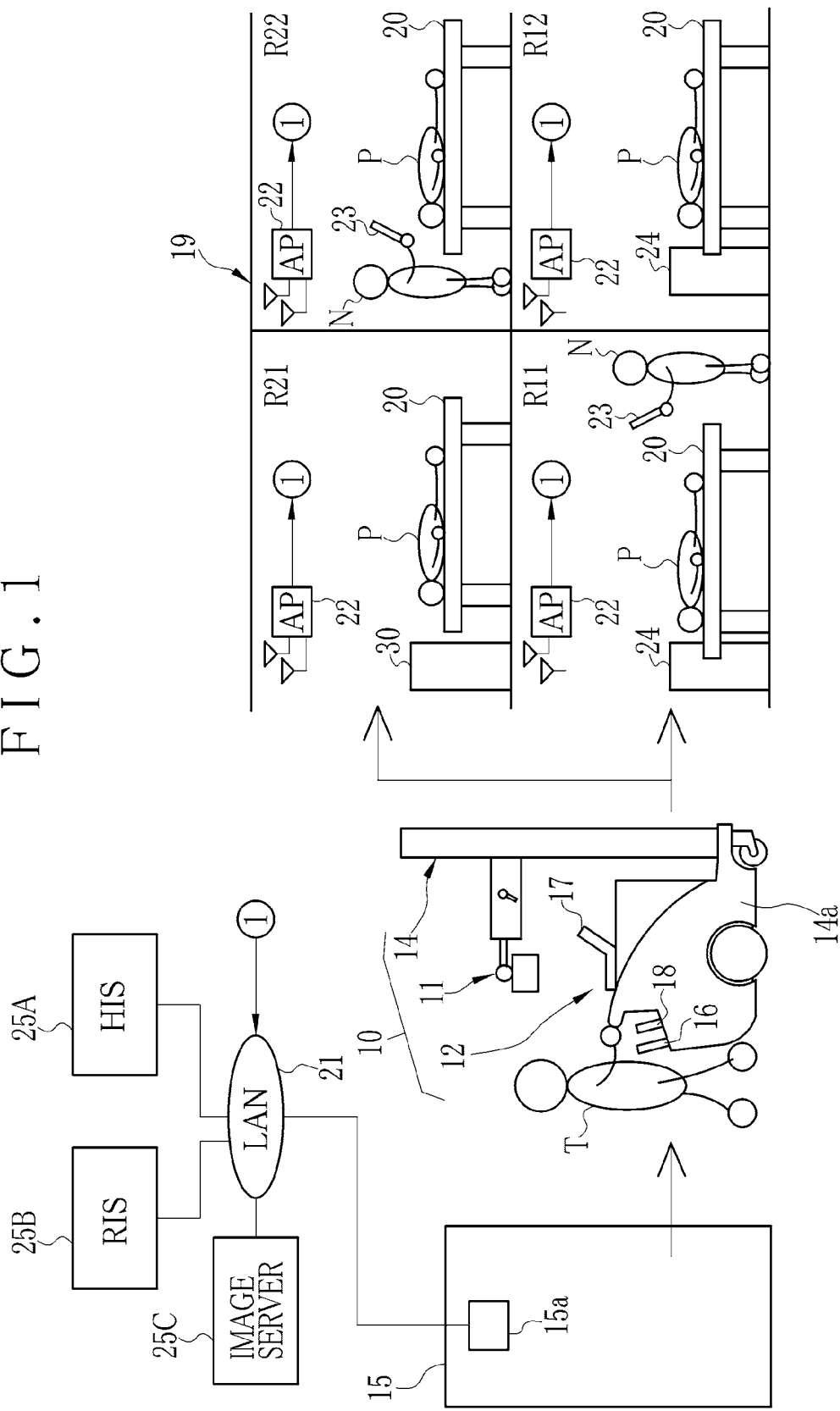
FIG. 1 is a block diagram schematically illustrating a hospital facility with a portable X-ray imaging system.

In FIG. 1, a portable X-ray imaging system 10 or portable radiographic imaging system includes a portable X-ray source apparatus 11 or portable radiation source apparatus, and a portable X-ray imaging apparatus 12 or portable radiographic imaging apparatus. A medical cart 14 is constituted by the X-ray source apparatus 11 and a cart platform 14a. The cart platform 14a has rotatable wheels for movement, so that the X-ray source apparatus 11 is usable as a mobile apparatus. The X-ray imaging apparatus 12 includes an electronic cassette 16, a portable console unit 17 or user interface unit, and a control interface unit 18 or functional unit, and can be carried by the medical cart 14. There is a storage space 15 where the medical cart 14 is stored in the hospital facility while the medical cart 14 is not used. For imaging in medical service, the X-ray imaging apparatus 12 is placed on the medical cart 14 which is moved out of the storage space 15. In a hospital facility 19, a technician or operator T manually moves the medical cart 14 to hospital rooms R11, R12, R21 and R22, and forms images of a body P of a patient of each of hospital beds 20.

An access point 22 (AP) or access point device is installed in each of the rooms and other facility parts in the hospital facility. A portable terminal device 23 of radio communication is carried and manually used by a physician, nurse and the like. A local area network 21 (LAN) is provided in the hospital facility. The access point 22 is an interface device of radio communication for connecting the portable terminal device 23 to the local area network 21 in the hospital facility. The access point 22 includes a radio communication interface and a wired communication port. The radio communication interface communicates with the portable terminal device 23. The wired communication port operates for connection to the local area network 21 by a communication cable. The radio communication interface is constructed according to a wireless LAN standard, for example, IEEE 802.11n. A LAN interface port 15a is disposed in the storage space 15 for wired connection of the local area network 21. An example of the portable terminal device 23 is a tablet computer which a user can carry easily.

In the course of the startup, the access point 22 emits a beacon signal as radio waves at an interval of approximately 100 msec for notifying the portable terminal device 23 of the presence of the access point 22. In response, the portable terminal device 23 detects the presence of the access point 22, and then requests the access point 22 for the wireless connection. A frequency of a radio communication channel is assigned to the access point 22 as wavelength for use in the radio communication. The beacon signal is emitted at the assigned frequency. The portable terminal device 23 selects frequency of the radio communication channel according to the frequency used by the access point 22. In case the portable terminal device 23 requests the access point 22 for the wireless connection, processing of authorization is performed by use of a password or the like. In the authorization, a logical communication link is established between the portable terminal device 23 and the access point 22 upon receiving an enable signal from the access point 22 to the portable terminal device 23, so that the wireless connection with the access point 22 is established.

An IP address (Internet Protocol address) is assigned by the access point 22 to the portable terminal device 23 upon establishing the wireless connection. Then the portable terminal device 23 is enabled to access to a HIS server 25A or Hospital Information System server, by connecting to the local area network 21 through the access point 22. Also, the access point 22 is wirelessly communicable with a plurality of the portable terminal devices 23. To this end, one radio communication channel used by the access point 22 is shared by the portable terminal devices 23 in a time-sharing manner.

Medical instruments are disposed in hospital rooms R11, R12, R21 and R22 for diagnosis, treatment and healthcare of a patient P. For example, an electromagnetic medical instrument 24 (circuit apparatus) is used, and may create electromagnetic noise as a cause of radio interference for radio communication. Examples of the electromagnetic medical instrument 24 are a thermal treatment device, an electrocautery device, and a radio transmitter for wirelessly transmitting body information such as a vital sign of the body P. Assuming that a treatment room (not shown) is disposed adjacently to the hospital rooms R11, R12, R21 and R22, electromagnetic noise from the electromagnetic medical instrument 24 in the treatment room may enter the hospital rooms R11, R12, R21 and R22.

Also, there is a particular medical instrument 30 which is likely to be influenced by radio waves generated by the portable terminal device 23 in the course of radio communication. It is preferable to stop the radio communication in the local area network 21 where the particular medical instrument 30 is disposed.

Plural systems are connected to the local area network 21, including the HIS server 25A, a RIS server 25B or Radiology Information System server, and an image server 25C.

The HIS server 25A operates for managing electronic medical charts, and is mainly accessed by local terminal devices which doctors, nurses and the like use in hospital departments, such as internal medicine, surgery and the like. Examples of the local terminal devices include a desktop computer, notebook computer, the portable terminal device 23 and the like. The local terminal devices are used to view the medical charts, input information of diagnosis or treatment and the like.

The RIS server 25B is established by a radiology department, and used for managing imaging requests as request information from hospital departments to the radiology department. Information of the imaging request includes requester information, case information, body part information, direction information, and note information. Requesters of the requester information include a hospital department and a name of a doctor (physician). Examples of the case information include a name, age and sex of a patient (body). Body parts of the body part information include a head, chest, abdomen, hands, fingers and the like. Imaging directions of the direction information include a front direction, lateral direction, diagonal direction, PA (posteroanterior direction) and AP (anteroposterior direction). Examples of the note information include a purpose of imaging, progress note and message from the doctor (physician). The operator T checks the imaging request with the console unit 17, determines an imaging condition suitable for the imaging request, and sets the imaging condition in the electronic cassette 16 and the X-ray source apparatus 11.

Figure 2:
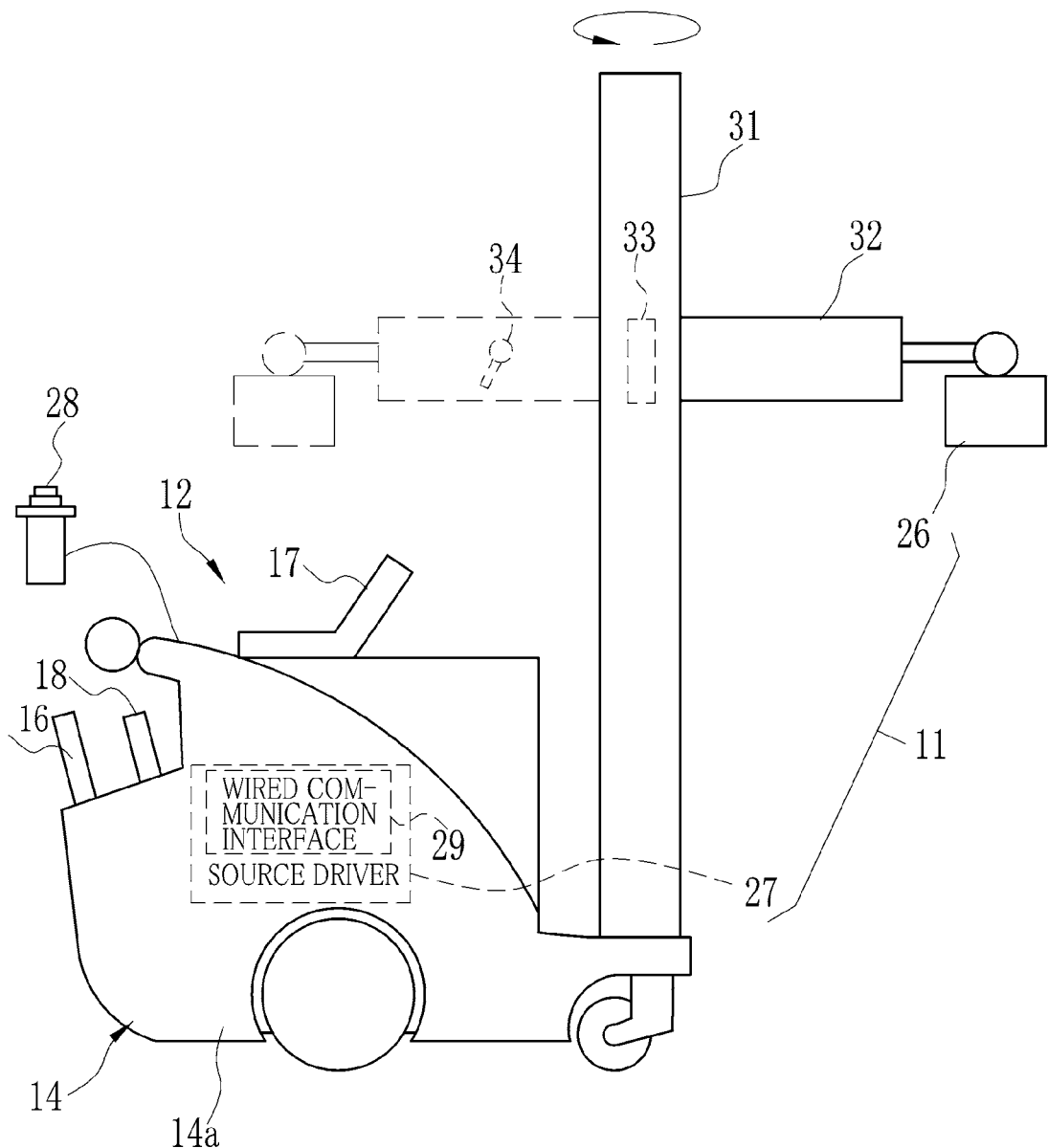
FIG. 2 is a side elevation illustrating a medical cart for radiography.

The imaging condition includes an irradiation condition of an X-ray source 26 of FIG. 2. The irradiation condition is defined by a tube voltage (kV), a tube current (mA) and irradiation time (sec) of X-rays. The tube voltage determines energy spectrum of X-rays from the X-ray source 26. The tube current determines a radiation dose per unit time. A cumulative radiation dose of X-rays is determined as a product of multiplication of the tube current and irradiation time. Input data of the irradiation condition can be values of the tube current and irradiation time, and can be a value of a current-time product (mAs) of the tube current and irradiation time.

The image server 25C stores and manages image data of X-ray images formed by the X-ray imaging apparatus 12 according to an imaging request. Access to the image server 25C is possible even from a local terminal device disposed at a requester of the imaging request. A physician or operator with the terminal device can view X-ray images by accessing the image server 25C.

In the X-ray imaging apparatus 12, the console unit 17 can access the RIS server 25B and the image server 25C through the local area network 21. The console unit 17 acquires an imaging request from the RIS server 25B, and transmits an X-ray image to the image server 25C. In the storage space 15, the console unit 17 is connected to the LAN interface port 15a in a wired connection, and directly communicable with the RIS server 25B and the image server 25C. In the hospital facility 19, the console unit 17 is communicable with the RIS server 25B and the image server 25C for the access by wireless connection with the access point 22. Note that the access point 22 can be disposed in the storage space 15. The console unit 17 can wirelessly connect to the access point 22 instead of using the LAN interface port 15a, for access to the RIS server 25B and the image server 25C.

In FIG. 2, the X-ray source apparatus 11 includes the X-ray source 26, a source driver 27 (controllable) and a start switch 28. The source driver 27 controls the X-ray source 26. The X-ray source 26 includes an X-ray tube and a collimator (not shown). The X-ray tube emits X-rays. The collimator limits a path of irradiation to an object downstream of the X-ray tube. Various elements are associated with the X-ray tube, including a filament (cathode) and target (anode). The filament generates thermal electron. The target emits X-rays by collision of the thermal electron from the filament. The collimator is constituted by four movable plates of metal lead arranged quadrilaterally for blocking X-rays. An emission opening of a quadrilateral shape is defined in the collimator at the center for transmitting X-rays.

A support column 31 is disposed in the medical cart 14 to extend vertically. A support arm 32 is disposed on the support column 31 to extend horizontally. The X-ray source 26 is supported at a distal end of the support arm 32. The support column 31 is rotatable about its longitudinal axis. The support arm 32 and the X-ray source 26 are rotated by rotation of the support column 31. The support arm 32 is movable up and down relative to the support column 31. The X-ray source 26 is supported on the support arm 32 in a rotatable manner. The support arm 32 is extendable so that the X-ray source 26 is shiftable also in a horizontal direction. Thus, a position of irradiation and direction of the X-ray source 26 are adjusted by rotation of the support column 31, vertical movement and extension of the support arm 32, and rotation of the X-ray source 26. A lock mechanism 33 is disposed in the support column 31.

The lock mechanism 33 is operated while the medical cart 14 is run and prevents the support arm 32 and the X-ray source 26 from shifting by locking the support column 31, the support arm 32 and the X-ray source 26. For example, the lock mechanism 33 includes a lock pin movable between a first position for regulating the shift of the X-ray source 26 and a second position for allowing the X-ray source 26 to shift by release. In case a lock button 34 is depressed, the lock pin is moved to engage and release the lock mechanism 33. The lock mechanism 33 generates an unlock signal at the time of release. The unlock signal is transmitted through a cable to the source driver 27.

The source driver 27 includes a high voltage source and a controller. The high voltage source supplies the X-ray source 26 with high voltage. The controller controls the tube voltage, tube current and irradiation time. The high voltage source includes a transformer and a high voltage cable. The transformer boosts an input voltage to generate the high voltage or tube voltage. The high voltage cable supplies the X-ray source 26 with the tube voltage or drive voltage. An input panel (not shown) of the source driver 27 is manually operated by the operator T, and inputs an irradiation condition including the tube voltage, tube current and irradiation time. Also, an irradiation condition can be transmitted by the console unit 17 to the source driver 27 and input in the source driver 27.

The start switch 28 is operated by the operator T, and connected to the source driver 27 by a signal cable. The start switch 28 is a button of a two-step type. The start switch 28, upon being depressed halfway at a first step, generates a warm-up signal for warming up the X-ray source 26, and upon being depressed fully at a second step, generates a start signal for irradiation of the X-ray source 26. Those signals are input by the signal cable to the source driver 27.

The source driver 27 controls operation of the X-ray source 26 according to a start signal from the start switch 28. Upon inputting the start signal, the source driver 27 starts powering the X-ray source 26. A timer is started and measures elapsed time upon the start of irradiating X-rays. In case the elapsed time becomes equal to the predetermined irradiation time in the irradiation condition, the source driver 27 stops irradiation of X-rays. The irradiation time changes according to the irradiation condition. Also, the source driver 27 operates assuming that the measured time becomes equal to a maximum irradiation time predetermined in the source driver 27 for the fail-safe purpose. The actual irradiation time according to the irradiation condition is determined in a range of the maximum irradiation time.

A wired communication interface 29 (wired communication port) is incorporated in the source driver 27. A communication cable connects the wired communication interface 29 to the console unit 17 for the purpose of communication with the X-ray imaging apparatus 12. The wired communication interface 29 receives an unlock signal from the lock mechanism 33 and transmits this to the console unit 17 through the communication cable.

Figure 3:
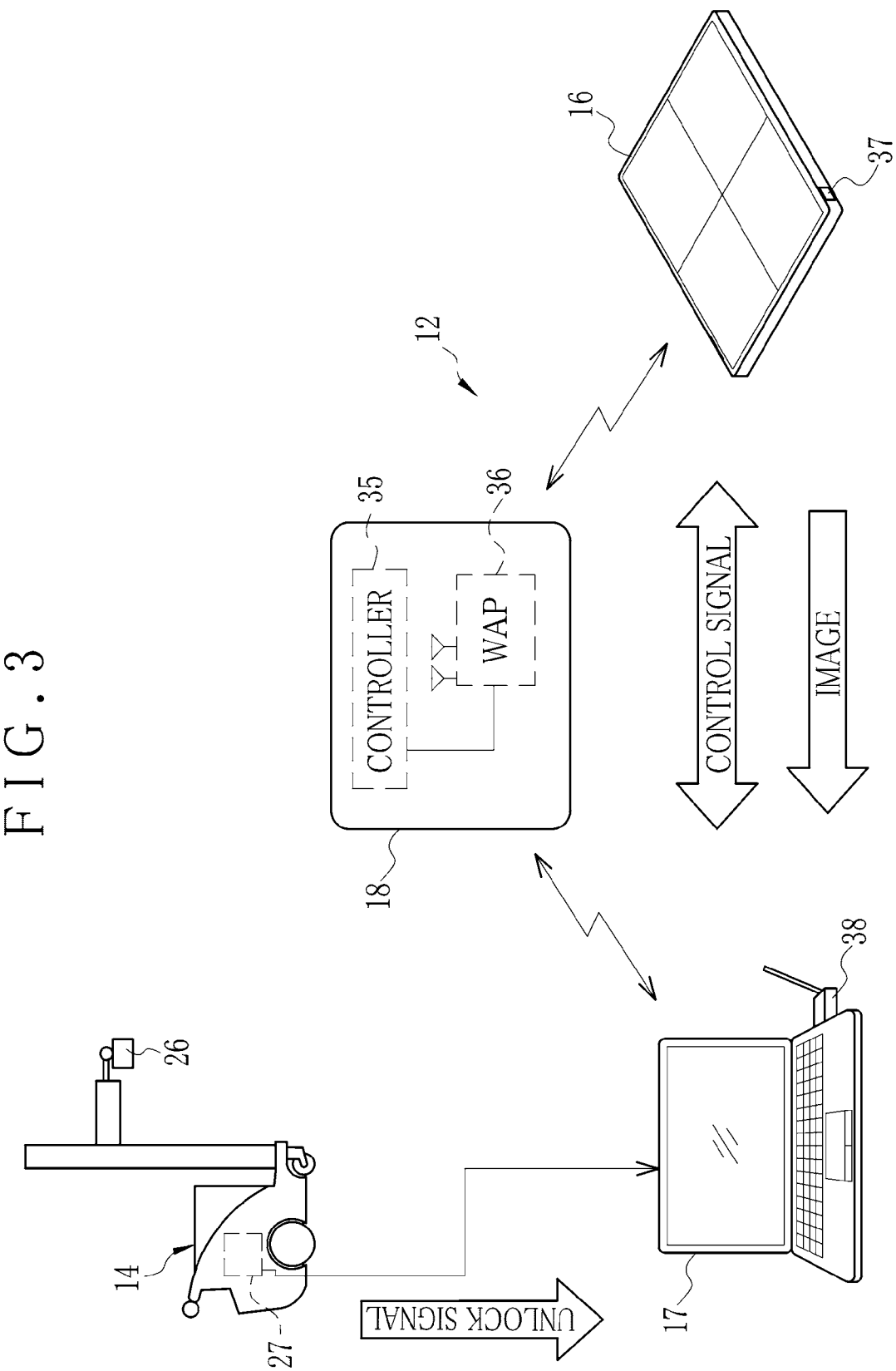
FIG. 3 is an explanatory view illustrating an X-ray imaging apparatus.

In FIG. 3, a radio communication interface is incorporated in each of the electronic cassette 16, the console unit 17 and the control interface unit 18 in the X-ray imaging apparatus 12. The electronic cassette 16 is communicable with the console unit 17 in radio communication by use of the control interface unit 18. The radio communication interface is constructed according to a wireless LAN standard, for example, IEEE 802.11n.

The control interface unit 18 includes a controller 35 and a wireless access point 36 (WAP) or wireless access point device. The controller 35 controls various elements in the control interface unit 18. The wireless access point 36 is a radio communication device for communication between the electronic cassette 16 and the console unit 17.

In a manner similar to the access point 22, the wireless access point 36 emits a beacon signal for informing the electronic cassette 16 and the console unit 17 of the presence of the wireless access point 36. Radio communication interfaces 37 and 38 of the electronic cassette 16 and the console unit 17 become connected to the wireless access point 36 wirelessly in a step similar to the connection of the portable terminal device 23 to the access point 22. Thus, the radio communication is carried out between the electronic cassette 16 and the console unit 17. A frequency of a radio communication channel for use in the initial setting is assigned to the wireless access point 36. The frequency of the radio communication channel is changeable according to a command signal from the console unit 17. The electronic cassette 16 and the console unit 17 select one of the frequencies according to the frequency of the radio communication channel used by the wireless access point 36.

The electronic cassette 16 communicates with the console unit 17 by use of the wireless access point 36 in an infrastructure mode, which is different from an ad-hoc mode of direct communication. The console unit 17 transmits signals to the electronic cassette 16, the signals including an imaging condition and a control signal, such as a standby signal input by an technician or operator T. In turn, the electronic cassette 16 transmits signals to the console unit 17, the signals including a response to the control signal, and an X-ray image detected by the electronic cassette 16. The electronic cassette 16 upon receiving the standby signal is set to become ready for imaging.

In the present embodiment, an X-ray image transmitted by the electronic cassette 16 is received by the console unit 17 through the control interface unit 18. The control interface unit 18 and the console unit 17 constitute an image receiving unit. Note that radio communication can be performed between the electronic cassette 16 and the console unit 17 in an ad-hoc mode instead of an infrastructure mode. The control interface unit 18 is unnecessary. The console unit 17 constitutes an image receiving unit.

The wireless access point 36 transmits the radio communication from the console unit 17 to the source driver 27 carried by the medical cart 14. Thus, an irradiation condition can be wirelessly transmitted by the console unit 17 to the source driver 27. Transmission of the irradiation condition from the console unit 17 makes it unnecessary manually to input the irradiation condition to the source driver 27 by use of a user input interface in the medical cart 14. Also, the X-ray imaging apparatus 12 is enabled by the wireless access point 36 to receive a turn-on signal of the start switch 28 from the source driver 27. Furthermore, the console unit 17 receives an unlock signal from the source driver 27 through the wireless access point 36.

Figure 4:
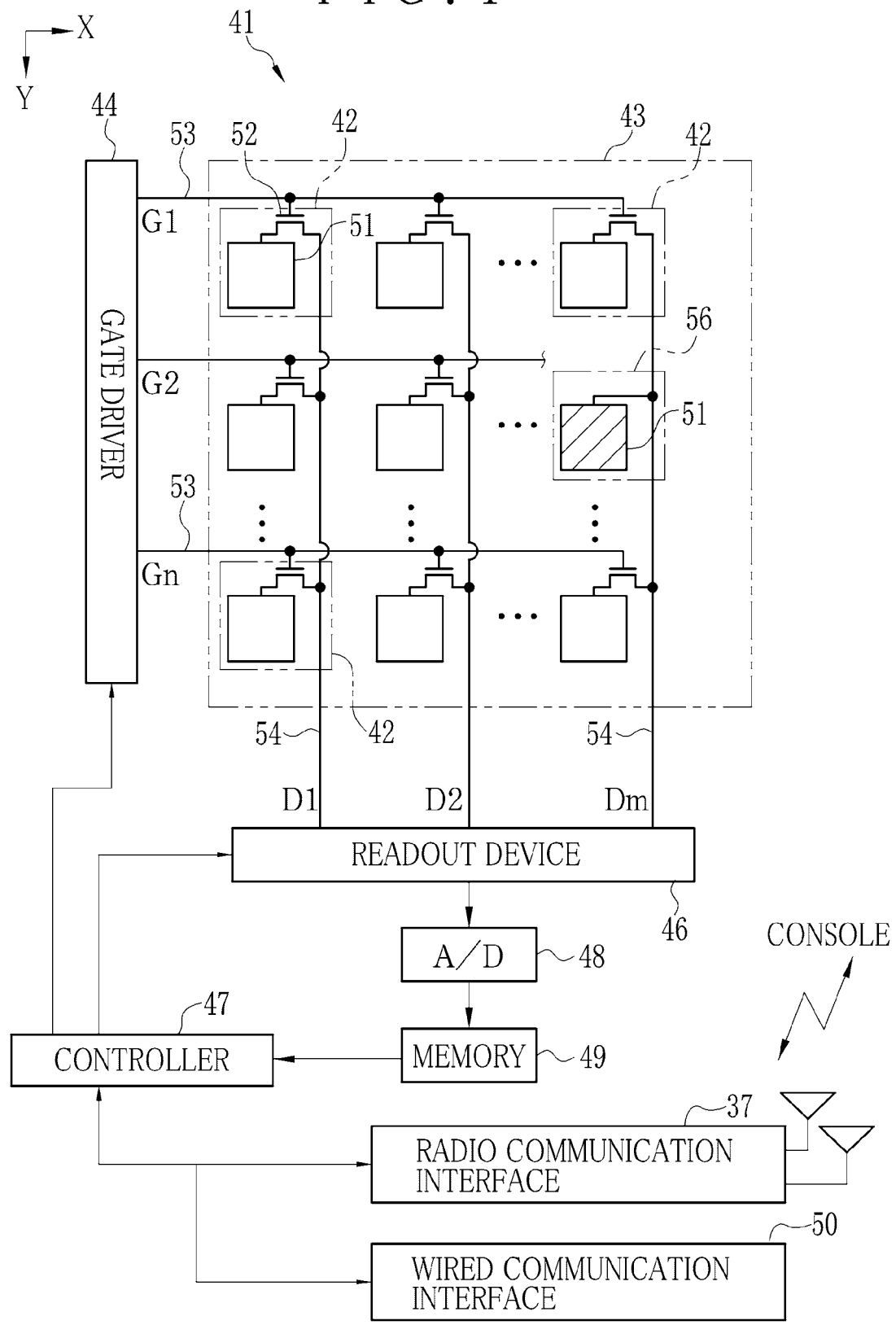
FIG. 4 is a block diagram schematically illustrating a sensor panel.

The electronic cassette 16 is constituted by a sensor panel 41 or flat panel detector (FPD) of FIG. 4, and a portable housing for containing the sensor panel 41. The electronic cassette 16 is a portable X-ray imaging apparatus for receiving X-rays passed through the body P irradiated by the X-ray source 26, and detecting an X-ray image of the body P. The portable housing is formed in a flat plate shape in a size approximately equal to that of a film cassette and IP cassette.

In FIG. 4, the sensor panel 41 includes a TFT active matrix substrate, a gate driver 44, a readout device 46, a controller 47, an A/D converter 48, a memory 49, the radio communication interface 37 and a wired communication interface 50. An active pixel area 43 is disposed on the active matrix substrate. The wired communication interface 50 cooperates with a communication cable for wired communication with the console unit 17. The radio and wired communication interfaces 37 and 50 can be used selectively. A battery (not shown) is contained in the housing for driving various elements in the sensor panel 41.

The active pixel area 43 is defined by an area on the glass substrate. Pixels 42 are arranged in the active pixel area 43 for storing signal charge according to an incident radiation dose of X-rays, and in a matrix form of n rows and m columns in X and Y-directions. The numbers n and m are integers equal to or more than 2, for example, both approximately 2,000. Note that the arrangement of the pixels 42 can be a honeycomb arrangement instead of the rectangular arrangement of the present embodiment. The sensor panel 41 is constituted by a scintillator (not shown) for converting X-rays into visible light. The sensor panel 41 is an indirect conversion type in which visible light from the scintillator is converted photoelectrically by the pixels 42. The scintillator includes phosphor, such as thallium activated cesium iodide (CsI:Tl), and GOS or terbium activated gadolinium oxysulfide ($Gd_2O_2S$:Tb), and is opposed to the entire surface of the active pixel area 43 with the pixels 42. Note that the sensor panel 41 can be a direct conversion type for directly converting X-rays into signal charge, instead of the indirect conversion type.

Each of the pixels 42 includes a photo diode 51 and a thin film transistor 52 (TFT). The photo diode 51 generates charge (electron/hole pair) upon entry of visible light and stores the charge. The thin film transistor 52 is a switching element. The photo diode 51 includes a semiconductor layer of a-Si (amorphous silicon), and upper and lower electrodes between which the semiconductor layer is disposed. The semiconductor layer is a PIN type (p-intrinsic-n type). The lower electrode of the photo diode 51 is connected with the thin film transistor 52. To the upper electrode, bias voltage is applied. An electric field is created in the semiconductor layer by application of the bias voltage. An electron-hole pair is created in the semiconductor layer by the photoelectric conversion. An electron moves to the upper electrode with a positive polarity. The positive hole moves to the lower electrode with a negative polarity, so that the photo diode 51 stores charge by way of a capacitor.

In the thin film transistor 52, a gate electrode is connected to scan lines 53. A source electrode is connected to signal lines 54. A drain electrode is connected to the lower electrode of the photo diode 51. The scan lines 53 and the signal lines 54 are arranged transversely in a quadrilateral form. The number of the scan lines 53 is n or the number of rows of the pixels 42 in the active pixel area 43. The number of the signal lines 54 is m or the number of columns of the pixels 42. The scan lines 53 are connected to the gate driver 44. The signal lines 54 are connected to the readout device 46.

The gate driver 44 drives the thin film transistor 52 while controlled by the controller 47, and causes the sensor panel 41 to operate in functions of the storing, readout and reset. In the storing, signal change according to an incident radiation dose of X-rays is stored in the pixels 42. In the readout, the signal charge in the pixels 42 is read out. In the reset, unwanted charge in the pixels 42 is eliminated. While X-rays are applied, the gate driver 44 turns off the thin film transistor 52 of all the pixels 42, to start the pixels 42 storing the signal charge. After irradiation of the X-rays, gate pulses G1-Gn are input sequentially to the scan lines 53, to turn on the thin film transistor 52 by one pixel row, for reading out the signal charge. The signal charge from the pixels 42 is read out on the signal lines 54, and input to the readout device 46.

The photo diode 51 generates dark current charge irrespective of incidence of X-ray. The dark current charge is a noise component in relation to image data. To remove the dark current charge, reset of pixels is performed before irradiation of X-rays. The reset is operation of sweeping dark current charge at the pixels 42 through the signal lines 54.

The readout device 46 reads the signal charge D1-Dm from the pixels 42. The controller 47 controls various elements in the readout device 46. The A/D converter 48 converts the signal charge into digital data, which is written to the memory 49.

The readout device 46 includes integrating amplifiers and a multiplexer. Each of the integrating amplifiers converts the signal charge read out from the pixels 42 into a voltage signal. The multiplexer sequentially changes over columns of the pixels 42 in the active pixel area, and outputs a voltage signal per one column. In the readout operation, the voltage signal input to the readout device 46 is converted by the A/D converter 48 into digital data, which is written to the memory 49 as digital image data. Also, the image data read from the memory 49 is transmitted by the radio or wired communication interface 37 or 50 to the console unit 17.

In the reset, the thin film transistors 52 of the pixels 42 are sequentially turned on by the unit of a pixel row, to input the dark current charge from the pixels 42 to the readout device 46, in a manner similar to the readout. However, the dark current charge in the reset is abandoned by resetting the integrating amplifiers, and is not output to the A/D converter 48. The reset is started upon powering of the electronic cassette 16, and repeated at a predetermined interval of time. In case the electronic cassette 16 becomes ready for imaging, the reset is interrupted. Shortly before the start of storing in the pixels 42, the reset of one frame is performed for one time.

Also, detection sensors 56 are disposed in the active pixel area 43 in a form included in part of the group of the pixels 42. The detection sensors 56 operate for detecting a start of irradiation of X-rays. The detection sensors 56 have the photo diode 51 similarly to the pixels 42, but do not have the thin film transistor 52. The photo diode 51 and the signal lines 54 are short-circuited. An output of the detection sensors 56 (charge generated by the photo diode 51) is caused to flow to the signal lines 54 irrespective of turn-on or turn-off of the thin film transistor 52 in the pixels 42.

The output of the detection sensors 56 is read out to the memory 49 by the readout device 46 and the A/D converter 48 in a manner similar to the pixels 42. The readout of the detection sensors 56 is performed at such a short period as μsec. An output of the detection sensors 56 obtained by the readout of one event is an incident radiation dose of X-rays per unit time. Upon start of irradiation, the incident radiation dose per unit time gradually increases, to increase the output of the detection sensors 56.

The controller 47 reads out the output at each time that the output of the detection sensors 56 is stored to the memory 49. The controller 47 compares the output of the detection sensors 56 with a predetermined threshold for the start, and judges a start of the irradiation of X-rays in response to becoming of the output as high as the threshold. Thus, the sensor panel 41 can function for detecting the start of irradiation without receiving a sync signal from the X-ray source apparatus 11. Also, the output of the detection sensors 56 can be read out even while the sensor panel 41 operates for the storing. It is also possible to detect termination of irradiation of X-rays by considering the output of the detection sensors 56.

After the power supply for the electronic cassette 16 is turned on, the sensor panel 41 starts the reset of the pixels 42. In case the command from the console unit 17 is received, the sensor panel 41 terminates the reset, and becomes ready. The sensor panel 41 starts detection of irradiation, namely starts readout of an output of the detection sensors 56. Upon detecting the start of irradiation of X-rays, the sensor panel 41 performs the reset of one frame, and turns off the thin film transistor 52 of the pixels 42 to start the storing. In case the start of irradiation is detected, the sensor panel 41 transmits a start flag to the console unit 17 through the radio communication interface 37. The sensor panel 41 continues the readout of the detection sensors 56 even after starting the storing. In case the output of the readout becomes equal to or lower than a second threshold of the termination, the controller 47 detects the termination of irradiation. In response to this, the sensor panel 41 terminates the storing, and starts the readout of an X-ray image. In the present embodiment, the first and second thresholds are used in detecting the start and detecting the termination. The second threshold may be equal to the first, or can be different from the first.

Figure 5:
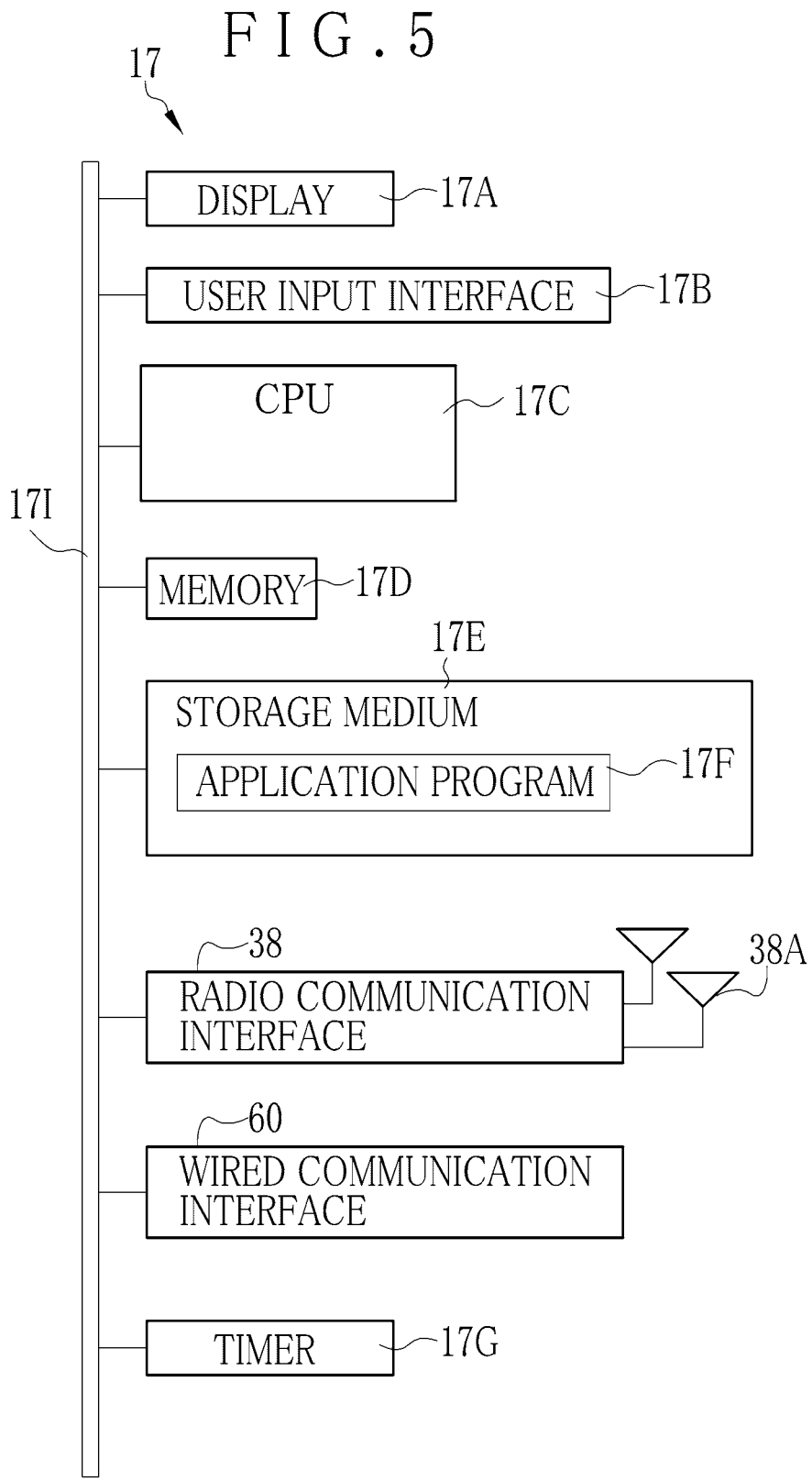
FIG. 5 is a block diagram schematically illustrating a console unit.

In FIG. 5, the console unit 17 is constituted by a computer, a control program such as an operating system (OS), and an application program 17F. The computer is a notebook computer, in which a display device 17A (display panel) is contained in a housing of a computer main unit. The control program and the application program 17F are installed in the computer. The console unit 17 includes the display device 17A, a user input interface 17B, a CPU 17C (controller), a memory 17D, a storage medium 17E, the radio communication interface 38, a wired communication interface 60 and a timer 17G. There is a data bus 17I where those elements are connected with one another.

Examples of the user input interface 17B are a keyboard, mouse and touchscreen device provided together with the display device 17A. The storage medium 17E stores various data, for example, hard disk drive (HDD). The storage medium 17E stores a control program, the application program 17F and other data.

The memory 17D is a working memory with which the CPU 17C performs tasks. The CPU 17C loads the memory 17D with the control program read from the storage medium 17E, and controls various elements in the computer by running the control program. The radio communication interface 38 wirelessly connects with the access point 22 or the wireless access point 36 for radio communication. The wired communication interface 60 is connected by a communication cable to the electronic cassette 16 or the source driver 27 of the medical cart 14 for wired communication. The radio and wired communication interfaces 38 and 60 can be used selectively. The timer 17G is used to measure transmission speed between the electronic cassette 16 and the console unit 17 to be described later in detail.

Figure 6:
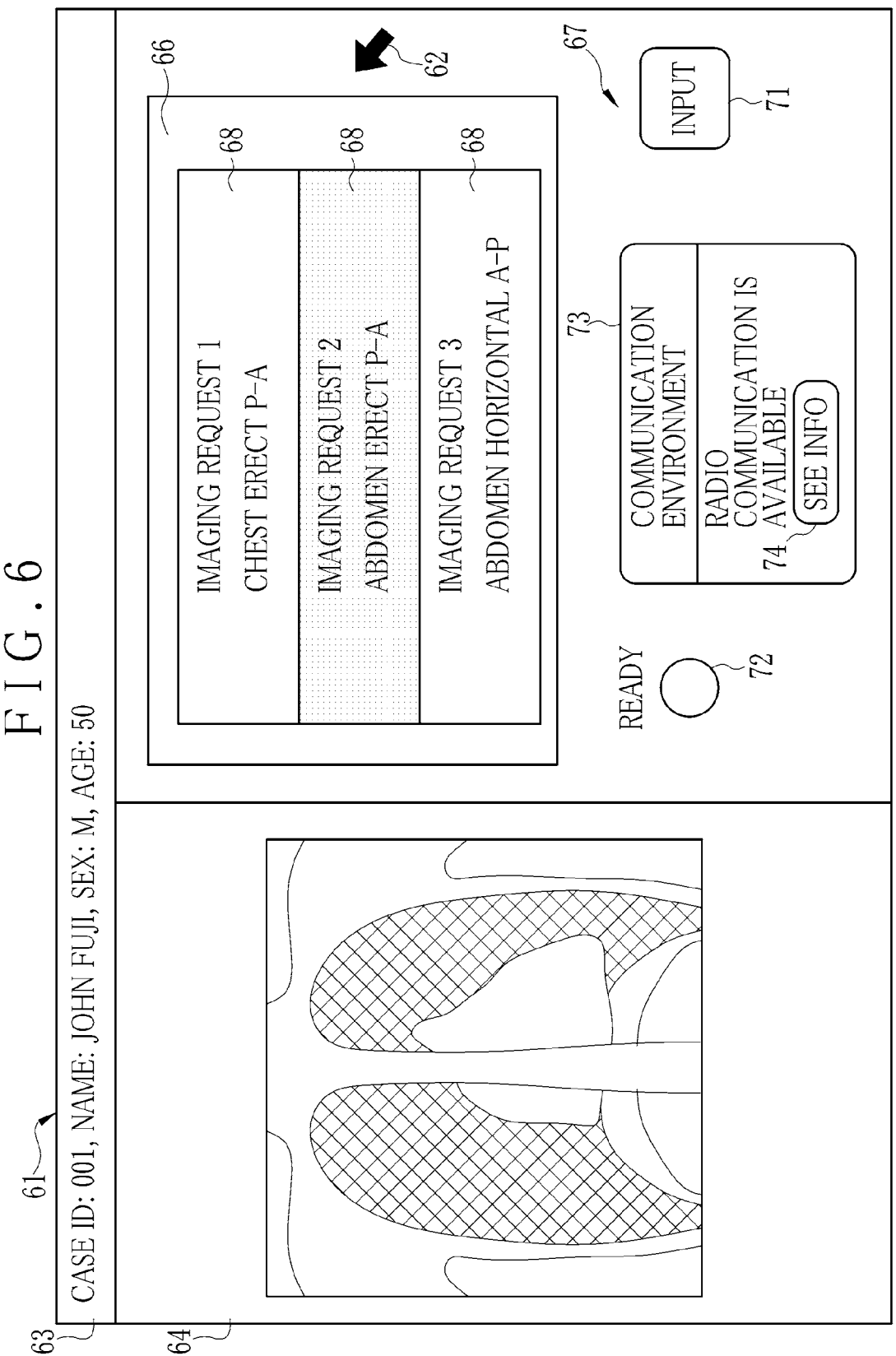
FIG. 6 is a front elevation illustrating a screen of the console unit.

In FIG. 6, an input screen 61 of the GUI (graphical user interface) appears on the display device 17A of the console unit 17 upon running the application program 17F. A pointer 62 is displayed in the input screen 61 for pointing a partial area. An input device is connected to the console unit 17, for manipulating the pointer 62, such as a mouse, trackpad and the like.

The input screen 61 includes an information area 63, an image area 64, a request area 66 and a button area 67. An imaging request 68 received from the RIS server 25B is disposed in the request area 66. In case one of the imaging requests 68 is selected by use of the pointer 62, the imaging request 68 is indicated by a change in the color distinctly from those unselected in the imaging requests 68. Case information of the body is displayed in the information area 63 in connection with the imaging request 68, such as a name, case ID, age and sex of a patient (body).

The image area 64 is for displaying an X-ray image transmitted by the electronic cassette 16 after imaging. In FIG. 6, the X-ray image appears in the image area 64. However, no image appears in the image area 64 before the imaging. It is possible with the image area 64 to check the X-ray image immediately after the imaging. The operator T views the X-ray image in the image area 64, and checks propriety in the imaging. In case the imaging request 68 is selected in the request area 66, an X-ray image corresponding to the imaging request 68 is displayed in the image area 64.

The button area 67 includes an input button 71, a ready indicator 72 and an on-line status area 73. The input button 71 is used for inputting an imaging condition and a setting of various items for the electronic cassette 16. In case the input button 71 is pointed by the pointer 62, a setting screen is caused to appear.

The ready indicator 72 indicates ready information of a ready condition of the electronic cassette 16. In case an operation button (not shown) is pushed in the console unit 17 to transmit a preparation signal for imaging to the electronic cassette 16, the controller 47 in the electronic cassette 16 operates for setting to the ready condition. After the setting to the ready condition, the controller 47 sends an end flag to the console unit 17. The ready indicator 72 is turned on in response to the end flag in the console unit 17. The operator T can be informed of the ready condition of the electronic cassette 16 by the turn-on of the ready indicator 72.

The on-line status area 73 indicates information related to the radio communication environment around the X-ray imaging apparatus 12. As described heretofore, various devices may be disposed in a hospital room with the X-ray imaging apparatus 12, for example, the access point 22, the portable terminal device 23, the electromagnetic medical instrument 24 and the like other than the X-ray imaging apparatus 12. The radio communication environment is changeable with influence of radio waves from the access point 22 or the portable terminal device 23 or electromagnetic waves having electromagnetic noise from the electromagnetic medical instrument 24. According to poor communication environment, radio communication may be impossible with large influence of electromagnetic waves and frequent occurrence of a communication failure, such as a delay and communication error.

As will be described later in detail, the console unit 17 measures the communication environment of the X-ray imaging apparatus 12. The on-line status area 73 displays the measured communication environment from the console unit 17. Message data displayed on the on-line status area 73 is possibility or impossibility of radio communication for transmitting images.

A details button 74 is disposed in the on-line status area 73 for indicating detailed information of the communication environment. "SEE INFO" is indicated in the details button 74 assuming that there is detailed information. "NONE" is indicated in the details button 74 in the case of no detailed information. Pointing the details button 74 causes message screens (FIGS. 22-27) to appear, so that the detailed information can be displayed. In addition, the message screens can be read out at a suitable time point upon measurement of the communication environment, which will be described later in detail.

Figure 7:
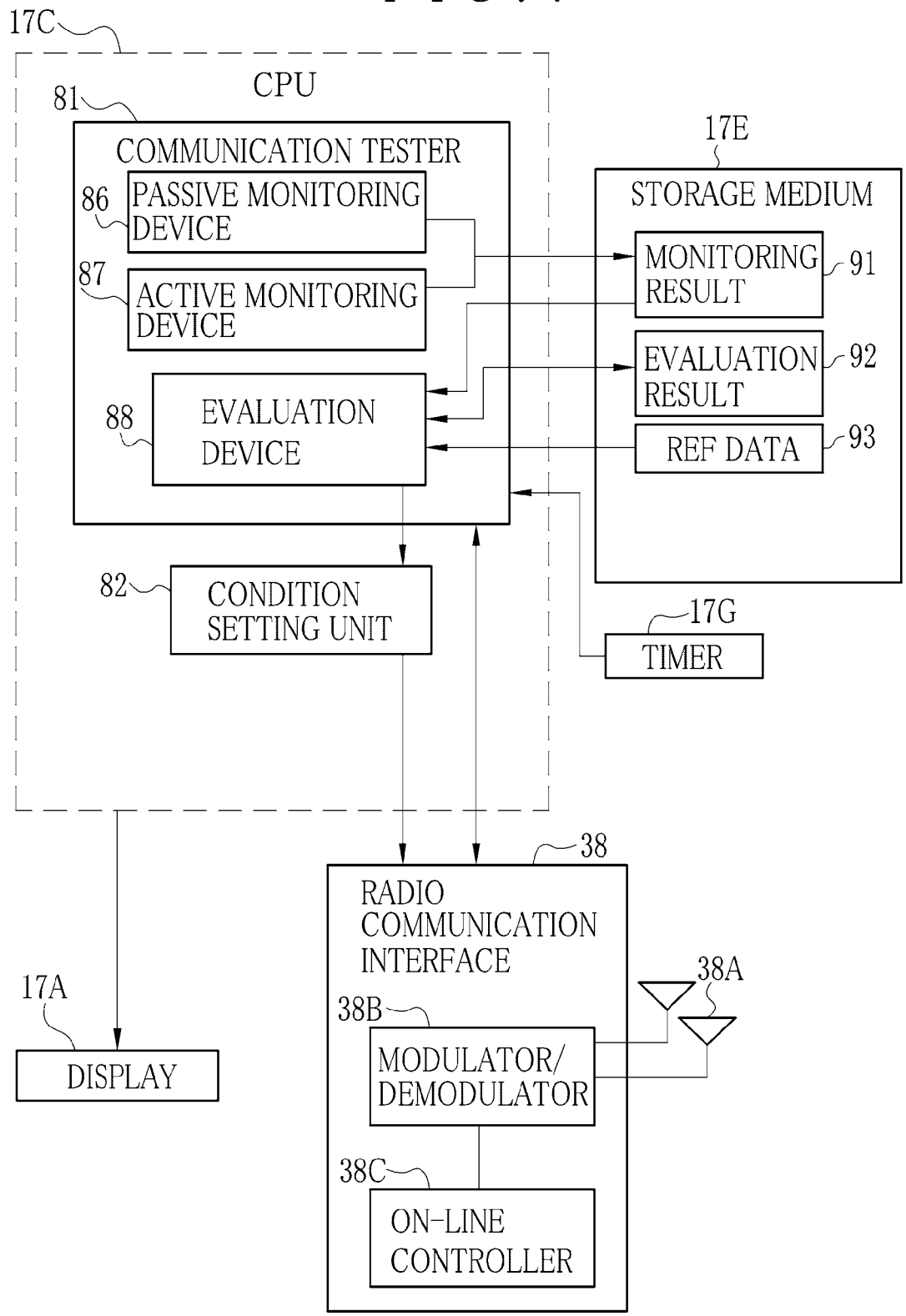
FIG. 7 is a block diagram schematically illustrating the console unit.

In FIG. 7, the CPU 17C of the console unit 17 is caused by running the application program 17F to operate as a controller in cooperation with the memory 17D to control the display device 17A, the storage medium 17E and the like in the console unit 17. Also, a communication tester 81 and a condition setting unit 82 are started up on the CPU 17C.

The communication tester 81 measures the communication environment of the X-ray imaging apparatus 12 by use of the radio communication interface 38. The radio communication interface 38 includes an antenna 38A, a modulator/demodulator 38B and an on-line controller 38C. The antenna 38A transmits and receives a carrier wave for the purpose of radio communication. The modulator/demodulator 38B combines the carrier wave with data to be transmitted by performing modulation, and also acquires data from the carrier wave received through the antenna 38A by performing demodulation.

The on-line controller 38C controls transmission according to a wireless LAN standard. Examples of communication protocols are TCP/IP (Transmission Control Protocol/Internet Protocol) and IEEE 802.11n. The communication protocols are provided in layers according to the model of reference of the OSI (Open Systems Interconnection). The plural communication protocols of different layers are combined together for use. The TCP/IP is used even in the wired LAN, and is a communication protocol of an upper layer in the wireless LAN standard. The IEEE 802.11n is a communication protocol of a layer lower than the TCP/IP, and determines steps of communication particular to the radio communication. It is possible in the IEEE 802.11n to use radio waves of bands of 2.4 GHz or 5 GHz for radio communication channels.

Also, the radio communication interface 37 of the electronic cassette 16 and the wireless access point 36 are constructed in a manner similar to the radio communication interface 38.

The communication tester 81 includes a passive monitoring device 86, an active monitoring device 87 and an evaluation device 88. The communication tester 81 measures the communication environment by the passive monitoring in the passive monitoring device 86 and the active monitoring in the active monitoring device 87. The passive monitoring is a method of measuring the communication environment by receiving ambient electromagnetic waves without emitting radio waves with the radio communication interface 38. The active monitoring is a method of measuring the communication environment by emitting radio waves with the radio communication interface 38. The evaluation device 88 performs an initial evaluation and comprehensive evaluation to be described later, according to results of the passive monitoring in the passive monitoring device 86 and the active monitoring in the active monitoring device 87. The evaluation device 88 estimates causes of a communication failure by the various evaluations.

Figure 8:
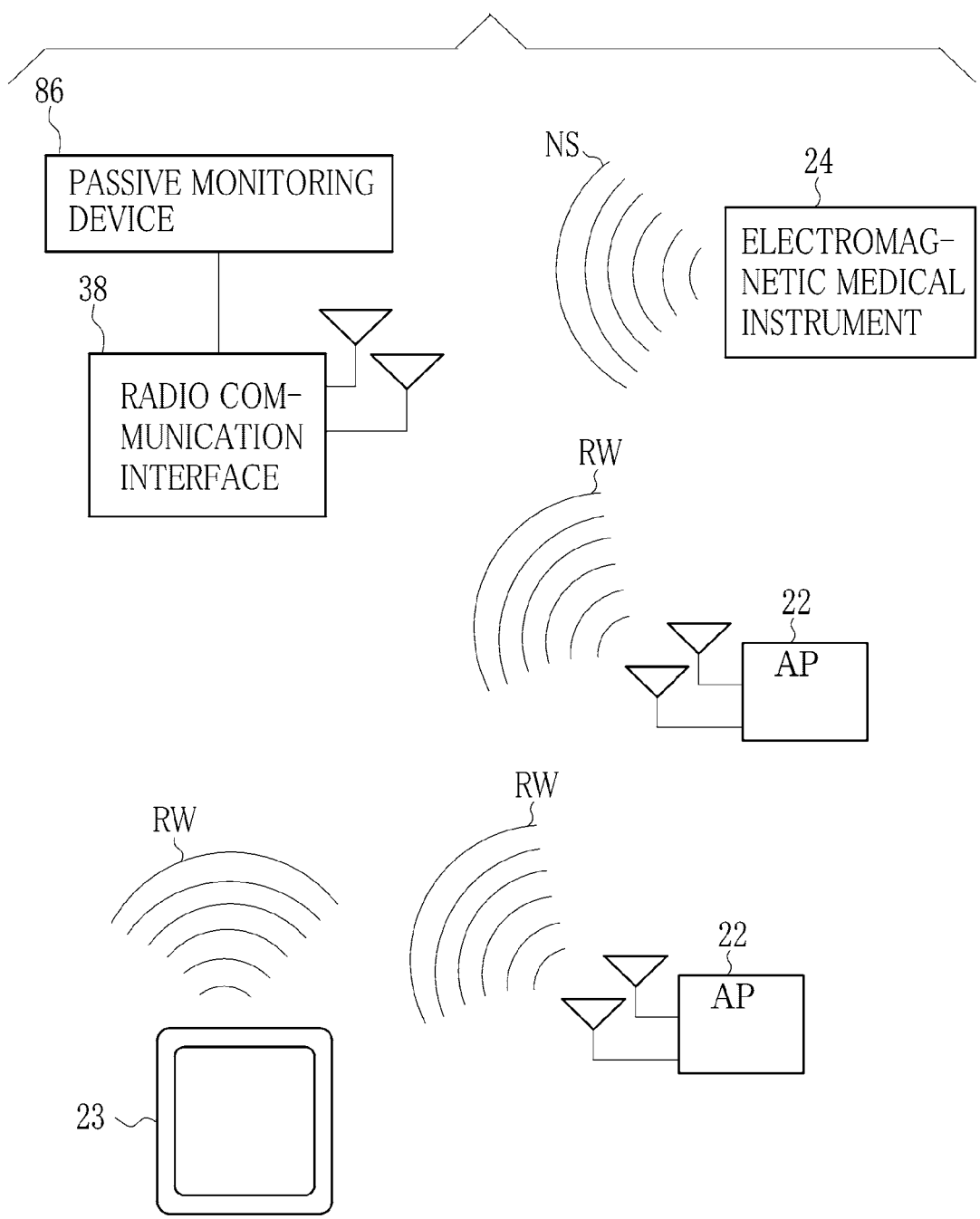
FIG. 8 is a block diagram schematically illustrating passive monitoring.

In FIG. 8, the passive monitoring device 86 measures peripheral communication environment by receiving electromagnetic waves through the radio communication interface 38, the electromagnetic waves including radio waves RW emitted by the portable terminal device 23 or the access point 22 disposed near to the X-ray imaging apparatus 12, and electromagnetic waves including the electromagnetic noise NS created by the electromagnetic medical instrument 24. The communication environment measured by the passive monitoring is occurrence and intensity of electromagnetic waves including the ambient radio waves RW and electromagnetic noise NS. In the present example, spectral intensity of electromagnetic waves with intensity of frequency distribution, and changes of the spectral intensity with time, are measured as illustrated in FIGS. 9-14, according to the received electromagnetic waves. Information of the spectral intensity includes information of a radio communication channel used by the access point 22 or the portable terminal device 23, and information of electromagnetic noise NS created by the electromagnetic medical instrument 24.

Figure 9:
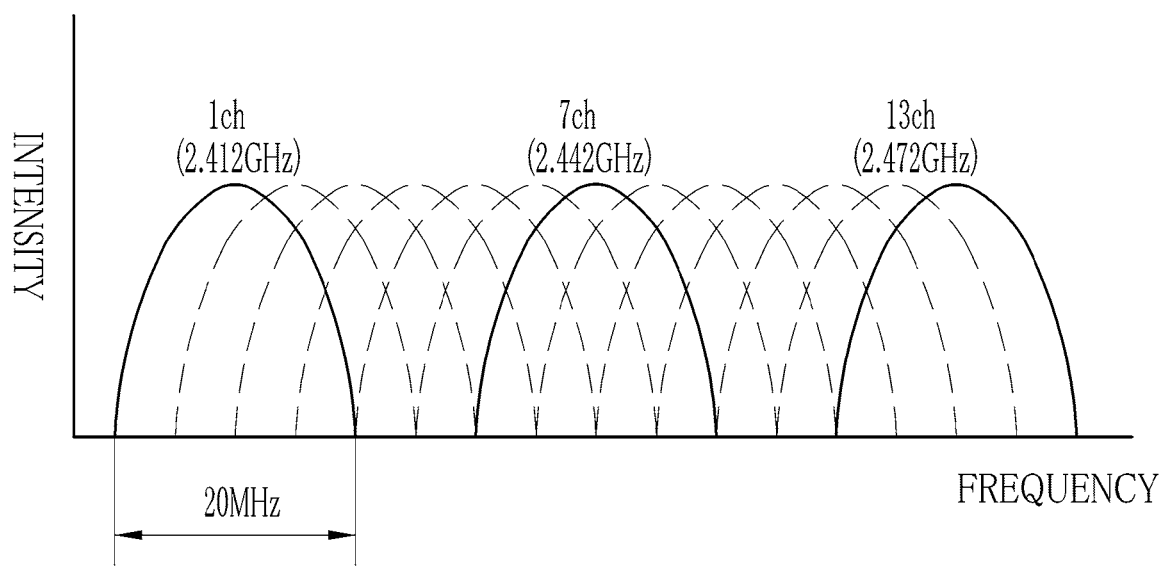
FIG. 9 is a graph illustrating a radio communication channel.

In FIG. 9, the band of 2.4 GHz is used in the IEEE 802.11n standards. The band of 2.4 GHz is divided into plural radio communication channels for use. To be precise, the band of 2.4 GHz is in a range of approximately 2.4-2.5 GHz, which is divided into 1st channel to 13th channel each of which has a width of the band of 20 MHz. As the radio communication channels are arranged at an interval of 5 MHz, frequencies of the four channels adjacent to one another are overlapped on one another. Radio interference occurs upon using the channels of the overlapped frequencies. Thus, the number of the channels available simultaneously in the band of 2.4 GHz is 3 without radio interference. To establish the local area network 21 inclusive of the access point 22, three channels are preferably selected from 1st to 13th channels in view of preventing radio interference. Any one of the three channels is assigned to the access point 22.

The selected three channels are 1st channel (with a center frequency of 2.412 GHz), 7th channel (with a center frequency of 2.442 GHz) and 13th channel (with a center frequency of 2.472 GHz) as indicated by the solid line and in arrangement at an interval of six channels. Assuming that channels are assigned to a plurality of the access points 22 disposed at a small distance, for example, in plural adjacent hospital rooms, it is likely that their ranges of reach of radio waves overlap on one another. Thus, channels of different frequencies are assigned to the access points 22 to avoid crosstalk of frequencies. The access points 22 generate a beacon signal in compliance with the frequencies of the channels.

The beacon signal, for 1st channel, is generated with a frequency in a band width of 2.412 GHz±20 MHz, and for 7th channel, is generated with a frequency in a band width of 2.442 GHz±20 MHz.

Figure 10:
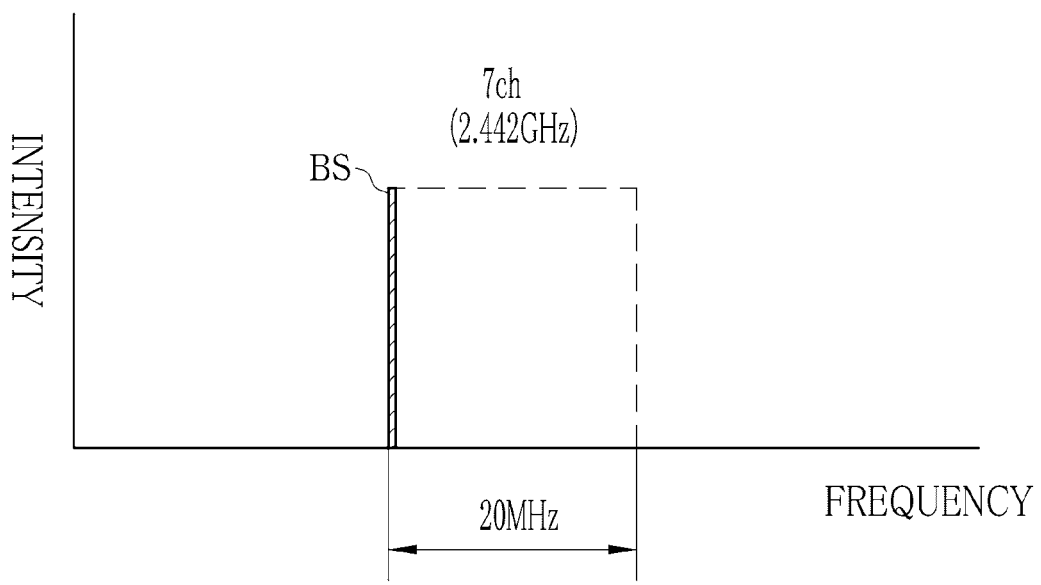
FIG. 10 is a graph illustrating emission of a beacon signal from the radio communication channel.
Figure 11:
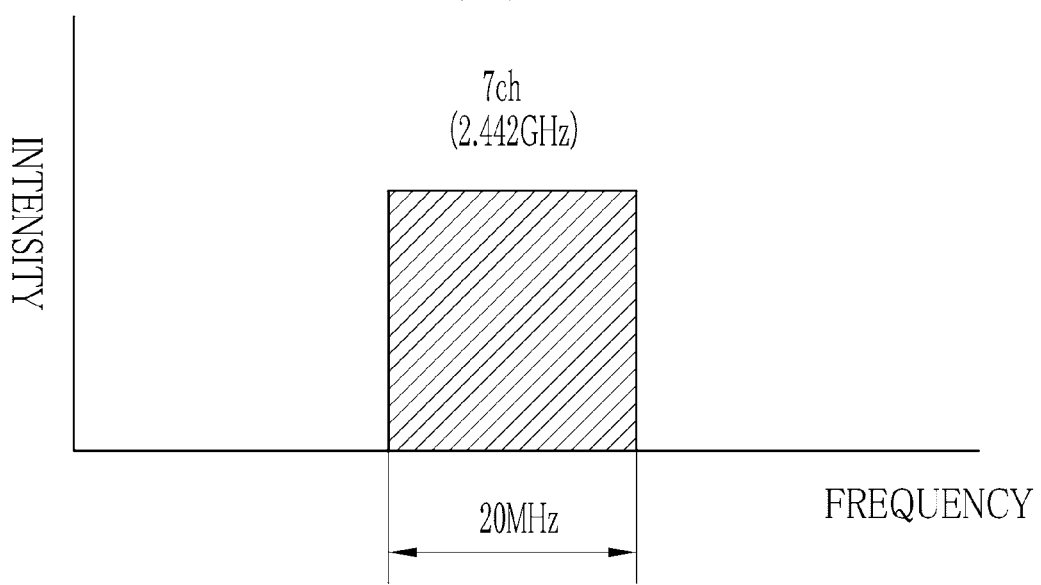
FIG. 11 is a graph illustrating a state of a highest load factor of the radio communication channel.

Also, it is possible to detect the traffic load of each of the channels by checking conditions of using a frequency band of each channel. For example, a communication load of each channel at one instant can be found according to a load factor of the frequency band of each channel. The load factor of the frequency band decreases according to a decrease in the communication load, but increases according to an increase in the communication load. In FIG. 10, the access point 22 is assigned with 7th channel. Assuming that the access point 22 does not communicate with the portable terminal device 23 because of the absence of the portable terminal device 23, then the access point 22 emits only a beacon signal BS periodically. Such a small range as 1 MHz is used in the frequency band (indicated by the broken line) of 20 MHz of one channel. In contrast with this, the access point 22 communicates wirelessly with one or more portable terminal devices 23 in FIG. 11. A load factor of the frequency band is larger. At the largest, the frequency band of 20 MHz is fully used.

Figure 12:
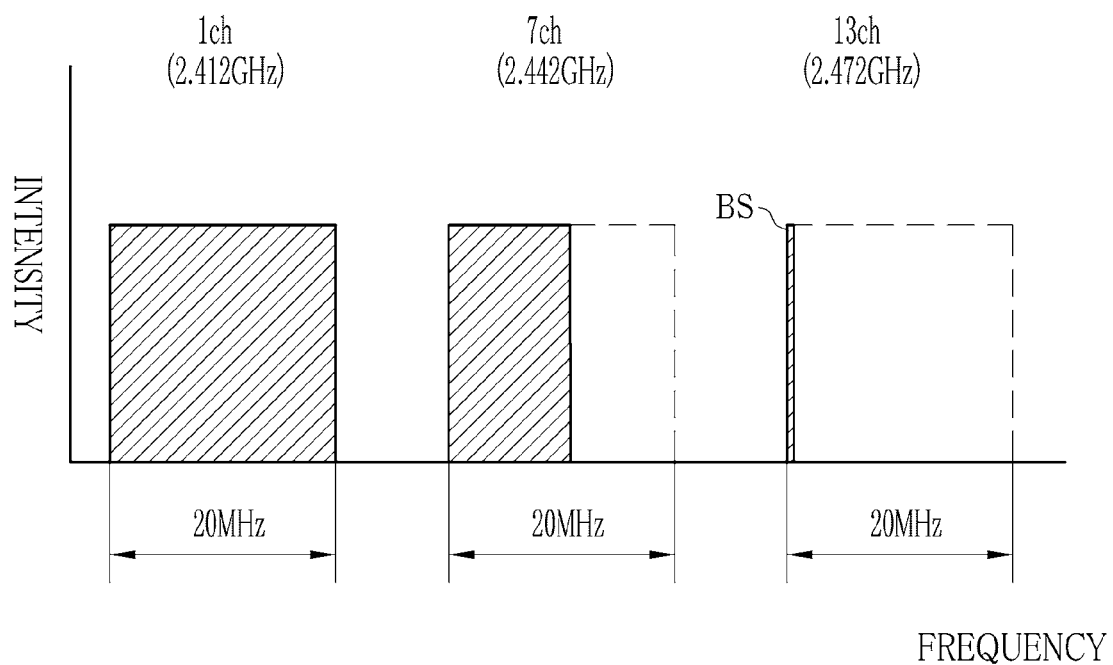
FIG. 12 is a graph illustrating a load factor of each of three channels.

In FIG. 12, a load factor of the band width of 1st channel is the largest (100%). A load factor of the band width of 7th channel is 50%. The band width of 13th channel is used only for transmitting a beacon signal BS. The load factor of the band width of each channel at a certain time point is indicated. In general, the load factor always changes with time. A time profile of the load factor of the band width of each channel is observed, so that it is possible to recognize changes in a communication load of each channel with time, and an average communication load in a certain period of measurement. The traffic load increases according to an increase in the average communication load in a channel, and decreases according to a decrease in the average communication load in a channel.

The band of 2.4 GHz is also referred to as the Industry Science Medical band (ISM band). The use of this band is allowed publicly for the electromagnetic medical instrument 24. Interference with electromagnetic noise from the electromagnetic medical instrument 24 may occur. There are various types of electromagnetic noise from the electromagnetic medical instrument 24 according to types of the instrument.

Figure 13:
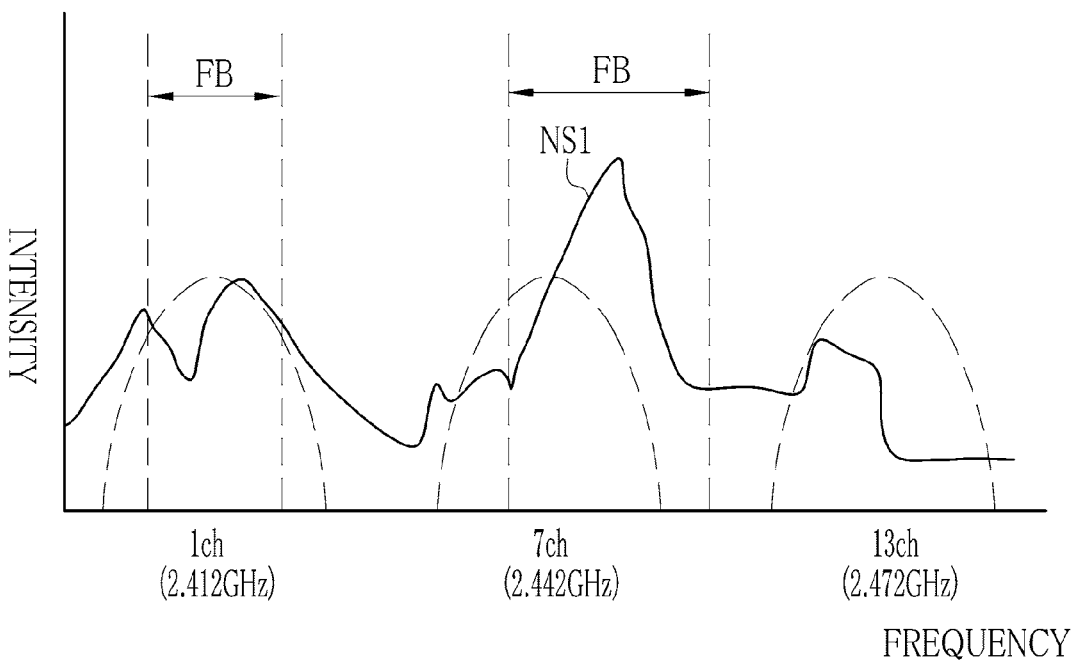
FIG. 13 is a graph illustrating electromagnetic noise.

For example, electromagnetic noise NS1 in FIG. 13 is in a distribution of all the ranges of 1st channel, 7th channel and 13th channel of the radio communication channels. Intensity of the electromagnetic noise NS1 is specially high in a range overlapping on 1st channel and 7th channel. The electromagnetic noise NS1 is in a width FB of changes in which a range with high intensity changes with time. It is impossible simultaneously to use all of 1st channel, 7th channel and 13th channel in a condition with the electromagnetic noise NS1.

Figure 14:
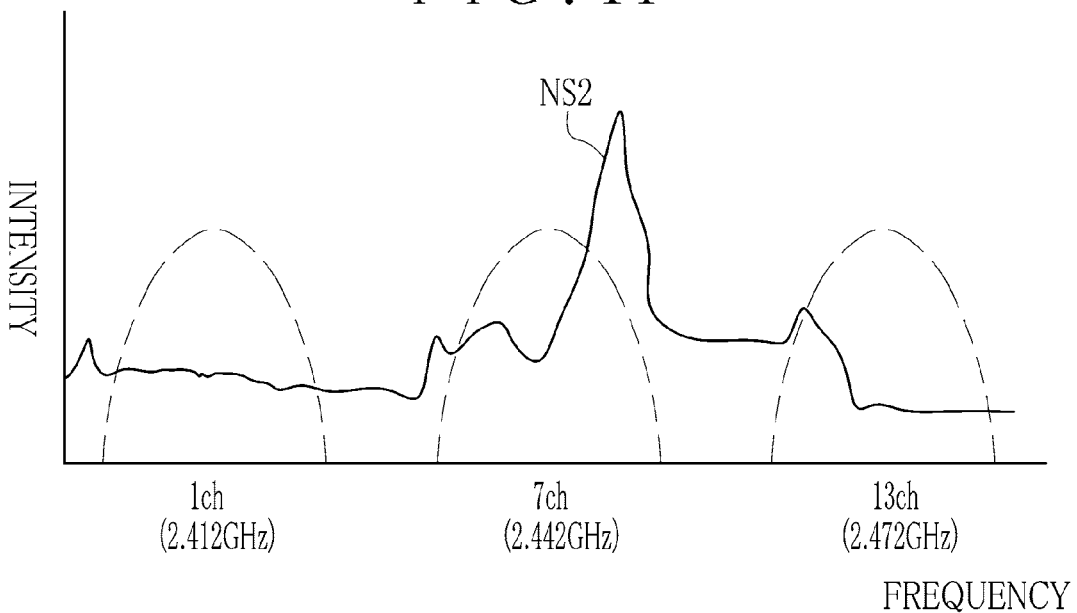
FIG. 14 is a graph illustrating another example of electromagnetic noise.

Intensity of electromagnetic noise NS2 in FIG. 14 is high in an area overlapped on 7th channel. The area of the high intensity of the electromagnetic noise NS2 is constant and does not change with time. While the electromagnetic noise NS2 is generated, it is possible safely to use a radio communication channel by selecting 1st channel or 13th channel without using 7th channel with possible radio interference.

Figure 15:
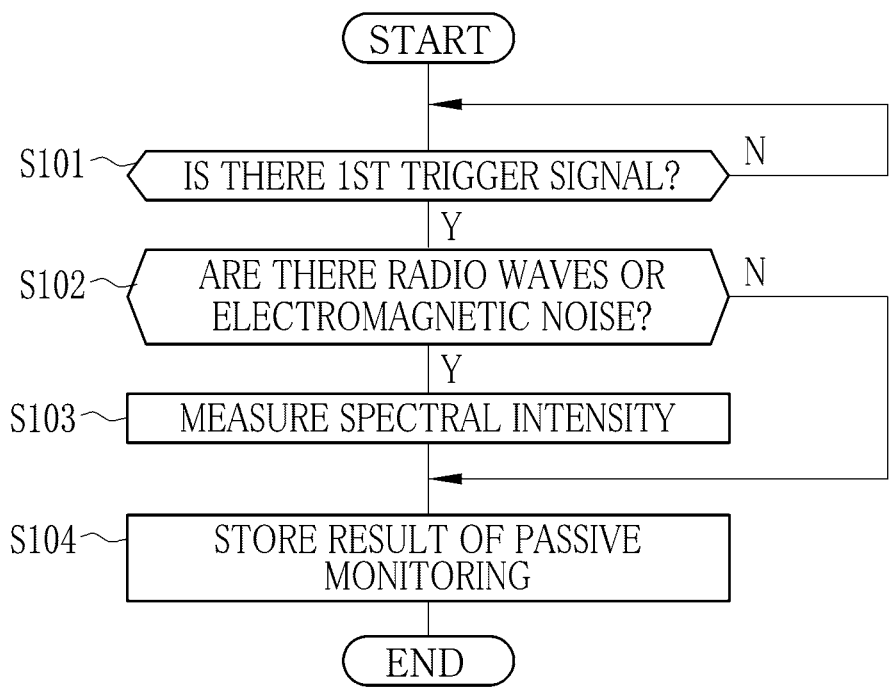
FIG. 15 is a flow chart illustrating passive monitoring.

In FIG. 15, the passive monitoring device 86 being started up is ready to receive a first trigger signal in the step S101. The passive monitoring device 86 starts the passive monitoring in response to the first trigger signal (yes in the step S101). An example of the first trigger signal is the unlock signal from the medical cart 14. See FIG. 3. The CPU 17C, in case the unlock signal is received from the medical cart 14 through the radio communication interface 38, drives the passive monitoring device 86 to start the passive monitoring.

While the medical cart 14 runs, the lock mechanism 33 is engaged. In case the medical cart 14 is entered in a hospital room and stopped for the in-patient care, the lock mechanism 33 is released. The X-ray imaging apparatus 12 enters the hospital room while carried on the medical cart 14. The X-ray source 26 and the electronic cassette 16 are positioned to image an object of interest of the body P before imaging. For the purpose of the positioning, the lock mechanism 33 must be released. In view of those steps before the imaging, the passive monitoring is started in response to receiving the unlock signal in the console unit 17. The passive monitoring can be started in the place of using the X-ray imaging apparatus 12 at a step before the imaging of one event.

The passive monitoring device 86, upon detecting the radio waves RW and electromagnetic noise NS (yes in the step S102), measures spectral intensity of the radio waves RW and electromagnetic noise NS in the step S103 as illustrated in FIGS. 9-14. The passive monitoring is continued for predetermined time to measure changes in the spectral intensity with time. A time profile obtained to express the spectral intensity and its changes with time is stored to the storage medium 17E by way of a result of the passive monitoring, in the step S104. In FIG. 7, the result of the passive monitoring is written as a monitoring result 91 to the storage medium 17E.

Figure 16:
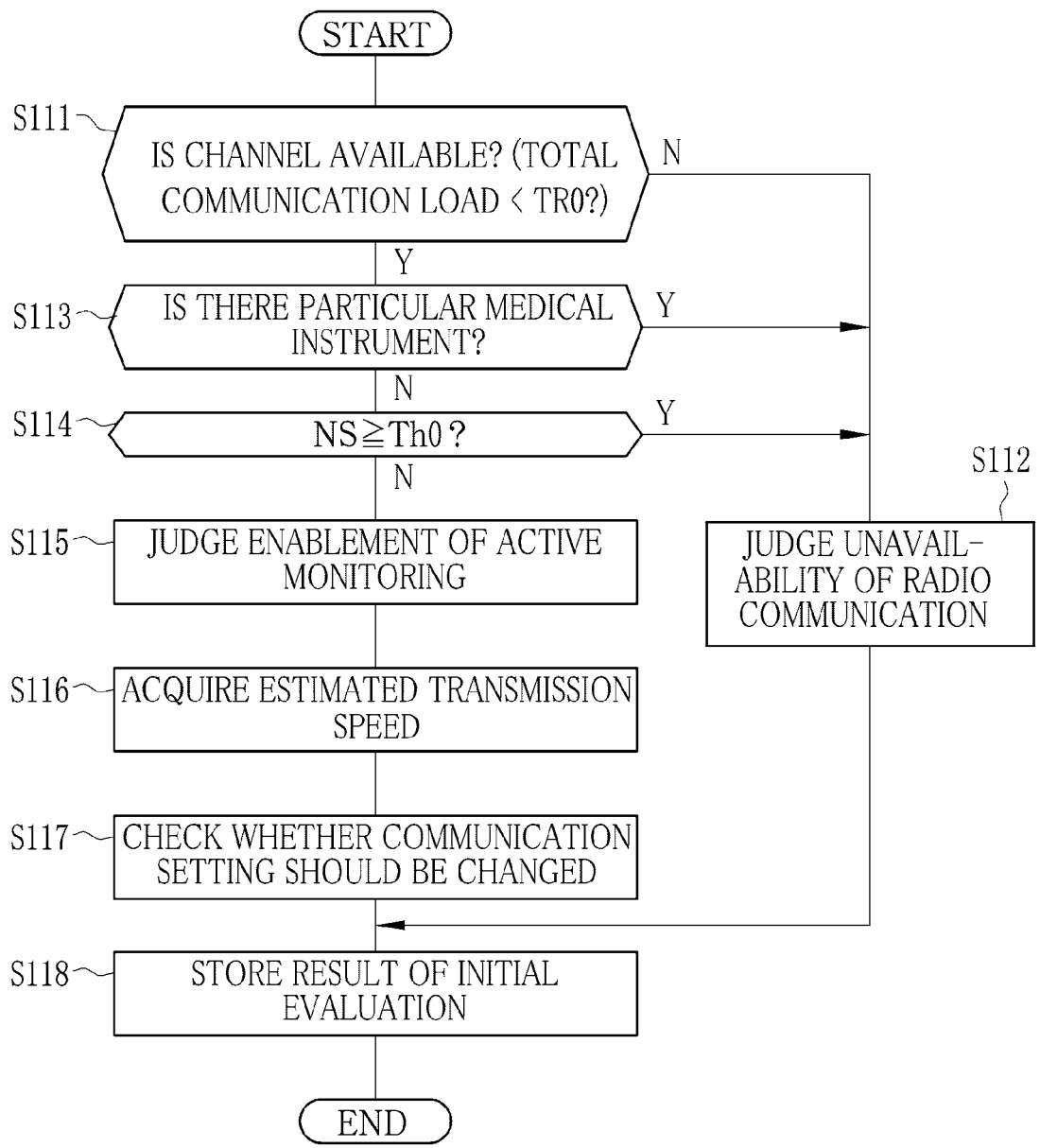
FIG. 16 is a flow chart illustrating an initial evaluation.

In FIG. 16, the evaluation device 88 performs an initial evaluation by reading the monitoring result of the passive monitoring from the storage medium 17E. In the initial evaluation, the evaluation device 88 checks availability of a radio communication channel according to the spectral intensity in the step S111. The spectral intensity being checked at a certain time point, it is possible to detect an unused radio communication channel and communication load (load factor of a band) of each radio communication channel at this time point. Also, checking of the time profile of the spectral intensity makes it possible to detect the traffic load of each radio communication channel as degree of use of the channel. As described heretofore, the traffic load can be recognized by a mean value of the communication load of each radio communication channel in a period of the passive monitoring. Note that the expression of the communication load is hereinafter used to stand for the mean value of the communication load of a radio communication channel in a period of the passive monitoring.

The maximum time of using one radio communication channel is defined by the standards. In case a plurality of the portable terminal devices 23 connect to the access point 22 and use the radio communication channel of an equal frequency, the radio communication channel is shared by the portable terminal device 23 in a time-sharing manner. Even assuming that the communication load of the radio communication channel is large, the radio communication channel can be used. However, assuming that the communication load of the portable terminal device 23 other than the X-ray imaging apparatus 12 is large, available time of the radio communication channel to the X-ray imaging apparatus 12 is decreased, so that the transmission speed decreases. Note that the transmission speed is a data size of data transmissible per unit time, and also referred to as a throughput. Assuming that the data size of the transmitted data is small, influence is small with delay because of the decrease in the transmission speed. However, influence of the decrease in the transmission speed to the time of the image transmission is considerably large owing to the large data size of X-ray images.

Assuming that the communication load of one radio communication channel is equal to or more than the predetermined value TR0, the evaluation device 88 judges that this radio communication channel is unavailable, because longer time than allowed for the image transmission will be required. In case the access point 22 uses 1st channel among the three radio communication channels of FIG. 9, it is possible to select 3rd channel or 7th channel by avoiding 1st channel. However, it is likely that a plurality of the access points 22 are disposed in a hospital room, or that radio waves from the access point 22 of next hospital room comes in. It is likely that the communication load of all the selectable radio communication channels is found to be equal to or more than the predetermined value TR0.

Assuming that the communication load of all the selectable radio communication channels is equal to or more than the predetermined value TR0, then the evaluation device 88 judges unavailability of a radio communication channel (no in the step S111). Impossibility of using the radio communication is detected in the step S112 because of long waiting time for image transmission. Also, the evaluation device 88 interrupts and terminates the initial evaluation. This is because no acceptable result of the active monitoring will be acquired due to a large communication load after judging unavailability of a radio communication channel. An evaluation result 92 of the initial evaluation is stored to the storage medium 17E in the step S118.

Assuming that the evaluation device 88 judges that there is an available radio communication channel (yes in the step S111), then the evaluation device 88 checks whether the particular medical instrument 30 of FIG. 1 is present locally around the X-ray imaging apparatus 12 in the step S113. The particular medical instrument 30 is used for diagnosis or treatment of the body P, and may influence its operation assuming that a malfunction occurs. It is necessary to stop the use of radio waves with the X-ray imaging apparatus 12 should an error occur in the operation of the particular medical instrument 30 due to radio waves from the X-ray imaging apparatus 12.

Reference data 93 are stored in the storage medium 17E and referred to by the evaluation device 88 for the evaluation. Waveform data of electromagnetic waves from the particular medical instrument 30 are included in the reference data 93. In the step S113, the evaluation device 88 compares the spectral intensity measured by the passive monitoring with the waveform data, and checks whether the particular medical instrument 30 is present locally within a small distance. Assuming that it is judged that the particular medical instrument 30 is present (yes in the step S113), impossibility in using the radio communication is detected in the step S112. Also, the active monitoring is disabled, because the active monitoring with radio waves is likely to influence the particular medical instrument 30. In the presence of the particular medical instrument 30, the evaluation device 88 controls for storing a result of the initial evaluation in the step S118, and terminates the initial evaluation.

Assuming that it is judged that the particular medical instrument 30 is not present (no in the step S113), then the evaluation device 88 checks whether the level of the electromagnetic noise NS is equal to or more than the threshold Th0 in the band overlapped on the available radio communication channel, in the step S114. An example of the threshold Th0 is a critical value of the electromagnetic noise NS with intolerably large influence to image transmission. In the case of the electromagnetic noise NS1 of FIG. 13, intensity of the electromagnetic noise NS of the frequency band of all the radio communication channels, and is equal to or more than the threshold Th0. The intensity of the electromagnetic noise NS2 of FIG. 14 is equal to or more than the threshold Th0 in the band of 7th channel, but less than the threshold Th0 in the bands of 1st and 3rd channels.

Assuming that it is judged that the electromagnetic noise NS of interference with an available radio communication channel is equal to or more than the threshold Th0 (yes in the step S114), then the evaluation device 88 judges unavailability of radio communication in the step S112. As the active monitoring is impossible in this environment, the evaluation device 88 judges impossibility of the active monitoring. A result of the initial evaluation is stored, so that the initial evaluation is terminated in the step S118.

Assuming that the electromagnetic noise NS is found to be lower than the threshold Th0 (no in the step S114), the evaluation device 88 enables operation of the active monitoring in the step S115. According to the spectral intensity, the evaluation device 88 checks strength of radio waves of available radio communication channels, and estimates transmission speed according to the strength in the step S116. Then the evaluation device 88 checks whether a change in the setting of the radio communication is required for the image transmission in the step S117, controls for storing a result of an initial evaluation in the step S118, and terminates the initial evaluation.

In FIG. 7, the condition setting unit 82 changes the communication setting of the radio communication interface 38, and also sends a command signal to the control interface unit 18 and the electronic cassette 16 to change their communication setting. The communication setting is a condition setting of a radio communication, for example, frequency of a radio communication channel, a packet size in the data transmission, a time-out value and the like. Assuming that the frequency of the radio communication channel initially set in the wireless access point 36 is different from that of a radio communication channel found to be available in the initial evaluation, then the frequency of the radio communication channel is changed.

For the data transmission, data of X-ray images are divided into packets as units. A data size of data to be included in one packet increases according to an increase in a packet size of each one of the packets. An error correction code of the packet is set on a side of a transmitter, and transmitted to a receiver. The receiver checks whether there is a bit error in the data according to the error correction code. Examples of the error correction code are a Cyclic Redundancy Check code (CRC code) and a Frame Check Sequence code (FCS code). A bit error is likely to occur with influence of radio interference according to largeness of the packet size. The bit error is one of causes of delay in the communication, as the packet of occurrence of the bit error must be resent. Therefore, the condition setting unit 82 decreases the packet size upon the transmission of X-ray images in relation to a relatively large intensity of the electromagnetic noise NS even in case the electromagnetic noise NS is less than the threshold Th0. This is effective in reducing the bit error.

The time-out value is tolerable time for checking whether a transmitter of a packet requires resending of a packet or not. The transmitter after the transmission measures time until reception of a response to the reception from the receiver. Assuming that no response occurs even upon exceeding the time-out value, the transmitter of the packet processes the resending of the packet. Assuming that the communication load is large, delay is likely to occur in the communication, to extend the time until the occurrence of the response. Therefore, the condition setting unit 82 sets the time-out value at along level by considering possible delay typically in case the communication load of the available radio communication channel is comparably large. Thus, it is possible to prevent extension of time of the image transmission by the resending of the packet.

Figure 17:
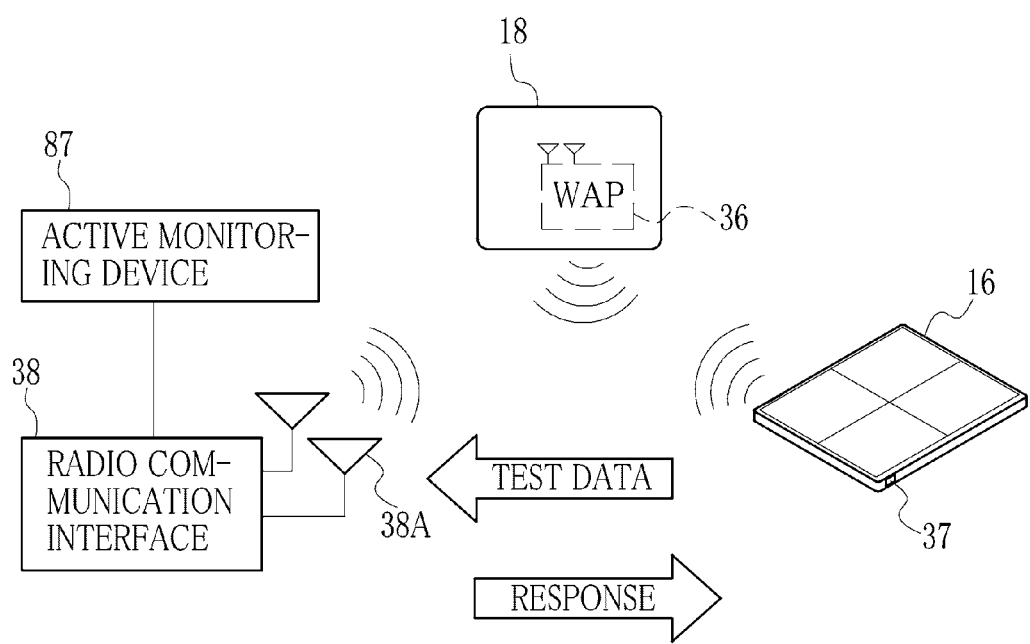
FIG. 17 is an explanatory view illustrating active monitoring.

Assuming that it is judged that the active monitoring is possible in the initial evaluation, the active monitoring is performed. See FIG. 17. The communication environment measured by the active monitoring is a transmission speed and error occurrence information of a communication error created by the bit error. The transmission speed is a data size transmittable per unit time. The error occurrence information of the communication error is a number of events of the communication error and an occurrence ratio of the communication error. To be precise, the error occurrence information is information related to frequency of occurrence of the communication error, for example, number of events of the communication error per unit time, a ratio of the number of events of the communication error to the data size. The transmission speed decreases according to the number of events or occurrence ratio of the communication error. The error occurrence information is a factor determining the transmission speed.

An example in which only a transmission speed is measured is described at first. The active monitoring device 87 causes the radio communication interface 38 and the electronic cassette 16 to transmit test data to one another, to measure the transmission speed. The active monitoring is performed in the same state as image transmission of an X-ray image, for example, in relation to the communication setting of the communication condition, a relative position of the electronic cassette 16 and the console unit 17, and the like. The communication path of the test data is constituted by the wireless access point 36 in the control interface unit 18. A direction of transmitting the test data is from the electronic cassette 16 to the console unit 17. A response to the test data is transmitted by the console unit 17 to the electronic cassette 16. The active monitoring device 87 instructs the electronic cassette 16 to start transmitting the test data by use of the radio communication interface 38. The timer 17G is driven by the active monitoring device 87 to measure elapsed time until finish of receiving the test data. As a data size of the test data is predetermined, a measured transmission speed can be obtained by use of the elapsed time from the instruction of the start of the transmission until the finish of the reception.

The transmission speed is influenced by radio interference, and also by a relative position between the electronic cassette 16 and the console unit 17 and the control interface unit 18 with the wireless access point 36 in relation to directivity of radio waves from the radio communication interface 37 of the electronic cassette 16. Also, the transmission speed is influenced by a blocking object blocking ambient radio waves around the X-ray imaging apparatus 12. Assuming that a baggage or the like of the patient of the body P in the hospital room blocks radio waves, the transmission speed may be changed by the baggage in the presence between the electronic cassette 16 and the control interface unit 18 and the console unit 17. Various objects having property of blocking radio waves may change the transmission speed, for example, a wall of a hospital room near to the X-ray imaging apparatus 12, and furniture, such as a room table and locker associated with the hospital room.

Figure 18:
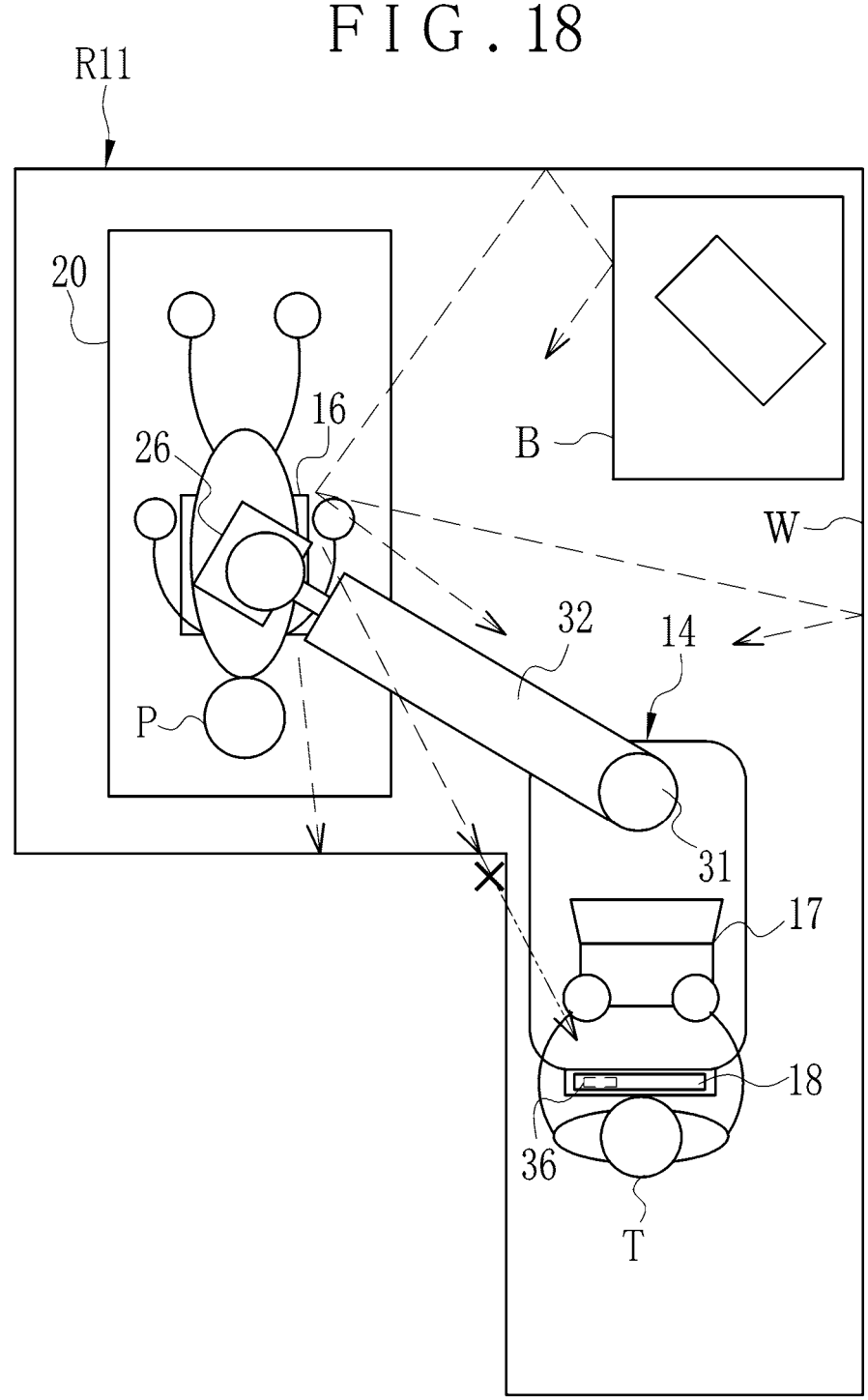
FIG. 18 is a plan illustrating multi-path phasing (MPP)

In FIG. 18, the hospital room R11 is in an L-shape as viewed in a plan. A wall W and the room table B may block radio waves, so that a transmission speed is considerably decreased between the electronic cassette 16 and the console unit 17 by influence. In FIG. 18, an entrance of the hospital room R11 is narrow. An inner space for the hospital bed 20 is wider. It is likely that the medical cart 14 cannot be moved near to the hospital bed 20 with the electronic cassette 16, and should be set near to the entrance, because of the presence of the room table B.

There are plural transmission paths of transmitting radio waves from the electronic cassette 16 as indicated by the broken line. The transmission paths include a direct transmission path of linear travel to reach the control interface unit 18 and the console unit 17, and a reflection path to reach them after plural events of reflection on surfaces of objects, such as the wall W or room table B. A phase shift occurs between radio waves of the reach by passing the plural transmission paths with different distances. The phase shift creates interference between the radio waves, to create a phenomenon of a large change in the strength of received radio waves. This phenomenon is referred to as multi-path phasing (MPP).

In FIG. 18, the hospital room has an L-shape including a narrow portion. The number of walls of the hospital room is higher than that of a simply quadrilateral room, so that the number of paths is higher according to complexity of the shape. It is likely as indicated by "x" that a direct travel path from the electronic cassette 16 to the wireless access point 36 in the control interface unit 18 is intercepted. Influence of the multi-path phasing may be larger. A communication error occurs to decrease the transmission speed.

Figure 19:
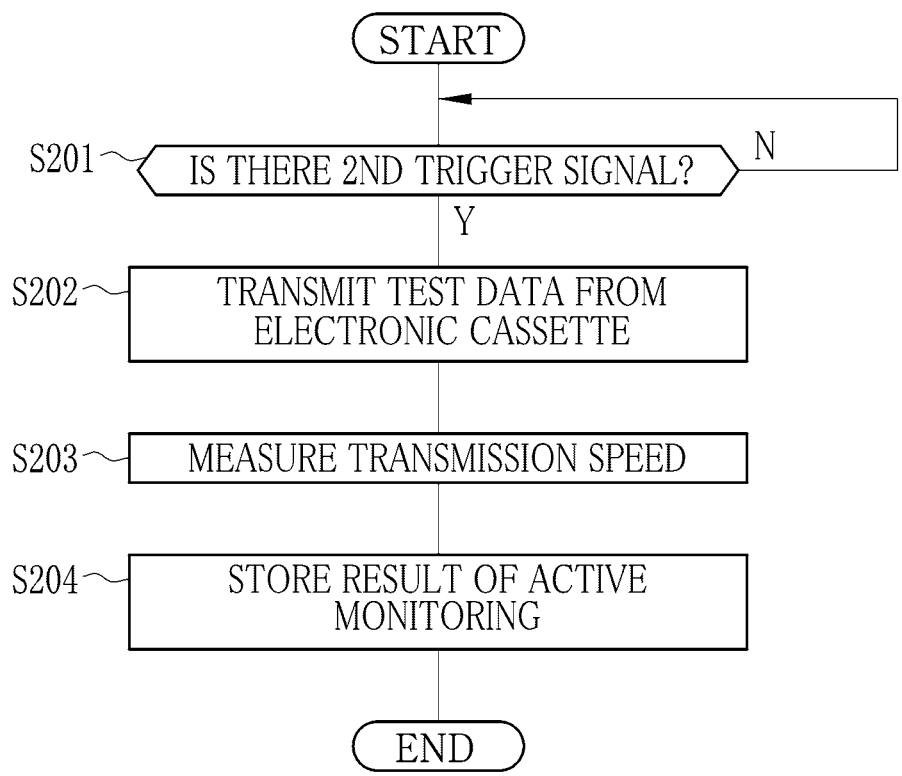
FIG. 19 is a flowchart illustrating the active monitoring.

In FIG. 19, the active monitoring device 87 is ready to receive a second trigger signal in the step S201, and starts the active monitoring in response to the second trigger signal (yes in the step S201). An example of the second trigger signal is one generated by the CPU 17C in case the imaging condition is set in the console unit 17. As the transmission speed is influenced by a blocking object or relative positions of the electronic cassette 16, the wireless access point 36 and the console unit 17, it is preferable to perform the active monitoring in a condition of actual image transmission.

In general, setting of the imaging condition is carried out after positioning the electronic cassette 16 in relation to the object of interest of the body P. Thus, the active monitoring is started upon setting the imaging condition so that the transmission speed can be measured in an actual state of the image transmission.

The active monitoring device 87, upon receiving an input of the second trigger signal, starts the electronic cassette 16 transmitting test data in the step S202, and measures the transmission speed in the step S203. The measured transmission speed is stored as a result of the active monitoring in the step S204. The result of the active monitoring is stored in the storage medium 17E as the monitoring result 91 in a manner similar to the result of the passive monitoring.

Figure 20:
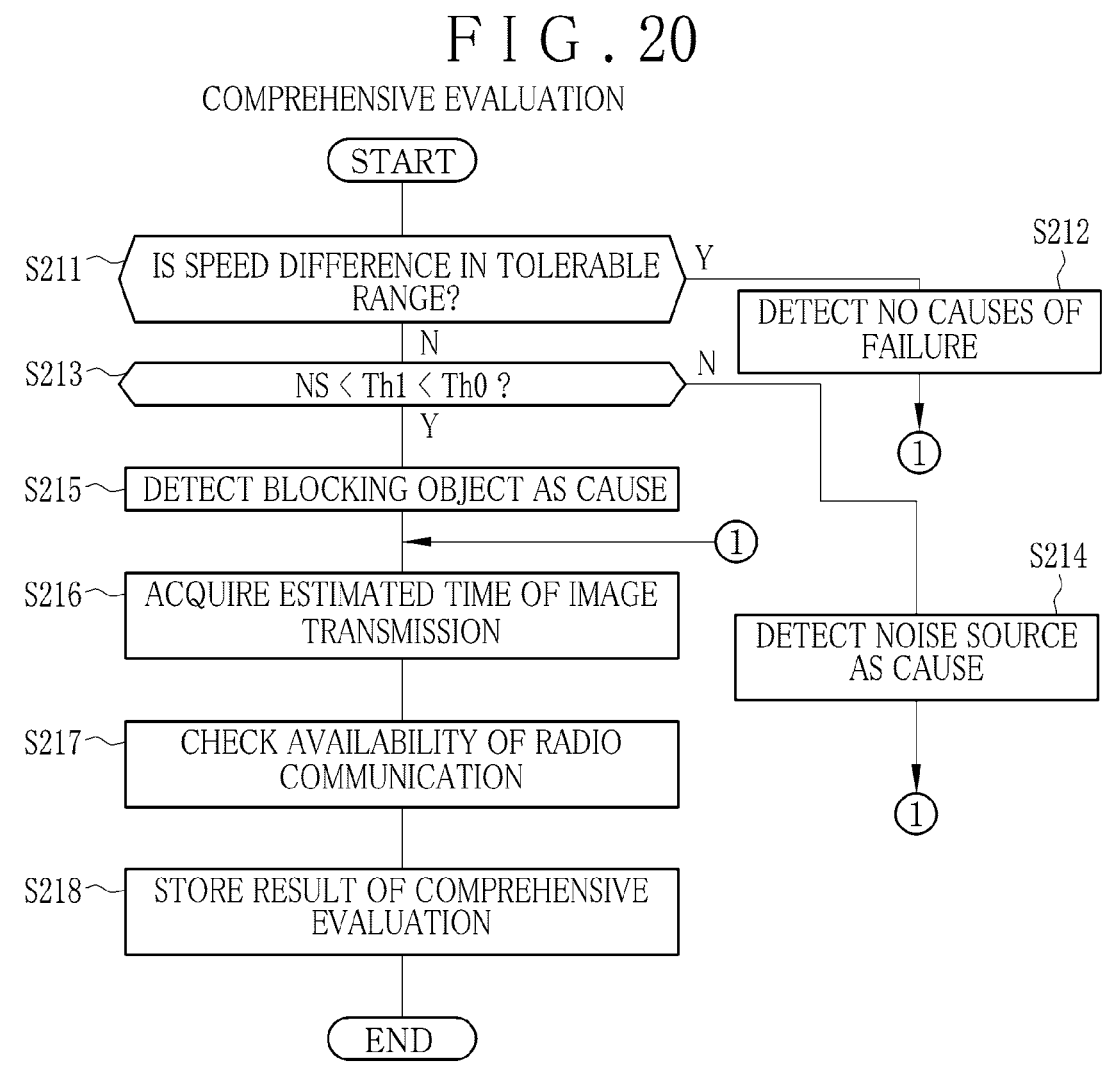
FIG. 20 is a flow chart illustrating comprehensive evaluation.

In FIG. 20, the evaluation device 88 operates after the active monitoring, and performs the comprehensive evaluation in which results of the passive monitoring, the initial evaluation and the active monitoring are considered. At first, the evaluation device 88 obtains a speed difference between an estimated speed of the transmission speed acquired from the passive monitoring and a measured speed of the transmission speed measured by the active monitoring, and checks whether the speed difference is in a tolerable range in the step S211. As the estimated speed is a value after considering influence of ambient radio waves and electromagnetic noise, the estimated speed is a good speed on a condition without influence of electromagnetic noise. The measured speed is a value with components of electromagnetic noise and also influence of a blocking object and a relative position inside the X-ray imaging apparatus 12. Assuming that the relative position is inappropriate or in the presence of a blocking object with influence, then the measured speed is considerably smaller than the estimated speed even without influence of electromagnetic noise. In contrast, the measured speed is likely to be as high as the estimated speed on a condition of propriety of the relative position and without influence of a blocking object.

Assuming that the speed difference between the estimated and measured speeds is within the tolerable range (yes in the step S211), the evaluation device 88 judges that there is no cause of the communication failure in the peripheral communication environment in the step S212. Assuming that the speed difference is not within the tolerable range (no in the step S211) owing to the estimated speed lower than the measured speed, then the evaluation device 88 checks a level of the electromagnetic noise NS.

In the initial evaluation, the electromagnetic noise NS is found to be less than the threshold Th0. In the comprehensive evaluation, it is checked whether the electromagnetic noise NS is less than the threshold Th1 in the step S213, the threshold Th1 being less than the threshold Th0. This is for the purpose of checking whether a cause of the speed difference is influence of the electromagnetic noise NS. Assuming that it is detected that the electromagnetic noise NS is equal to or more than the threshold Th1 (no in the step S213), the evaluation device 88 judges that a communication failure creating the speed difference is caused by a noise source of the electromagnetic noise NS in the step S214.

Assuming that the electromagnetic noise NS is found to be lower than the threshold Th1 (yes in the step S213), the evaluation device 88 judges that the communication failure for the speed difference is caused not by the electromagnetic noise NS but by a relative position of the X-ray imaging apparatus 12 or blocking object (obstacle) in the step S215. After detecting the cause of the communication failure, the evaluation device 88 estimates time required for transmitting an X-ray image in the step S216. As the data size of the X-ray image is easily estimated, the estimated time of the transmission can be determined according to the transmission speed.

The evaluation device 88 carries out final evaluation as to enabling or disabling the radio communication of transmission of an X-ray image (availability) in the step S217. Even on a condition of influence of a blocking object or noise source, the image transmission is enabled assuming that the transmission speed is equal to or higher than a predetermined reference speed, and disabled assuming that the transmission speed is lower than the reference speed. The evaluation device 88 controls for storing a result of the comprehensive evaluation inclusive of detection of the communication failure and possibility of the radio transmission. A result of the comprehensive evaluation is stored in the storage medium 17E as the evaluation result 92 in a manner similar to the result of the initial evaluation.

The operation of the above-described construction is described now by referring to a flow chart of FIG. 21, Table 1 below, and message screens according to FIGS. 22-27.

Figure 21:
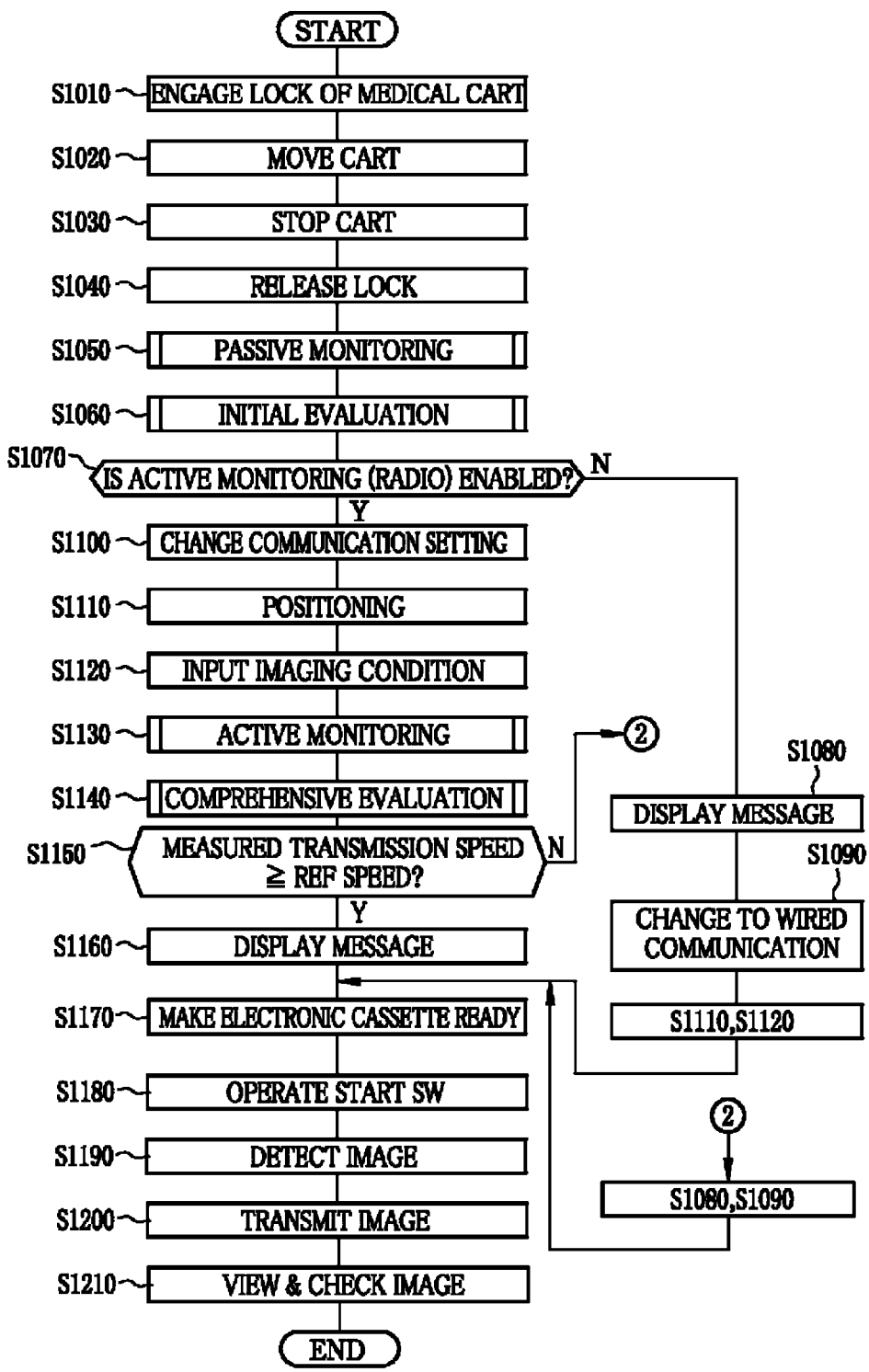
FIG. 21 is a flow chart illustrating steps of imaging in the in-patient care.

In FIG. 21, the operator T comes in the storage space 15 of FIG. 1 at first for imaging in the in-patient care, and places the X-ray imaging apparatus 12 on the medical cart 14, inclusive of the electronic cassette 16, the console unit 17 and the control interface unit 18. The console unit 17 is started up. A communication cable is used to couple the console unit 17 to the LAN interface port 15a connectively. The console unit 17 accesses the RIS server 25B through the LAN interface port 15a and the local area network 21, and acquires an imaging request.

The operator T observes the position of the lock button 34 of FIG. 2 before starting running the medical cart 14, and confirms the engaged state of the lock mechanism 33 so as to prevent accidental shift of the X-ray source 26 during the movement. Assuming that the lock mechanism 33 is not engaged, he or she manipulates the lock button 34 for engagement in the step S1010. The medical cart 14 is moved from the storage space 15 toward rooms in the hospital facility 19.

The operator T reaches the hospital room R11 for the in-patient care, and moves the medical cart 14 into the room manually in the step S1020. Then the medical cart 14 is suitably set for positioning the X-ray source 26 in relation to the body P of the patient in the step S1030. Then preparatory control is performed. At first, the lock mechanism 33 of the medical cart 14 is released in the step S1040. The lock mechanism 33 outputs an unlock signal, which is input to the source driver 27 in the medical cart 14. Also, the unlock signal is transmitted to the console unit 17 through the wired communication interface 29 of the source driver 27. See FIG. 3.

In case the CPU 17C (controller) in the console unit 17 receives the unlock signal, the CPU 17C inputs a first trigger signal to the passive monitoring device 86 according to the unlock signal. The passive monitoring device 86 upon receiving the first trigger signal starts the passive monitoring of FIG. 15 in the step S1050. In the passive monitoring, the passive monitoring device 86 measures spectral intensity of electromagnetic waves, including radio waves RW and electromagnetic noise NS created by the access point 22, the portable terminal device 23 and the electromagnetic medical instrument 24 (circuit apparatus). Upon terminating the passive monitoring, the evaluation device 88 carries out the initial evaluation of FIG. 16 according to results of the passive monitoring in the step S1060.

TABLE 1

|  |  | Example pattern 1 | Example pattern 2 | Example pattern 3 |
|---|---|---|---|---|
| Passive monitoring |  | Spectral intensity of electromagnetic waves | | |
| Initial evaluation | Availability of channel | No | Yes | Yes |
|  | Presence of particular medical instrument | — | Yes | No |
|  | Level of electro-magnetic noise NS | — | — | NS ≥ Th0 (high) |
|  | Enablement of active monitoring | No | No | No |
|  | Estimated transmission speed | — | — | — |
| Active monitoring | Measured transmission speed | — | — | — |
| Comprehensive evaluation | Cause of communication failure | High traffic load | Particular medical instrument | Noise source |
|  | Availability of radio communication for image | No | No | No |
|  | Message | Wait or recommend wired communication | Recommend wired communication | Wait or recommend wired communication |

|  |  | Example pattern 4 | Example pattern 5 | Example pattern 6 |
|---|---|---|---|---|
| Passive monitoring |  | Spectral intensity of electromagnetic waves | | |
| Initial evaluation | Availability of channel | Yes | Yes | Yes |
|  | Presence of particular medical instrument | No | No | No |
|  | Level of electro-magnetic noise NS | Th1 ≤ NS < Th0 (medium) | NS < Th1 < Th0 (low) | NS < Th1 < Th0 (low) |
|  | Enablement of active monitoring | Yes | Yes | Yes |
|  | Estimated transmission speed | 40 Mbps | 50 Mbps | 50 Mbps |

TABLE 1-continued

| | | 30 Mbps | 50 Mbps | 8 Mbps |
|---|---|---|---|---|
| Active monitoring | Measured transmission speed | 30 Mbps | 50 Mbps | 8 Mbps |
| Comprehensive evaluation | Cause of communication failure | Noise source | No cause of failure | Blocking object |
| | Availability of radio communication for image | Yes, rather low speed | Yes, good | Yes or no, low speed |
| | Message | Estimated time | Estimated time | Estimated time & recommend wired communication as per speed |

In Table 1, the evaluation device 88 in the initial evaluation checks various statuses according to the result of the passive monitoring, the statuses including availability of a radio communication channel, presence of the particular medical instrument 30 receiving possible influence of radio waves, a level of electromagnetic noise NS, and possibility of the active monitoring. Assuming that the selectable radio communication channels cannot be used at all because the large communication load of the access point 22 and the portable terminal device 23 in the example pattern 1 (example status 1) is equal to or more than the predetermined value TR0, then the evaluation device 88 judges unavailability of a channel, and terminates the initial evaluation. The use of the radio communication and active monitoring are disabled due to the large communication load.

In the example pattern 2, an available channel exists. The particular medical instrument 30 is present locally within a small distance. Then the evaluation device 88 disables use of the radio communication and the active monitoring and terminates the initial evaluation by considering influence to the particular medical instrument 30. In the example pattern 3, an available channel exists. The particular medical instrument 30 is not present. Then the evaluation device 88 checks a level of the electromagnetic noise NS as influence to the available channel. Assuming that the electromagnetic noise NS is equal to or higher than the threshold Th0, then the evaluation device 88 disables use of the radio communication and the active monitoring and terminates the initial evaluation by considering serious influence to the available channel. The evaluation device 88 stores a monitoring result of the initial evaluation to the storage medium 17E upon terminating the initial evaluation.

In FIG. 21, assuming that the active monitoring is disabled in the initial evaluation (no in the step S1070), the CPU 17C outputs message screens 101, 102 and 103 (environment information) of FIGS. 22-24 to the display device 17A (display panel) according to the example patterns. See the step S1080. Information is indicated with each of the message screens 101-103, including a status of the peripheral communication environment detected by the passive monitoring and the initial evaluation, causes of the communication failure, influence to time of the image transmission, and countermeasures.

In the example pattern 1 without an available channel, the message screen 101 of FIG. 22 is caused to appear. Messages are displayed with the message screen 101, including unavailability of a channel, and information of waiting time required for image transmission due to high traffic load in the communication, by way of a status of the communication environment, a cause of the communication failure, and influence to time for the image transmission. Also, messages of advice are displayed with the message screen 101, including recommendation of using the radio communication after waiting for a short period, or recommendation of using wired communication instead of the radio communication.

In the example pattern 2 of the presence of the particular medical instrument 30, the message screen 102 of FIG. 23 is caused to appear. A message is displayed with the message screen 102, including the presence of a medical instrument which may be influenced by radio waves as a state of the communication environment. Also, a message of advice is displayed with the message screen 102, including recommendation of using wired communication instead of the radio communication.

In the example pattern 3 with large influence of electromagnetic noise NS, the message screen 103 of FIG. 24 is caused to appear. Messages are displayed with the message screen 103, including the presence of a noise source as influence to the radio communication, and information of waiting time required for image transmission due to high possibility of a communication failure, by way of a status of the communication environment, a cause of the communication failure, and influence to time for the image transmission. Also, messages of advice are displayed with the message screen 103, including recommendation of using the radio communication after waiting for a short period, or recommendation of using wired communication instead of the radio communication.

The operator T observing the message screens 101-103 can recognize unsuitability of the communication environment for the radio communication and a reason for the unsuitability. He or she stops using the radio communication in FIG. 21, and changes over to the wired communication with the communication cable in the step S1090. The electronic cassette 16 and the X-ray source 26 are positioned in relation to an object of interest of the body P in the step S1110. An imaging condition is input with the console unit 17 in the step S1120.

Assuming that the use of the radio communication and active monitoring is enabled (yes in the step S1070), then the condition setting unit 82 changes the communication setting of radio communication according to the result of the passive monitoring in the step S1100 as required, for example, the communication setting including frequency of a radio communication channel, packet size, and time-out value. The communication setting is changed also for the control interface unit 18 and the electronic cassette 16 in compliance with a command signal from the console unit 17.

Consequently, the communication setting can be optimized for the communication environment by considering the passive monitoring.

After the positioning in the step S1110, the imaging condition is input in the step S1120. As the radio communication and active monitoring are enabled, the CPU 17C supplies the active monitoring device 87 with a second trigger signal. In response, the active monitoring device 87 performs the active monitoring in the steps of FIG. 19. See the step S1130.

In the active monitoring, the electronic cassette 16 sends test data to the console unit 17 to measure the transmission speed. The active monitoring device 87 causes storing of the measured transmission speed as a monitoring result of the active monitoring. As the active monitoring is performed after the positioning, its condition is a condition of actually transmitting X-ray images. Thus, reliability in measuring the transmission speed is high. After performing the active monitoring, the evaluation device 88 performs the comprehensive evaluation as illustrated in FIG. 20 (step S1140) according to the monitoring result of the passive monitoring, a result of the initial evaluation and a result of the active monitoring.

The evaluation device 88 in the comprehensive evaluation detects causes of a communication failure and final enablement of radio transmission of an image. See Table 1. In the example pattern 4, the electromagnetic noise NS is less than the threshold Th0 but is equal to or more than the threshold Th1 (Th1≤NS<Th0). Then it is judged that a speed difference between the estimated and measured speeds of the transmission speed is larger than a tolerable range. It is judged that the speed difference is caused by a noise source.

Assuming that there is no speed difference between the estimated and measured speeds in the example pattern 5, it is judged that there is no cause of the communication failure. Assuming that there is a speed difference between the estimated and measured speeds in the example pattern 6 even with small electromagnetic noise NS (NS<Th1<Th0), then it is judged that a cause is a blocking object or relative position of the X-ray imaging apparatus 12. In the case of the example patterns 4, 5 and 6, the enablement of radio transmission of an image is finally checked by checking a value of the transmission speed equal to or more than the predetermined value. The evaluation device 88 determines an estimated time of transmission of an image according to the measured speed of the transmission speed, and terminates the comprehensive evaluation.

In case the comprehensive evaluation is terminated, message screens 104, 105 and 106 (environment information) are output by the CPU 17C to the display device 17A according to the example patterns 4-6. See FIGS. 25-27. Information is indicated with each of the message screens 104-106, including a status of the peripheral communication environment, causes of the communication failure, influence to time of the image transmission, and countermeasures.

In FIG. 21, assuming that the transmission speed is equal to or more than a predetermined reference speed (yes in the step S1150), message information of this status is displayed in the step S1160. In the example pattern 4 receiving influence of the electromagnetic noise NS, the message screen 104 of FIG. 25 is caused to appear in case the transmission speed is equal to or more than the reference speed. Messages are displayed with the message screen 104, including the presence of a noise source as influence to the radio communication, and information of waiting time required for image transmission with the low level of the transmission speed, information of estimated time of the image transmission, by way of a status of the communication environment, a cause of the communication failure, and influence to time for the image transmission.

In the example pattern 4, assuming that the transmission speed is lower than the reference speed (no in the step S1150), the transmission speed is still lower than that in the situation of the message screen 104. Then the message screen 103 of FIG. 24 is indicated in the step S1080 in a manner similar to the example pattern 3, to recommend the wired communication in the step S1090.

In the example pattern 5 without causes of a communication failure, the transmission speed is equal to or more than the reference speed (yes in the step S1150). The message screen 105 of FIG. 26 is caused to appear in the step S1160. Messages displayed with the message screen 105 are a good condition in the radio communication environment and an estimated time of image transmission, as information of the communication environment.

For the example pattern 6 in which a communication failure is caused by a blocking object or relative position of the X-ray imaging apparatus 12, the transmission speed is lower than the reference speed (no in the step S1150). Then the message screen 106 of FIG. 27 is caused to appear in the step S1080. Messages are displayed with the message screen 106, including occurrence of a communication failure due to influence of a blocking object or an inappropriate relative position of the console unit 17 and the control interface unit 18 to the electronic cassette 16, information of waiting time required for image transmission due to decrease in the transmission speed, and information of estimated time for the image transmission, and the like, by way of a status of the communication environment, a cause of the communication failure, and influence to time for the image transmission. Also, a message of advice is displayed with the message screen 106, including recommendation of using wired communication instead of the radio communication. In this case, the operator T stops using the radio communication and changes over to the wired communication in the step S1090.

In the example pattern 6, assuming that the transmission speed is equal to or higher than the predetermined reference speed (yes in the step S1150), then the transmission speed is found at a low level, although higher than that according to the situation of the message screen 106. A message screen (not shown) is indicated to inform that considerable time is required for image transmission due to the low level of the transmission speed, with data of the estimated time for the image transmission.

The operator T recognizes peripheral communication environment and causes of a communication failure by observing the message screen, and changes a condition of the wired communication as required. Then the console unit 17 sends a command signal to the electronic cassette 16 for a ready state in the step S1170 of FIG. 21. The electronic cassette 16 in the ready state operates for detecting a start of irradiation with the detection sensors 56 in FIG. 4.

The operator T observes the ready indicator 72 of the input screen 61 and confirms the ready state of the electronic cassette 16. He or she checks suitability of the posture of the body P, and manually operates the start switch 28 in the step S1180. In response, the X-ray source 26 starts irradiation of X-rays. The electronic cassette 16 detects the start of the irradiation with the detection sensors 56. Then the sensor panel 41 comes to start the storing, and detects an image in the step S1190.

In case the irradiation time elapses, the X-ray source 26 terminates the irradiation. As the detection sensors 56 detect the termination of the irradiation, the electronic cassette 16 terminates the storing and reads out an X-ray image. The X-ray image is stored to the memory 49.

The X-ray image is read out from the memory 49, and transmitted to the console unit 17 through the radio or wired communication interface 37 or 50 in the step S1200. The console unit 17 receives the X-ray image with the radio or wired communication interface 38 or 60. The operator T checks the X-ray image at the console unit 17 in the step S1210. Thus, one event of imaging is terminated.

Assuming that imaging of plural images is instructed in the imaging request, the above steps are repeated inclusive of the positioning step. An imaging condition is set again after the positioning, so that the active monitoring is performed. Changes may occur in the relative position of the X-ray imaging apparatus 12 and a relative position of a blocking object according to the positioning. Thus, it is possible effectively to output information suitable for the communication environment by performing the active monitoring after the positioning.

At the end of imaging of the body P, the operator T places the electronic cassette 16 on the medical cart 14, engages the lock mechanism 33 of the medical cart 14, and moves the medical cart 14 to a second hospital room for the in-patient care. For next imaging, the lock mechanism 33 is released. In response to this, the above-described process is repeated inclusive of the passive monitoring.

Consequently, the communication environment is measured in response to operation of unlocking immediately after entry into a hospital room in the serial steps of the imaging. It is possible to measure the communication environment exactly for each of the hospital rooms in particular for the in-patient care.

As described heretofore, the passive monitoring and active monitoring are used for measuring the communication environment according to the invention. The passive monitoring receives ambient electromagnetic waves to measure spectral intensity of the electromagnetic waves. The active monitoring measures the transmission speed by the data communication. There are differences between the methods in the measurement and the type of measured information. It is possible reliably to estimate causes of the communication failure by use of the two methods of monitoring in comparison with the known technique in which only the transmission speed is measured for estimating causes of a communication failure.

A communication failure caused by a blocking object, such as the multi-path phasing (MPP) described above, cannot be estimated by only either one of the passive and active monitoring. To be precise, the multi-path phasing occurs even without electromagnetic noise locally within a small distance. Only the use of the passive monitoring to measure the intensity of electromagnetic waves cannot estimate occurrence of multi-path phasing. In contrast, the active monitoring can measure the transmission speed, but cannot detect an exact one of the multi-path phasing and the electromagnetic noise as a cause of decreasing the transmission speed. However, the combined use of the passive monitoring for measuring the electromagnetic noise and the active monitoring for measuring the transmission speed is effective in estimating occurrence of multi-path phasing as a cause of a communication failure with high probability.

Also, the combination of the passive and active monitoring enables rapid discovery of causes of the communication failure in comparison with a known technique in which the communication history acquired by imaging of plural events is analyzed or considered to discover a communication failure. It is possible to detect causes of the communication failure without imaging in case the both of the passive and active monitoring are utilized. As described heretofore, causes of the communication failure can be discovered before starting the imaging by performing the passive and active monitoring before the imaging. It is possible to use a countermeasure before starting the imaging, for example, changeover to the wired communication for the unavailability of the radio communication.

Also, there is an auxiliary effect of preventing a communication failure. Wasteful use of a battery for the electronic cassette 16 can be suppressed. In case the radio communication is used with possibility of the communication failure, power may be used wastefully. The use of the radio communication is enabled only in the communication environment of ensuring the transmission speed equal to or higher than the predetermined reference speed. Thus, time for the image transmission can be shortened. It is possible to reduce the power supply of the battery according to the shortness of the time of image transmission.

In the above embodiments, the wired communication is recommended should the radio communication be disabled. However, an alternative method other than the wired communication can be recommended. For example, use of a portable memory device such as a USB memory (universal serial bus memory) can be suggested as an alternative method. A connector is provided on the electronic cassette 16 for connecting the memory device. In the electronic cassette 16, a detected X-ray image is kept stored in the memory 49 without external transmission. In response to the connection of the memory device, data of the X-ray image is output from the memory 49 to the memory device. The X-ray image is input to the console unit 17 through the memory device.

Also, it is possible to acquire detailed information of a status of the communication environment, causes the communication failure and suitable countermeasure by the combined use of the passive and active monitoring. An operator T can smoothly work for imaging by referring to the detailed information.

As described above, an operator T must form as many images as 50 or more per day by himself or herself. Should communication failure occur in a severe condition of short time, he or she may feel mental stress. However, it is possible to reduce the stress of the operator T by rapidly detecting causes of the communication failure before starting the imaging. It can be anticipated that the image transmission will take much time even upon occurrence of the communication failure, so that causes of the communication failure can be found exactly.

In the above embodiments, the evaluation device 88 operates according to the results of the passive and active monitoring. However, results of the passive and active monitoring can be output to and displayed in the display device 17A without evaluation in the evaluation device 88. Assuming that an operator T has a skill of reading data on the basis of communication technology, he or she can briefly recognize causes of a communication failure by observing and considering the results of the passive and active monitoring.

In the above embodiments, spectral intensity of electromagnetic waves and its time profile are measured in the frequency band of the plural radio transmission path channels in the passive monitoring. However, the intensity and time profile can be measured only for a particular frequency band, for example, intensity of electromagnetic noise overlapping on the frequency band of one radio transmission path channel.

The above-described message screens are only examples. The items of information in the message screens can be modified, increased or decreased. For example, the number of the access points 22 disposed locally within a small distance can be indicated. A beacon signal from the access points 22 is transmitted at a frequency of an assigned radio communication channel as illustrated in FIG. 10 or 12. In case the number of the beacon signals is counted, it is possible to detect the number of the access points 22. Should a plurality of the access points 22 be assigned with a radio communication channel of an equal frequency, a plurality of the beacon signals of the equal frequency are transmitted. In relation with these signals, a network identifier included in the beacon signal is recognized, to check whether the beacon signal of the equal frequency is from the different access point 22 or from the same access point 22. Examples of the network identifiers are SSID (Service Set Identifier) and ESSID (Extended Service Set Identifier). Each of the access points 22 has a predetermined identifier. It is possible to find the number of the access points 22 correctly even in occurrence of overlap of frequencies between the access points 22 by use of the network identifies.

Also, communication load of the selectable plural radio communication channels can be displayed for each channel. Assuming that plural radio communication channels are available, it is possible for the operator T to select one of those for use manually. Also, communication load of unavailable radio communication channels for selection can be indicated in addition to the available radio communication channels.

Also, the use of the radio communication can be avoided by checking whether the particular medical instrument 30 is present according to the passive monitoring before the active monitoring in the above embodiment. Influence to the particular medical instrument 30 can be reduced effectively. Note that the active monitoring can be performed first assuming that consideration of the influence to the particular medical instrument 30 is not required. However, performing the passive monitoring first is preferable because of its advantage mentioned above.

The initial evaluation and comprehensive evaluation of the above embodiments are only examples. Other methods of detection can be used. Assuming that it is unnecessary to consider influence to the particular medical instrument 30, it is possible to perform all of those evaluations after acquiring results of the passive and active monitoring.

TABLE 2

|  |  | Example pattern 1A | Example pattern 1B |
|---|---|---|---|
| Passive monitoring |  | Spectral intensity of electromagnetic waves | |
| Initial evaluation | Presence of particular medical instrument | No | No |
|  | Level of electromagnetic noise NS | $NS < Th1 < Th0$ (low) | $NS < Th1 < Th0$ (low) |
|  | Enablement of active monitoring | Yes | Yes |
|  | Estimated transmission speed | 50 Mbps | 50 Mbps |
| Active monitoring | Measured transmission speed | 2 Mbps | 30 Mbps |
| Comprehensive evaluation | Communication load | $X1 \geq TR0$ | $TR0 > X2$ |
|  | Cause of communication failure | High traffic load | Rather high traffic load |
|  | Availability of radio communication for image | No | Yes or no, rather low speed |
|  | Message | Wait or recommend wired communication | Estimated time & recommend wired communication as per speed |

|  |  | Example pattern 2A | Example pattern 3A |
|---|---|---|---|
| Passive monitoring |  | Spectral intensity of electromagnetic waves | |
| Initial evaluation | Presence of particular medical instrument | Yes | No |
|  | Level of electromagnetic | — | $NS \geq Th0$ (high) |

TABLE 2-continued

| | | | |
|---|---|---|---|
| | noise NS | | |
| | Enablement of active monitoring | No | No |
| | Estimated transmission speed | — | — |
| Active monitoring | Measured transmission speed | — | — |
| Comprehensive evaluation | Communication load | — | — |
| | Cause of communication failure | Particular medical instrument | Noise source |
| | Availability of radio communication for image | No | No |
| | Message | Recommend wired communication | Wait or recommend wired communication |

Example patterns (example statuses) of the evaluation in Table 2 are variants of those of Table 1. Availability of a channel is checked according to the communication load in the initial evaluation in the example patterns of the evaluation in Table 1. In contrast, availability of a channel is checked according to the communication load in the comprehensive evaluation in place of the initial evaluation in the example patterns of the evaluation in Table 2. Results of the example patterns 2A and 3A in Table 2 are similar to respectively those of the example patterns 2 and 3 in Table 1. This is because it is judged that the active monitoring is impossible for the reason other than the communication load in the example patterns 2A and 3A.

In Table 2, two examples of the example pattern 1 of Table 1 are illustrated. Example patterns 1A and 1B are determined according to the measured values of the communication load in the active monitoring. In the example pattern 1A, the communication load X1 of all the selectable channels is equal to or more than the predetermined value TR0. In the case of unavailability of a channel, a cause of the communication failure is high traffic load in a manner similar to the example pattern 1 of Table 1. It is judged that the wireless image transmission is impossible. In the example pattern 1B, the communication load X2 of at least one available channel is less than the predetermined value TR0 among all the selectable channels. It is judged that the wireless image transmission is possible or impossible according to the speed. Assuming that the communication load is relatively large as illustrated in Table 2, it is judged that the speed is somewhat low and that the wired communication is recommended according to the speed.

In the above embodiments, the frequency or time-out value is changed according to the communication setting of the radio communication in the condition setting unit 82. However, it is possible to change a method of data modulation for modulating data on a carrier wave, and a radio output of radio waves of the radio communication interface 37 of the electronic cassette 16 or the wireless access point 36 of the control interface unit 18.

In the data modulation of digital modulation of digital data of 1 or 0, the carrier wave is changed for the condition change according to the value of 1 or 0 as one bit of digital data. Examples of the condition change include changes in the amplitude, frequency and phase of the carrier wave. In the wireless LAN standard (for example, IEEE 802.11a and 11g), the phase-shift keying (PSK) for charging the phase, and the quadrature amplitude modulation (QAM) as a type of amplitude modulation with changes in the amplitude, are used, as illustrated in the table of FIG. 28.

Examples of the phase-shift keying (PSK) includes binary phase-shift keying (BPSK) in which two phases of 0 and $\pi$ are used, quadrature phase-shift keying (QPSK) in which four phases of 0, $\pi/2$, $\pi$ and $3\pi/2$ are used. It is possible in QPSK to transmit two bits of (01, 11, 10, 00) in the same time period as transmission of one bit of (0, 1) in BPSK. Transmission of higher speed is possible in QPSK than in BPSK.

QAM is a method in which amplitudes of four, eight or plural values are provided in two sine waves perpendicular to one another (with a phase difference of 90 degrees), and a carrier wave is produced in correspondence with waveforms of the combined wave of the two sine waves. Examples of QAM are 16-QAM and 64-QAM. In 16-QAM, amplitudes of the four values are provided in two sine waves. In 64-QAM, amplitudes of the eight values are provided in two sine waves. In QAM, transmission of high speed is possible in comparison with PSK. It is possible in 16-QAM to transmit four bits in a time period equal to that for transmitting one bit in BPSK. It is possible in 64-QAM to transmit eight bits in a time period equal to that for transmitting one bit in BPSK.

Figure 29:
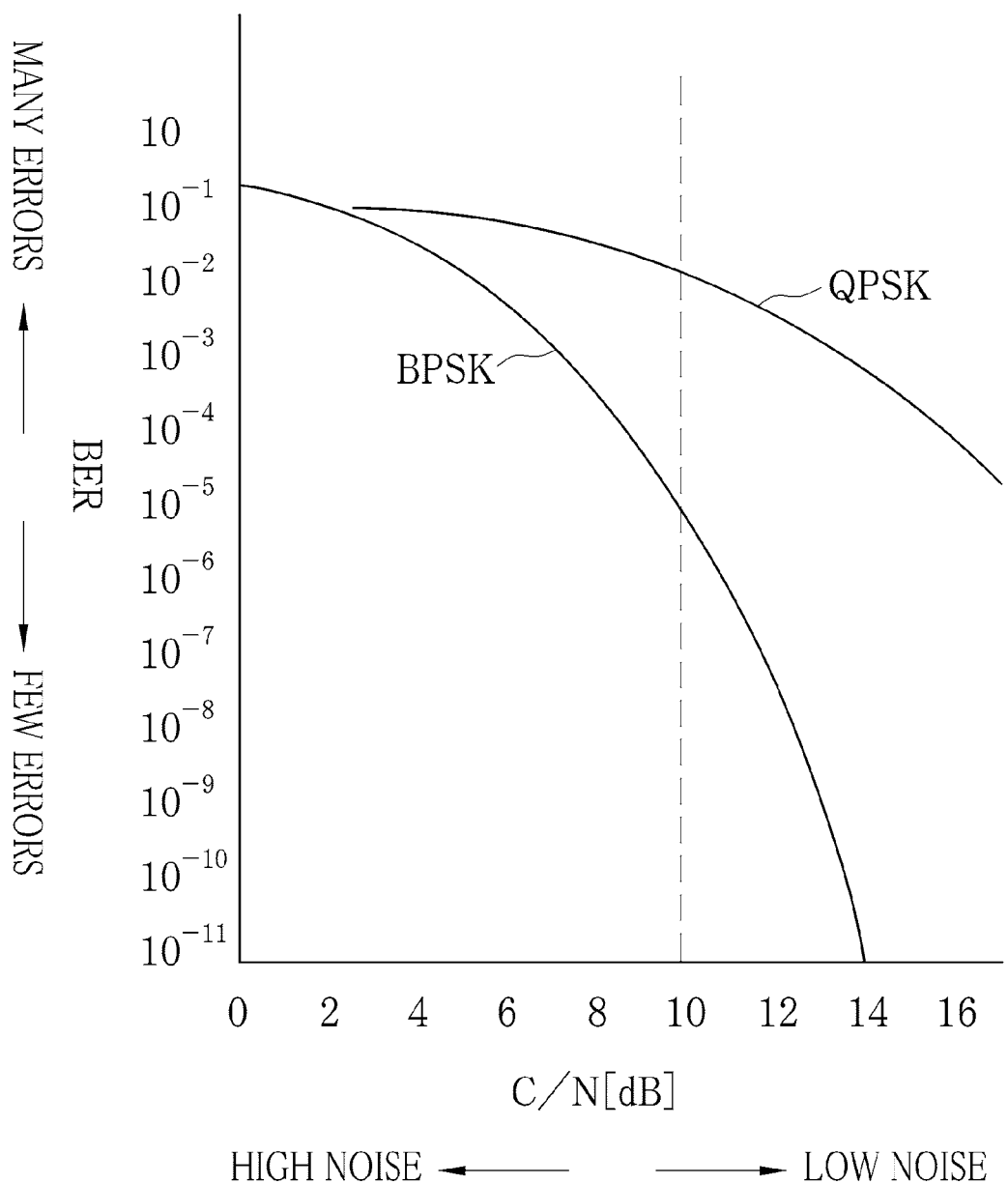
FIG. 29 is a graph illustrating a relationship between a bit error rate (BER) and C/N.

In contrast, robustness of transmission is decreased according to a data size of information transmitted per unit time irrespective of QAM and PSK, because of vulnerability to occurrence of ambient electromagnetic noise and influence of communication environment, such as intensity of received radio waves. In FIG. 29, BPSK is compared with QPSK, which has lower robustness than BPSK in spite of its transmission of higher speed. In FIG. 29, the horizontal axis denotes a ratio C/N (dB) of power C of the carrier wave to the noise N. The vertical axis denotes a bit error rate (BER). For example, a value $10^{-6}$ means probability of occurrence of an error of one bit in relation to a series of $10^6$ bits. In FIG. 29, the bit error rate (BER) is higher in QPSK of higher speed than in BPSK as indicated by the broken line on a condition of comparison at an equal value of C/N. Furthermore, a similar result is obtained from comparison with QPSK and QAM. The bit error rate (BER) in QAM, such as 16-QAM and 64-QAM, is higher than QPSK, but robustness in QAM is lower than QPSK, because of data modulation of higher transmission speed than QPSK.

Figure 30:
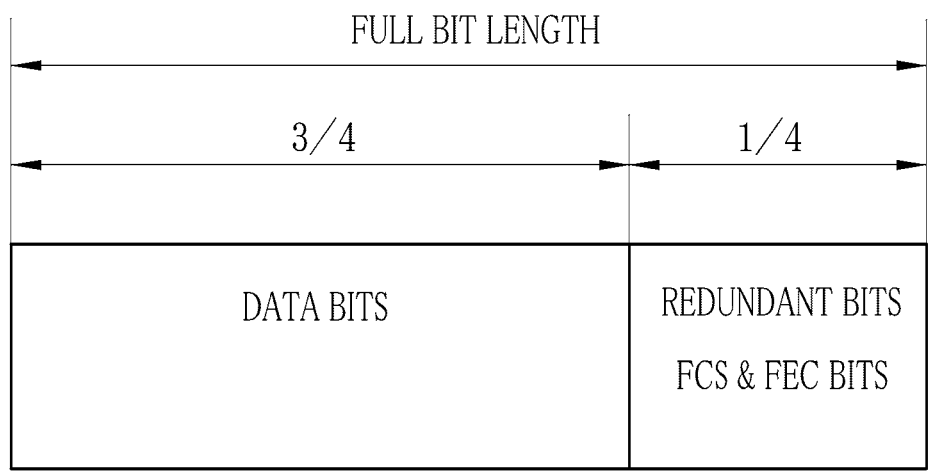
FIG. 30 is a chart illustrating data bits and redundant bits.

As illustrated in FIG. 28, the transmission speed increases in an order of BPSK, QPSK, 16-QAM and 64-QAM. The robustness decreases according to the increase in the transmission speed. In FIG. 28, values ½ and ¾ as added to BPSK, QPSK and the like express a ratio of data bits of data to be transmitted in relation to a total bit length of a frame or packet of the transmission. For example, ¾ in FIG. 30 stands for a method in which ¾ of data bits are included in relation to the total bit length. ½ stands for a method in which ½ of data bits are included in relation to the total bit length. To a portion other than the data bits, redundant bits are added for detecting an error of the data bits or for correcting the error. An example of the redundant bits for detecting an error is Frame Check Sequence (FCS). Examples of the redundant bits for correcting the error are Forward Check Correction (FEC), humming code and the like.

A state of a high ratio of redundant bits (low ratio of data bits) is expressed as high redundancy of data. A state of a low ratio of redundant bits (high ratio of data bits) is expressed as low redundancy of data. According to an increase in the redundancy of data, precision in the error detection and error correction is increased, to increase the robustness. However, efficiency in transmitting data bits is decreased with the increase in the redundancy, so that transmission speed decreases. In the example of FIG. 28, the transmission speed is higher in BPSK ¾ than in BPSK ½ even in the same modulation method. Thus, the robustness is lower in BPSK ¾. In short, there is a tradeoff between the transmission speed and robustness.

The condition setting unit 82 can change the data modulation or redundancy of data according to the result to the passive monitoring. For example, in case the electromagnetic noise is relatively large, the data modulation is changed over to a method with high robustness in relation to noise.

Figure 31:
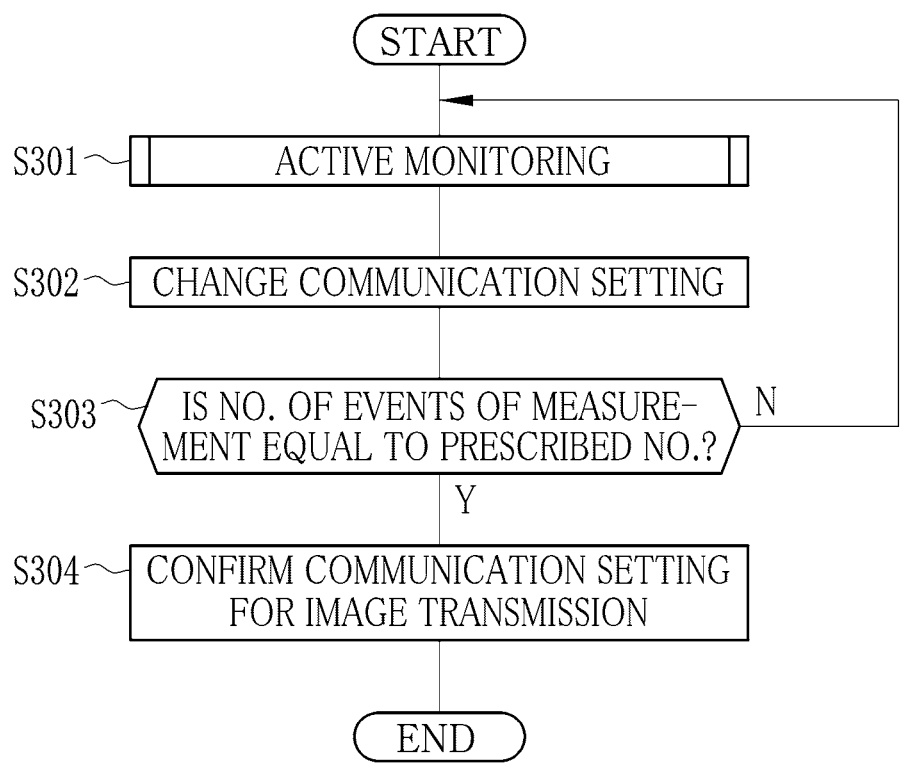
FIG. 31 is a flow chart illustrating acquisition of a communication setting according to active monitoring of plural events.

Furthermore, the condition setting unit 82 can change the communication setting of radio communication according to the result of the active monitoring. For example, results of plural events of the active monitoring are considered by the condition setting unit 82 to change the communication setting as illustrated in FIG. 31. At first, the active monitoring is performed for one time in the step S301. The condition setting unit 82 changes the communication setting, for example, the data modulation in the step S302. After this, the active monitoring is performed again. Those steps are repeated for the plural events of the active monitoring. Plural transmission speeds as results of the active monitoring are stored as the monitoring result 91 in FIG. 7. In case the number of the events of the measurement becomes a prescribed upper limit, the active monitoring is terminated in the step S303. The condition setting unit 82 determines one of the plural communication settings with the highest transmission speed according to the results, and designates the determined communication setting for use in the image transmission of an X-ray image in the step S304.

As a method of changing the setting of the radio communication, a first data modulation with a low transmission speed (high robustness) is changed stepwise to a second data modulation with a high transmission speed (low robustness). It is possible to store a bit error rate (BER) as a monitoring result of the active monitoring of events different in the setting of the radio communication, in addition to the transmission speed. The bit error rate can be measured according to an error detection code (for example, FCS or frame check sequence) included in the packet of the transmission and reception, as described above. According to the bit error rate included in the monitoring result of the active monitoring in the plural events, the condition setting unit 82 determines a method of the data modulation with a highest transmission speed as the setting of the radio communication at the time of transmitting an X-ray image, as a method of the data modulation in which the bit error rate is equal to or lower than the predetermined value.

Also, the condition setting unit 82 can determine the communication setting of radio communication at the time of image transmission of an X-ray image according to both results of passive and active monitoring. For example, it is judged from the passive monitoring that the electromagnetic noise NS is comparatively large. Then the active monitoring is performed, to determine a communication setting to obtain a highest transmission speed according to the result of the active monitoring. Then the condition setting unit 82 considers the result of the passive monitoring of the comparatively large electromagnetic noise NS, and selects a communication setting with a higher robustness by one step than an available communication setting according to the active monitoring. The selected communication setting is designated for use in the image transmission of an X-ray image.

To be precise, the communication setting of radio communication is determined with priority of robustness over the transmission speed according to the result of the passive monitoring. In the communication environment with large electromagnetic noise NS, the bit error rate (BER) is high, to increase the number of events of communication errors of the packet. Then the number of events of retransmitting the packet becomes as high as an upper limit, to interrupt the transmission of an X-ray image in the course of the image transmission. After the interruption, retransmission of the entirety of the data of the X-ray image must be performed. As the data size of the X-ray image is large, a loss in the transmission time in the retransmission of the entire data is considerably large, due to a time point of occurrence of the interruption. As selection of the data modulation or redundancy of data is carried out according to high robustness, it is possible to avoid unwanted occurrence of retransmission of the entire data, even with a decrease in the transmission speed.

In general, a transmission speed and robustness are increased according to an increase in a radio output of the transmission of radio waves from the radio communication interface 37 of the electronic cassette 16 or the wireless access point 36 of the control interface unit 18. However, influence of the radio output to the portable terminal device 23, the electromagnetic medical instrument 24 and the like is increased according to the increase in the radio output. Accordingly, it is possible in the condition setting unit 82 to change the radio output suitably, namely to increase the radio output assuming that no instrument is detected by the passive monitoring, and to decrease the radio output assuming that an instrument is present locally within a small distance. Also, the radio output can be changed according to the active monitoring, namely to increase the radio output assuming that a bit error rate (BER) is high in the active monitoring.

Also, the active monitoring can be performed earlier than the passive monitoring. In consideration of influence to other instruments, it is preferable to perform the active monitoring by initially setting a low level for the radio output of transmission. Assuming that it is judged in the passive monitoring that no other instrument is present, then the radio output of the transmission can be set higher. The radio output is preferably increased stepwise.

As described heretofore, it is possible in the active monitoring to measure occurrence of a communication error, such as a BER and the number of errors, in addition to the transmission speed. The occurrence of the communication error influences the transmission speed, so that the transmission speed can be estimated according to the occurrence of the communication error. Also, the occurrence of the communication error can be utilized for recognition to determine the communication setting for the radio communication. It is possible in the active monitoring to measure the occurrence of the communication error in addition to or in place of the transmission speed. Furthermore, the passive or active monitoring device 86 or 87 can be utilized for the purpose of determining the communication setting for transmitting or receiving an X-ray image in addition to or in place of a purpose of estimating a cause of a communication failure.

Furthermore, power density of radio waves generated by the X-ray imaging apparatus 12 can be changed as communication setting, for the purpose of reducing influence to the particular medical instrument 30. In FIG. 9, a channel of a width of 20 MHz is used as one radio communication channel. To decrease the power density, two channels of 20 MHz are combined together to form one channel with a larger width of 40 MHz. This technique is referred to as channel bonding. In case the total of the energy for outputting radio waves is equal, the power is spread according to largeness of the frequency band. Thus, the power density decreases, and radio wave intensity decreases. Assuming that frequency of serious influence to the particular medical instruments 30 is given, it is possible to reduce the radio wave intensity influencing the frequency by lowering the power density. Thus, influence to the particular medical instruments 30 can be reduced.

Second Preferred Embodiment

Figure 32:
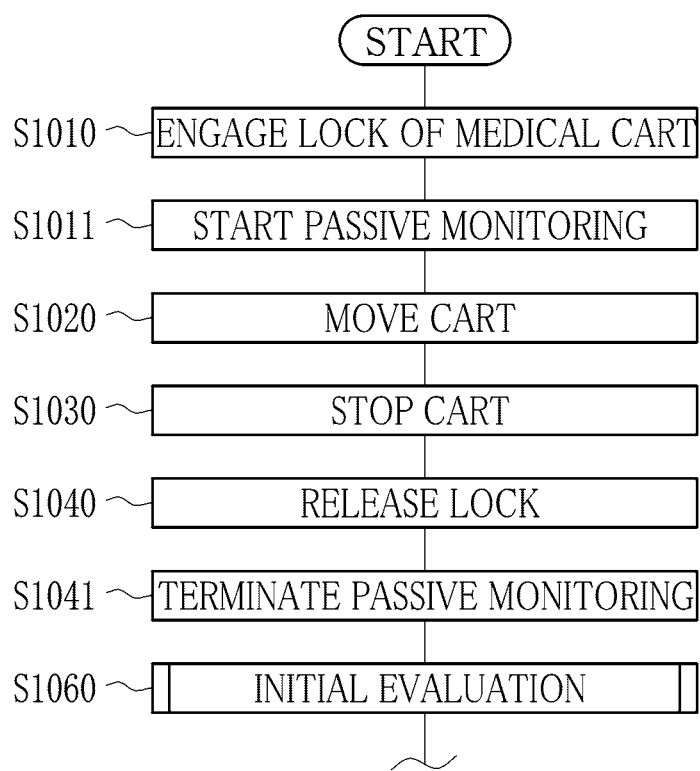
FIG. 32 is a flow chart illustrating of a second preferred embodiment.

In the above embodiment, the passive monitoring is started upon an output of an unlock signal of the medical cart 14. FIG. 32 illustrates another preferred embodiment, in which the passive monitoring is started by transmitting a first trigger signal from the medical cart 14 in the step S1011, upon engaging the lock mechanism 33 of the medical cart 14 in the step S1010 in the storage space 15. In case the lock mechanism 33 is released upon entry in a hospital room in the step S1040, the passive monitoring is terminated in the step S1041. Therefore, the passive monitoring is continued until the entry in the hospital room from the storage space 15 in the step S1020. It is possible to collect information of communication environment around the hospital room in addition to the inside of the hospital room of the in-patient care. Assuming that the number of the particular medical instruments 30 is high in the hospital facility 19, it is possible to prevent failure in detecting the particular medical instruments 30 by performing the passive monitoring not only in hospital rooms but also thereabout.

Also, the time sequence of starting the passive monitoring can be different from the above operation. For example, a transmission device can be disposed at an entrance of a hospital room for generating a first trigger signal. In case the medical cart 14 enters the hospital room, the console unit 17 can receive the first trigger signal. Thus, the passive monitoring can be started upon the entry to the hospital room. Also, a stop sensor can be disposed in the medical cart 14 to start the passive monitoring in case a stop of the medical cart 14 is detected by the stop sensor.

The time point of starting the active monitoring is a time point of setting the imaging condition, because it is estimated that the positioning has been finished. It is possible to detect the finish of the positioning directly to start the active monitoring. For example, a ready button is disposed in a screen on the console unit 17. Upon the finish of the positioning, the operator T operates the ready button. The console unit 17 transmits a second trigger signal to the active monitoring device 87 at the time point of operating the ready button, to start the active monitoring.

Also, the ready button of positioning can be provided in the electronic cassette 16 or the medical cart 14. In the structure, a ready flag of the positioning is sent to the console unit 17. Also, a detection sensor for detecting the finish of the positioning can be provided in place of the ready button of positioning. An example of the detection sensor is an acceleration sensor incorporated in the electronic cassette 16. During the positioning, a posture of the electronic cassette 16 changes. However, the electronic cassette 16 becomes stationary after the positioning. In case a state of the stationary posture of the electronic cassette 16 is continued according to an output of the acceleration sensor, then it is judged that the positioning is finished. A ready flag is sent by the electronic cassette 16 to the console unit 17.

Also, an ultrasonic transducer can be disposed on each of the electronic cassette 16 and the X-ray source 26 as a detection sensor, for transmission and reception of an ultrasonic signal. The ultrasonic transducers detect a state of positioning the electronic cassette 16 and the X-ray source 26 directed to one another, to recognize the finish of the positioning. A ready flag is transmitted to the console unit 17.

Also, the passive and active monitoring can be performed according to manual operation. It is possible for the operator T to do so at a time point required according to his or her observation. An operation button for this purpose can be disposed on the console unit 17.

Third Preferred Embodiment

Figure 33:
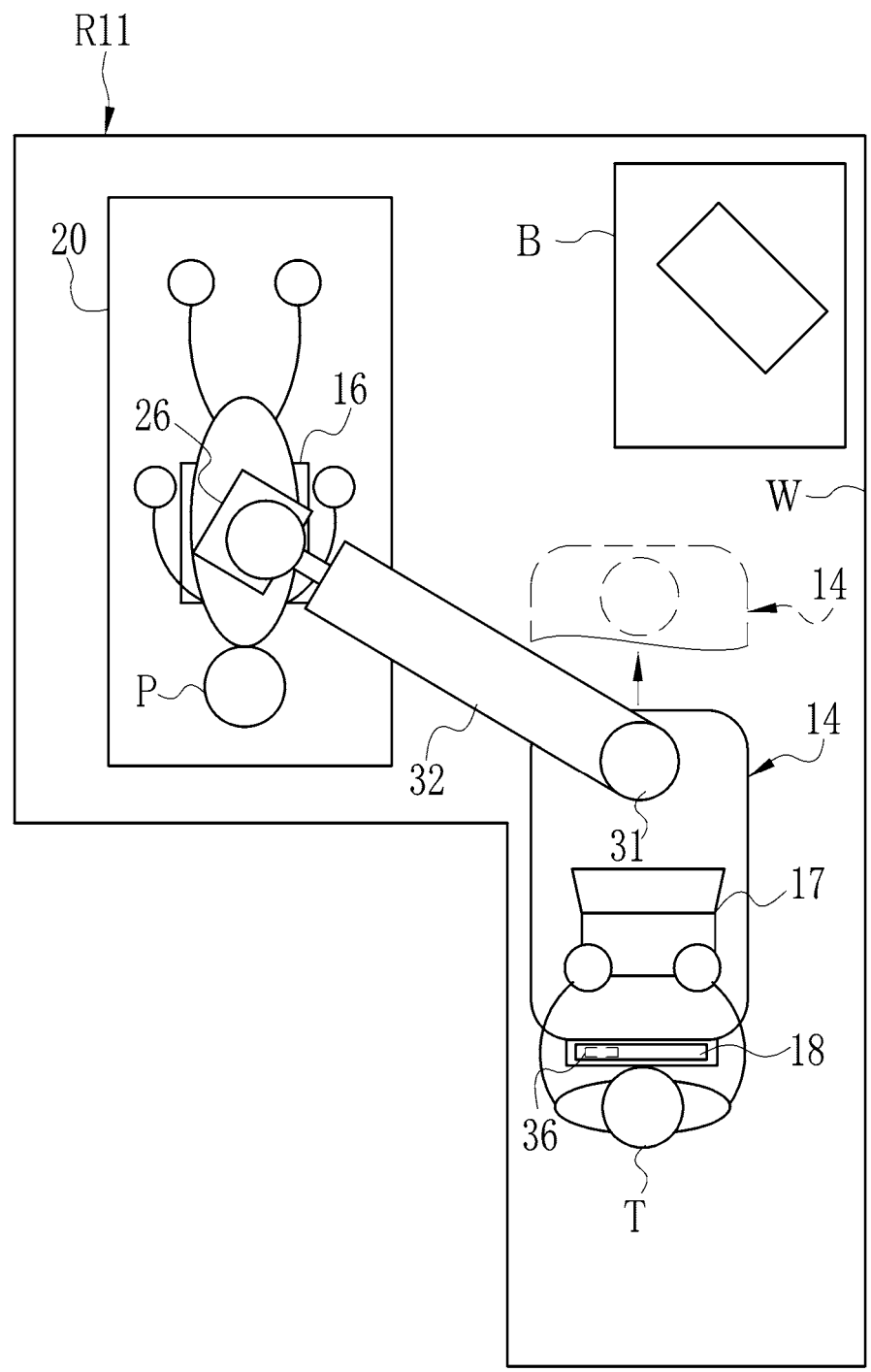
FIG. 33 is a plan illustrating a position adjustment of a third preferred embodiment.

It is likely in the first embodiment that a communication failure is caused by a blocking object or a relative position of the X-ray imaging apparatus 12 as described with the example pattern 6 of Table 1. For example, the medical cart 14 can be moved as illustrated in FIG. 33 to adjust the relative position between the console unit 17 and the control interface unit 18 on the medical cart 14 and the electronic cassette 16 on the hospital bed 20, so that a transmission speed may be raised effectively. Ina third preferred embodiment, an assist function (aid function) for the position adjustment is added to the X-ray imaging apparatus 12 of the first embodiment. For the remaining elements in the structure, the first embodiment is repeated.

Figure 34:
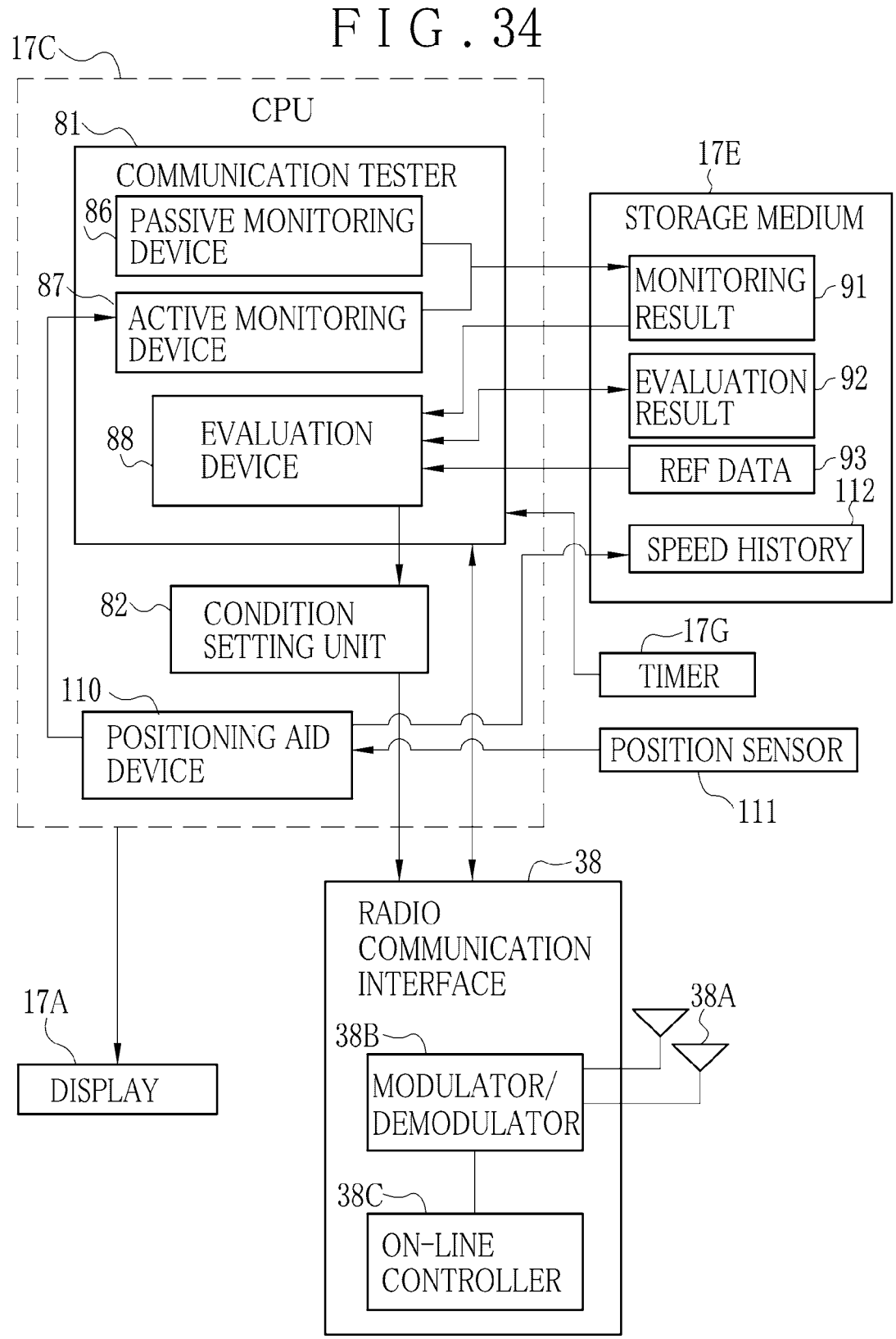
FIG. 34 is a block diagram schematically illustrating a console unit.

In FIG. 34, the console unit 17 of FIG. 7 is repeated but with a difference in additionally having a positioning aid device 110 or position estimation device, and a position sensor 111.

The position sensor 111 detects a position of the console unit 17 for the purpose of position adjustment. Examples of the position sensor 111 are an acceleration sensor and a GPS sensor for acquiring GPS information (Global Positioning System information). For example, the position sensor 111 outputs position information of a shift position after the movement with reference to an original position, which is a position of the console unit 17 immediately before the movement. The position information is expressed by coordinate information of coordinates in X and Y-directions. Thus, it is possible to detect a shift distance, shift locus and the like from the original position in addition to the shift position.

The positioning aid device 110 causes the active monitoring device 87 to measure the transmission speed at the time of the position adjustment. The measurement of the transmission speed is repeatedly performed at a predetermined time interval during the position adjustment. In FIG. 35, a speed history 112 is produced by the positioning aid device 110 as information of a relationship between an elapsed time after starting the position adjustment, the transmission speed, and the position information output by the position sensor 111. The speed history 112 is stored in the storage medium 17E.

FIG. 36 is a flow chart of the position adjustment. A message screen 113 (environment information) is output by the CPU 17C to the display device 17A in the case of the example pattern 6 with a message of recommending the position adjustment of FIG. 37, in place of the message screen 106 of FIG. 27. See the step S2010. The message screen 113 indicates information of the message screen 105 and also the message of recommending changes in the position of the console unit 17 and the control interface unit 18 for the position adjustment. A yes button 113A (on button) is operated by the operator T for the position adjustment. A no button 113B (off button) is operated for a condition without position adjustment.

In case the position adjustment is designated by operating the yes button 113A (yes in the step S2020), the positioning aid device 110 is started up. Assuming that no position adjustment is designated after operating the no button 113B (no in the step S2020), the positioning aid device 110 is inactive. Upon the startup of the positioning aid device 110, the active monitoring in the active monitoring device 87 is started in the step S2030. Simultaneously, storing of the transmission speed measured by the active monitoring device 87 to the area of the speed history 112 is started in the step S2040.

In FIG. 33, the operator T moves the medical cart 14, together with the console unit 17 and the control interface unit 18 in the step S2050. Position information output by the position sensor 111 changes upon starting the movement of the console unit 17 and the control interface unit 18. The speed history 112 is updated by additionally writing a current transmission speed from the active monitoring device 87 and current position information from the position sensor 111.

The CPU 17C reads out the current transmission speed from the speed history 112, and drives the display device 17A to display the current transmission speed in the real-time manner in the step S2060. In FIG. 38, a speed screen 114 appears to indicate the transmission speed. Messages are also displayed in the speed screen 114, including information of acquisition of an optimized position, information of the transmission speed in the present position, and information of an upper limit speed as a theoretical value. Also, an end button 114A for terminating the assist function (aid function) for the position adjustment is displayed.

The operator T observes the speed in the speed screen 114 in the real-time manner, and can recognize an increase or decrease in the transmission speed. Also, the transmission speed can be compared with the theoretical value to recognize an increase or decrease in a difference of the speed from the theoretical value.

Figures 39, 40:
FIG. 39 is a front elevation illustrating an optimization screen for an optimized position.
FIG. 40 is a graph illustrating a locator for the optimized position.

The console unit 17 and the control interface unit 18 are stopped from moving. In case the end button 114A is depressed in the step S2070, the positioning aid device 110 terminates the active monitoring of the active monitoring device 87 in the step S2080. Also, the updating of the speed history 112 is terminated in the step S2090. The positioning aid device 110 retrieves position information from the speed history 112 for a position where the transmission speed is the highest, and determines the position as an optimized position. The positioning aid device 110 outputs the optimized position to the display device 17A in the step S2100. In FIG. 39, an optimization screen 116 appears and indicates the optimized position.

The optimization screen 116 informs an optimized position by a message with time and a distance. For example, the message is that the optimized position is a location at the time 3 seconds before the stop of the movement, and/or is located at a distance of 50 cm in a direction reverse to the movement before the stop of the movement. Also, the optimization screen 116 indicates a transmission speed in the optimized position and estimated time of the image transmission. The operator T can utilize the information of the optimized position, and can move the medical cart 14 to set the console unit 17 and the control interface unit 18 in the optimized position.

Also, a locator 117 of FIG. 40 can be used for indicating the optimized position in place of or in addition to the optimization screen 116. The locator 117 is a screen for the optimized position in a visible form by plotting the optimized position in a two-dimensional coordinate space with X and Y-axes. An original position O of the console unit 17, the present position PP and the optimized position BP are displayed in the locator 117. The original position O is an initial position related to movement of the console unit 17. It is possible easily to check which direction should be selected for moving from the present position PP to the optimized position BP.

In the present embodiment, the transmission speed is correlated with the elapsed time of measurement of the transmission speed and with the position information of a position of the measurement, to store the speed history 112. However, only either one of the elapsed time and the position information can be used. In the optimization screen 116 of FIG. 39, the optimized position can be expressed by the time (3 second before) with reference to the stop of the movement, or by the distance (50 cm). Indication of the optimized position is sufficient by use of at least one of the time and distance in the speed history 112. Note that a time point can be used as information of the time in place of using the elapsed time from the start of the movement.

In the above embodiments, the wireless LAN standard is IEEE 802.11n. However, other wireless LAN standards can be used, for example, IEEE 802.11a, IEEE 802.11b, and IEEE 802.11ac of a new generation.

In the above embodiments, the X-ray imaging apparatus 12 includes the electronic cassette 16, the console unit 17 and the control interface unit 18. However, a component of the control interface unit 18 having the wireless access point 36 may be incorporated in either one of the electronic cassette 16 and the console unit 17, so that the X-ray imaging apparatus 12 can be a two-part structure with the electronic cassette 16 and the console unit 17. The radio communication between the electronic cassette 16 and the console unit 17 is not limited to the infrastructure mode with the wireless access point 36, but can be an ad-hoc mode in which the radio communication interfaces 37 and 38 directly communicate with one another without the wireless access point 36. No function of the wireless access point 36 in the console unit 17 is required. Also, a component of the console unit 17 can be incorporated in the medical cart 14.

In the above embodiments, the medical cart 14 carries the console unit 17 or the control interface unit 18. Also, it is possible to use the console unit 17 after removal from the medical cart 14. As the communication tester 81 is disposed in the console unit 17, any of the above functions can be used even after the console unit 17 is removed from the medical cart 14. The positioning aid device 110 and the position sensor 111 of the third embodiment are disposed in the console unit 17. The aid function or positioning aid device for adjusting the relative position of the console unit 17 relative to the electronic cassette 16 can be also used.

Figure 41:
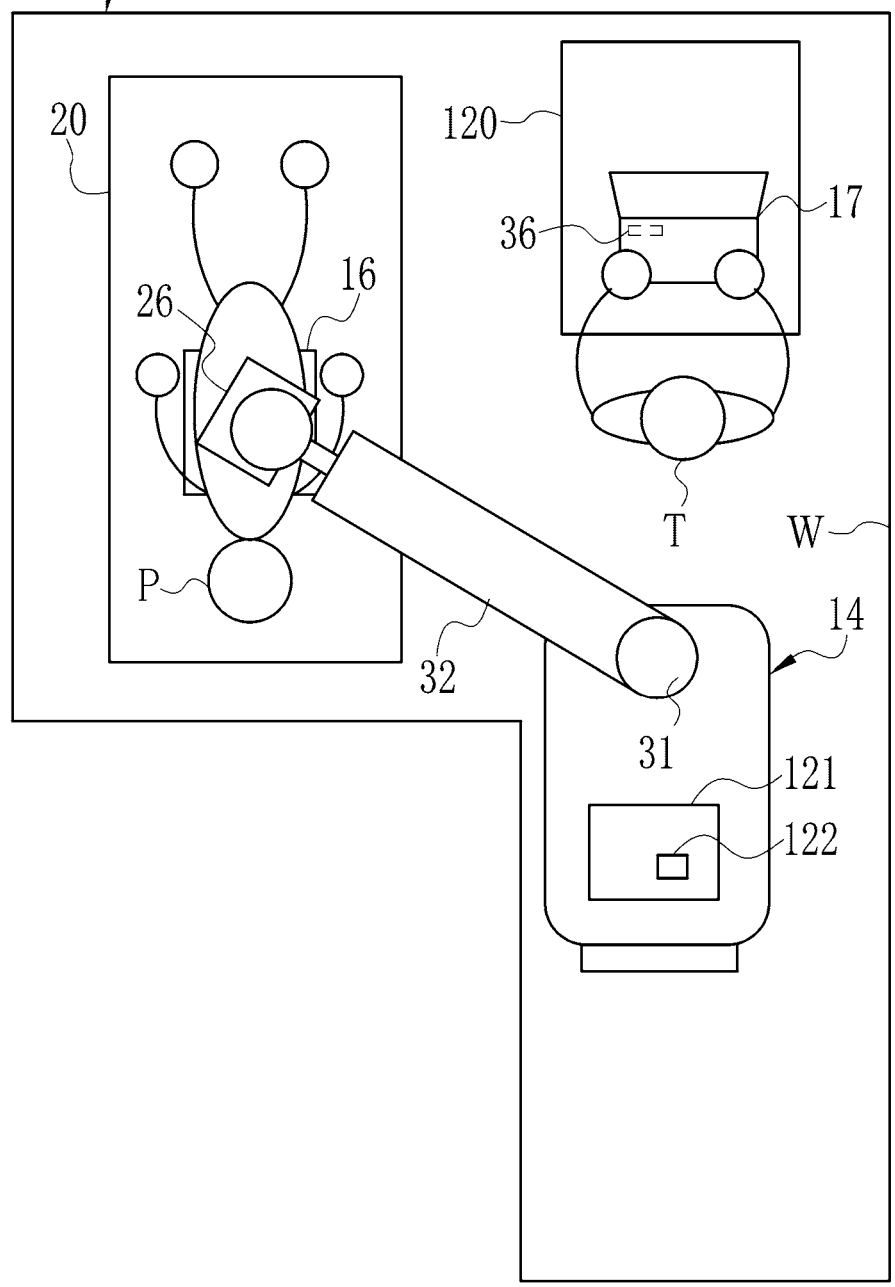
FIG. 41 is a plan illustrating a preferred embodiment in which a console unit is separate from the medical cart.

In FIG. 41, an example is illustrated in which the console unit 17 is used after removal from the medical cart 14. The function of the control interface unit 18 with the wireless access point 36 is incorporated in the console unit 17 of this example. There is no control interface unit 18 of a separate form like the console unit 17. For example, the console unit 17 is placed on a room table 120 in the hospital room R11 for use. To adjust the relative position to the electronic cassette 16, the console unit 17 is moved itself in a manner irrespective of the medical cart 14. For the purpose of position adjustment, the speed screen 114 and the optimization screen 116 are visually checked on the display device 17A of the console unit 17, which is moved to an optimized position.

For the separate use of the console unit 17, it is possible to detect the removal of the console unit 17 from the medical cart 14, to output a detection signal, which can be used as a first or second trigger signal for starting the passive or active monitoring. In FIG. 41, the medical cart 14 has a tray cavity 121 or pocket, and a separation sensor 122. The tray cavity 121 is used for placement of the console unit 17. The separation sensor 122 is disposed in the tray cavity 121. An example of the separation sensor 122 is a photo sensor, and detects a change in a light amount upon removal of the console unit 17 from the X-ray imaging apparatus 12, to output the detection signal. The medical cart 14 transmits the detection signal to the console unit 17. The console unit 17 starts the passive or active monitoring in response to the detection signal.

Also, the console unit 17 and the medical cart 14 can communicate wirelessly with one another. In FIG. 41, the radio communication is typically useful in the separate use of the console unit 17 from the medical cart 14, because no cable is required for connection. A mode of the radio communication from the console unit 17 to the medical cart 14 with the source driver 27 can be an infrastructure mode with the wireless access point 36, and also an ad-hoc mode without using the wireless access point 36. Furthermore, the active monitoring can be performed between the console unit 17 and the medical cart 14 in addition to the path between the console unit 17 and the electronic cassette 16. It is possible to estimate causes of a communication failure and to condition the communication setting according to results of the passive and active monitoring also between the console unit 17 and the medical cart 14.

Figure 42:
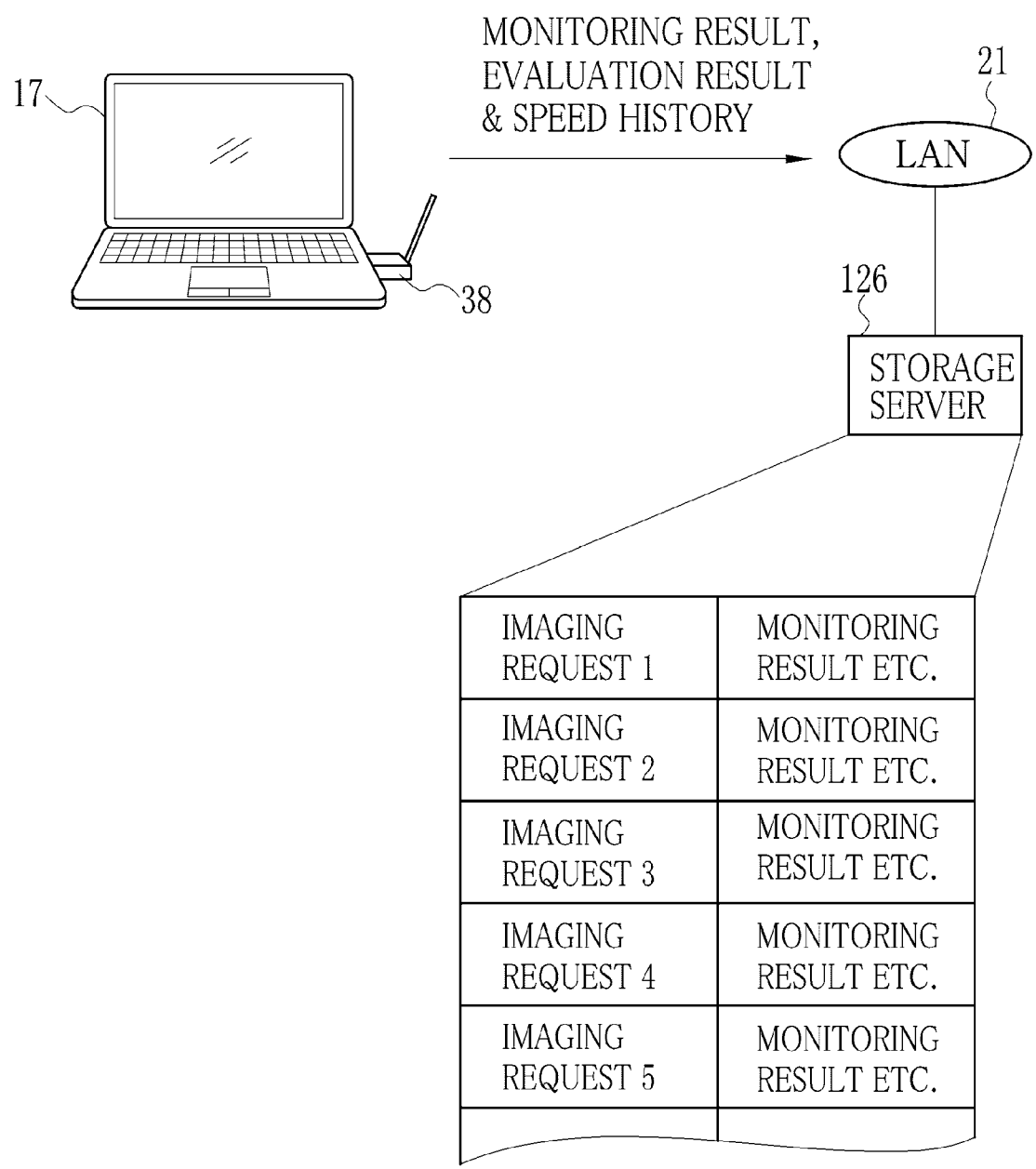
FIG. 42 is a block diagram schematically illustrating a secondary use of results of measurement.

In FIG. 42, it is possible to store the monitoring result 91, the evaluation result 92 and the speed history 112 for use in the secondary use, the monitoring result 91 including the results of the passage and active monitoring, the monitoring result 91 including the result of the initial evaluation and comprehensive evaluation. The results of the monitoring, the detection and speed history (hereinafter referred to as the various monitoring results) are uploaded to and stored in a storage server 126, which stores data from the console unit 17. The storage server 126 stores the monitoring results in connection with the imaging request. The monitoring results include information of the setting of the radio communication at the time of the active monitoring. It is possible to search the monitoring results from a search key as information included in the imaging request. Accordingly, storing the monitoring results in the storage server 126 makes it possible to use the monitoring results in the secondary use, for example, for maintenance of the access point 22, the radio communication interface 38 of the console unit 17 and the radio communication interface 37 of the electronic cassette 16.

The data in the imaging request includes an imaging date, imaging time, and case information of a patient. It is possible to determine a hospital room where an image has been formed according to the case information. The monitoring results stored in the storage server 126 after the imaging for the in-patient care in a hospital room in the hospital facility 19 are usable for environment information of communication environment of various places in the hospital facility 19. It is possible to improve and maintain an on-line system in the hospital facility 19 according to the environment information.

Also, the storage server 126 can be disposed in an external site other than the hospital facility, for example, a medical service center for the X-ray imaging apparatus 12 with the console unit 17 in association with a manufacturer. Transmission of results of the monitoring from the console unit 17 to the storage server 126 is performed by public telephone network, the Internet or the like as a Wide Area Network (WAN). In the use of the Internet, it is preferable to utilize the Virtual Private Network (VPN) for the purpose of security. Thus, the installation of the storage server 126 in the medical service center makes it possible to detect a status of the communication environment of each hospital facility in an early stage. As the result of monitoring is uploaded in a real-time manner, the status can be found in the real-time manner at the service center. Assuming that a communication failure occurs, it is possible for service staff to call the operator T for advice. It is also possible to perform remote maintenance through the WAN immediately with a small change in the setting of radio communication and the like.

In FIG. 43, another preferred embodiment is illustrated, in which a display device or notifier 131 is disposed on the electronic cassette 16. A display device or notifier 132 is disposed on the control interface unit 18. Those are for the purpose of indicating a message screen. Such a display device can be disposed on any of the medical cart 14, the control interface unit 18 and the electronic cassette 16 in addition to the display device 17A of the above embodiment.

Various manners of using the display devices 131 and 132 are conceivable. For example, all available information of the communication environment is displayed for the display device 17A of the console unit 17. The display devices 131 and 132 of the electronic cassette 16 or the control interface unit 18 can display only the transmission speed of a result of the active monitoring. In short, information to be displayed can be widened or narrowed for each one of the display devices 131 and 132. An example of the display devices 131 and 132 is a liquid crystal display panel. The transmission speed may be indicated numerically in the display devices 131 and 132, or can be indicated with a bar graph or the like graphically for the speed level. Also, a light source, lamp or light emitting diode (LED) can be used for indicating the level by changing an interval of winking according to the level. Also, a color of light of the light source can be changed for indication in place of the change in the interval of winking. Furthermore, notifiers for the display devices 131 and 132 can be a loudspeaker for acoustically notifying the level of the transmission speed with sound or the like.

Also, it is possible to display environment information entirely or at least partially on the portable terminal device 23 carried by the operator T in addition to the console unit 17 or the electronic cassette 16. The CPU 17C of the console unit 17 wirelessly transmits the environment information to the portable terminal device 23. Examples of a method of the radio communication can be a method of the wireless LAN standard, and also can be short range radio communication (near field communication or NFC), such as infrared communication or Bluetooth (trade name). To this end, a short range radio communication interface 136 is incorporated in the console unit 17 for the short range radio communication with the portable terminal device 23. For the content of the transmission, it is possible to transmit all the environment information, or can be a portion of the environment information, for example, unavailability of radio communication in the image transmission, transmission speed, estimated cause of a communication failure, and the like. The portable terminal device 23 drives the display to display the received environment information from the console unit 17.

In the above embodiment, the communication tester 81 is disposed on the console unit 17 inclusive of the passive monitoring device 86, the active monitoring device 87 and the evaluation device 88. Also, the communication tester 81 can be disposed on the control interface unit 18 or the electronic cassette 16.

Unlike the X-ray imaging apparatus 12 and the medical cart 14 of the above embodiment, it is possible that the X-ray imaging apparatus is not communicable with the X-ray source apparatus of a mobile type. An X-ray imaging system of the present invention can be used in combination with the X-ray imaging apparatus and the X-ray source apparatus without having a communication interface, for example, a well-known radiation source apparatus for X-ray film, IP cassette and the like. However, it is easy to combine the electronic cassette with the X-ray source apparatus of the known type by use of the electronic cassette having a function of detecting irradiation of the above embodiments.

In the above embodiment, the medical cart 14 as the X-ray source apparatus has wheels for moving on the floor. However, an X-ray source apparatus of the invention can be manually carried for movement by an operator, and can be a structure without the cart platform 14a. The X-ray source apparatus can have an X-ray source, a source driver and a portable housing for containing those.

Examples of patients of the body P with limited mobility to be cared by use of radiographic imaging of the invention include all in-patients in hospital beds, for example, a bedridden patient who cannot stand or walk with a functional problem in legs, a patient in deep coma, and a patient in a complete bed rest for a reason of a disease, injury or surgery according to consultation of a physician or doctor.

For the electromagnetic and particular medical instruments 24 and 30 in the embodiments, the electromagnetic medical instrument 24 is an apparatus influencing the portable terminal device 23, and the particular medical instrument 30 is an apparatus receiving influence from the portable terminal device 23. However, those instruments are not limited to the above embodiments. Examples of the electromagnetic and particular medical instruments 24 and 30 with a problem of radio interference can be a heart rate monitoring apparatus, a hearing aid device of a wireless type, and the like.

In the present invention, causes of the communication failure are not limited to the above embodiments. The causes of the communication failure in the above embodiments are specifically detected by measuring the communication environment. However, plural causes of the communication failure may be grouped into a small number of example categories, so that it is possible to detect one of the example categories corresponding to a cause of the communication failure by measuring the communication environment.

It is possible according to the invention to combine plural features of the embodiments with one another. Also, radiation in radiographic imaging in the invention can be gamma rays other than X-rays.

According one embodiment mode of the invention, assuming that unavailability of the wireless transmission is judged, then the controller outputs unavailability information of the wireless transmission and countermeasure information to the display device.

According another embodiment mode of the invention, furthermore, a controller outputs message information to a display device to recommend adjustment of the relative position assuming that it is detected that the cause of the communication failure is the blocking object or the relative position.

According still another embodiment mode of the invention, at least one of a time point and position information of measurement of the transmission speed is combined with the transmission speed to produce the speed history.

According another embodiment mode of the invention, the image receiving unit includes a console unit for displaying the radiation image.

According an additional embodiment mode of the invention, furthermore, there is an interface unit for radio communication between the electronic cassette and the console unit.

According another embodiment mode of the invention, the controller performs control of transmitting entirety or part of the environment information to a portable terminal device.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A portable radiographic imaging apparatus comprising:
   an electronic cassette for imaging of a radiation image and transmitting said radiation image wirelessly;
   an image receiving unit for communicating with said electronic cassette and receiving said radiation image wirelessly;
   a passive monitoring device for receiving ambient electromagnetic waves to measure communication environment by passive monitoring;
   an active monitoring device for performing data communication between said electronic cassette and said image receiving unit to measure said communication environment by active monitoring.

2. A portable radiographic imaging apparatus as defined in claim 1, further comprising an evaluation device for detecting a cause of a communication failure by considering a result of said passive monitoring and a result of said active monitoring.

3. A portable radiographic imaging apparatus as defined in claim 2, wherein said result of said passive monitoring includes at least one of intensity of a particular frequency of said electromagnetic waves, spectral intensity of frequency distribution of said intensity of said electromagnetic waves, and a time profile of changes in said intensity or said spectral intensity with time.

4. A portable radiographic imaging apparatus as defined in claim 2, wherein said result of said active monitoring includes a transmission speed.

5. A portable radiographic imaging apparatus as defined in claim 2, further comprising a controller for outputting environment information of said communication environment to a display device, said environment information including at least one of said result of said passive monitoring, said result of said active monitoring, and said detected cause of said communication failure detected by said evaluation device.

6. A portable radiographic imaging apparatus as defined in claim 5, wherein said result of said passive monitoring includes at least one of channel information of a radio communication channel of radio waves used by a radio communication device being present locally, and noise information of electromagnetic noise created by a device being present locally.

7. A portable radiographic imaging apparatus as defined in claim 5, wherein said evaluation device further checks enablement of wireless transmission of said radiation image according to at least one of said result of said passive monitoring, said result of said active monitoring and said cause of said communication failure;
said controller further outputs information as to said enablement of said wireless transmission of said radiation image to said display device.

8. A portable radiographic imaging apparatus as defined in claim 2, wherein said passive monitoring is performed before performing said active monitoring.

9. A portable radiographic imaging apparatus as defined in claim 8, wherein said evaluation device checks whether said active monitoring should be performed according to said result of said passive monitoring.

10. A portable radiographic imaging apparatus as defined in claim 2, wherein said evaluation device checks whether a medical instrument with possibility of receiving influence of radio waves is present locally according to a waveform of electromagnetic noise, and judges unavailability of said active monitoring assuming that said medical instrument is found to be present.

11. A portable radiographic imaging apparatus as defined in claim 2, wherein said evaluation device detects that said cause of said communication failure is a blocking object blocking radio waves or a relative position between said electronic cassette and said image receiving unit according to said results of said passive and active monitoring.

12. A portable radiographic imaging apparatus as defined in claim 11, wherein said evaluation device recognizes that said cause of said communication failure is said blocking object or said relative position according to an estimated transmission speed estimated according to said result of said passive monitoring, a measured transmission speed in said result of said active monitoring, and noise information of electromagnetic noise in said result of said passive monitoring.

13. A portable radiographic imaging apparatus as defined in claim 11, further comprising a positioning aid device for outputting information for adjusting said relative position.

14. A portable radiographic imaging apparatus as defined in claim 13, wherein said information is a speed history of detected changes in a transmission speed by causing said active monitoring device to perform said active monitoring repeatedly while said relative position is adjusted.

15. A portable radiographic imaging apparatus as defined in claim 14, wherein said image receiving unit includes a position sensor, and said positioning aid device produces said speed history by combining said transmission speed and position information from said position sensor.

16. A portable radiographic imaging apparatus as defined in claim 14, wherein said positioning aid device detects an optimized position where said transmission speed is highest according to said speed history;
further comprising a controller for outputting information of said optimized position to a display device.

17. A portable radiographic imaging apparatus as defined in claim 5, wherein said image receiving unit has said passive monitoring device, said active monitoring device and said display device.

18. A portable radiographic imaging apparatus as defined in claim 2, further comprising a condition setting unit for changing a communication setting of radio communication by considering at least one of said result of said passive monitoring and said result of said active monitoring.

19. A portable radiographic imaging apparatus as defined in claim 18, wherein said condition setting unit determines said communication setting for transmitting said radiation image by considering said result of said active monitoring of plural events different in said communication setting.

20. A portable radiographic imaging system having a portable radiation source apparatus and a portable radiographic imaging apparatus, comprising:
said portable radiographic imaging apparatus including:
an electronic cassette for imaging of a radiation image and transmitting said radiation image wirelessly;
an image receiving unit for communicating with said electronic cassette and receiving said radiation image wirelessly;
a passive monitoring device for receiving ambient electromagnetic waves to measure communication environment by passive monitoring;
an active monitoring device for performing data communication between said electronic cassette and said image receiving unit to measure said communication environment by active monitoring.

* * * * *